United States Patent
Hissong et al.

(10) Patent No.: US 9,724,119 B2
(45) Date of Patent: Aug. 8, 2017

(54) METHODS OF USING HIGH INTENSITY FOCUSED ULTRASOUND TO FORM AN ABLATED TISSUE AREA CONTAINING A PLURALITY OF LESIONS

(71) Applicant: Medtronic, Inc., Minneapolis, MN (US)

(72) Inventors: James B. Hissong, Jacksonville, FL (US); Mark T. Stewart, Lino Lakes, MN (US); David E. Francischelli, Anoka, MN (US); James R. Keogh, Maplewood, MN (US); Hotaik Lee, State College, PA (US); Nadine B. Smith, Pennsylvania, PA (US); James R. Skarda, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/956,600

(22) Filed: Dec. 2, 2015

(65) Prior Publication Data
US 2016/0157883 A1    Jun. 9, 2016

Related U.S. Application Data

(62) Division of application No. 12/772,437, filed on May 3, 2010, now Pat. No. 9,227,088, which is a division
(Continued)

(51) Int. Cl.
A61B 5/05 (2006.01)
A61B 17/32 (2006.01)
(Continued)

(52) U.S. Cl.
CPC ...... *A61B 17/320068* (2013.01); *A61B 34/20* (2016.02); *A61N 7/02* (2013.01);
(Continued)

(58) Field of Classification Search
USPC ........................................................ 600/427
See application file for complete search history.

(56) References Cited

U.S. PATENT DOCUMENTS

| 3,736,936 A | 6/1973 | Basiulis et al. |
| 3,807,403 A | 4/1974 | Stumpf et al. |

(Continued)

FOREIGN PATENT DOCUMENTS

| EP | 1 095 627 | 5/2001 |
| EP | 1 750 804 | 7/2008 |
| WO | 01-80755 | 11/2001 |
| WO | 2005-113068 | 12/2005 |
| WO | 2007-067945 | 6/2007 |
| WO | 2007-140331 | 12/2007 |

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.
(Continued)

*Primary Examiner* — Joel F Brutus

(57) ABSTRACT

A device and method for ablating tissue is disclosed comprising the steps of acquiring an anatomical image of a patient, correlating the image to the patient, guiding an ablating member within the patient while tracking the position of the ablating member in the patient, positioning the ablating member in a desired position to ablate tissue, emitting ablating energy from the ablating member to form an ablated tissue area and removing the ablating member from the patient.

12 Claims, 27 Drawing Sheets

US 9,724,119 B2

Page 2

Related U.S. Application Data of application No. 11/754,045, filed on May 25, 2007, now abandoned.

(60) Provisional application No. 60/808,306, filed on May 25, 2006.

(51) Int. Cl.
*A61N 7/02* (2006.01)
*A61B 34/20* (2016.01)
A61B 18/00 (2006.01)
A61N 7/00 (2006.01)
A61B 8/00 (2006.01)
A61B 90/00 (2016.01)

(52) U.S. Cl.
CPC ............ *A61N 7/022* (2013.01); *A61B 8/4281* (2013.01); *A61B 2017/320076* (2013.01); *A61B 2018/00291* (2013.01); *A61B 2034/2051* (2016.02); *A61B 2090/378* (2016.02); *A61B 2090/3782* (2016.02); *A61N 2007/0078* (2013.01)

(56) References Cited

U.S. PATENT DOCUMENTS

| | | |
|---|---|---|
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,562,900 A | 1/1986 | Anderson et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,010,886 A | 4/1991 | Passafaro et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,314,466 A | 5/1994 | Stern et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,402,792 A | 4/1995 | Kimura |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,413,550 A | 5/1995 | Castel |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,437,664 A | 8/1995 | Cohen et al. |
| 5,441,499 A | 8/1995 | Fritzsch |
| 5,443,463 A | 8/1995 | Stern et al. |
| 5,443,470 A | 8/1995 | Stern et al. |
| 5,448,994 A | 9/1995 | Iinuma |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |

(56) References Cited

U.S. PATENT DOCUMENTS

| | | |
|---|---|---|
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,831 A | 2/1998 | Olsson et al. |
| 5,713,942 A | 2/1998 | Stern |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,728,094 A | 3/1998 | Edwards |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,755,760 A | 5/1998 | Maguire et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,802 A | 9/1998 | Panescu et al. |
| 5,817,021 A | 10/1998 | Reichenberger et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,938,612 A | 8/1999 | Kline-Schoder et al. |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,006,134 A | 12/1999 | Hill et al. |
| 6,007,499 A | 12/1999 | Martin et al. |
| 6,012,457 A | 1/2000 | Lesh |
| 6,016,811 A | 1/2000 | Knopp et al. |
| 6,042,556 A | 3/2000 | Beach et al. |
| 6,056,745 A | 5/2000 | Panescu et al. |
| 6,063,081 A | 5/2000 | Mulier |
| 6,071,279 A | 6/2000 | Whayne et al. |
| 6,088,894 A | 7/2000 | Oakley |
| 6,096,037 A | 8/2000 | Mulier |
| 6,113,592 A | 9/2000 | Taylor |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,146,379 A | 11/2000 | Fleischman |
| 6,152,920 A | 11/2000 | Thompson et al. |
| 6,161,543 A | 12/2000 | Cox et al. |
| 6,165,174 A | 12/2000 | Jacobs et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,266,564 B1 | 7/2001 | Hill et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,315,732 B1 | 11/2001 | Suorsa et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |

(56) References Cited

U.S. PATENT DOCUMENTS

| | | |
|---|---|---|
| 6,368,482 B1 | 4/2002 | Oeftering et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,720 B1 | 6/2002 | Hissong et al. |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,429,217 B1 | 8/2002 | Puskas |
| 6,430,426 B2 | 8/2002 | Avitall |
| 6,440,127 B2 | 8/2002 | McGovern et al. |
| 6,440,130 B1 | 8/2002 | Mulier |
| 6,443,952 B1 | 9/2002 | Mulier |
| 6,447,443 B1 | 9/2002 | Keogh et al. |
| 6,447,507 B1 | 9/2002 | Bednarek et al. |
| 6,451,013 B1 | 9/2002 | Bays et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,479,523 B1 | 11/2002 | Puskas |
| 6,484,727 B1 | 11/2002 | Vaska et al. |
| 6,487,446 B1 | 11/2002 | Hill et al. |
| 6,488,680 B1 | 12/2002 | Francischelli |
| 6,502,575 B1 | 1/2003 | Jacobs et al. |
| 6,508,765 B2 | 1/2003 | Suorsa et al. |
| 6,508,774 B1 | 1/2003 | Acker et al. |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Hoey |
| 6,542,774 B2 | 4/2003 | Hill et al. |
| 6,558,382 B2 | 5/2003 | Jahns |
| 6,575,956 B1 | 6/2003 | Brisken et al. |
| 6,584,360 B2 | 6/2003 | Francischelli |
| 6,585,732 B2 | 7/2003 | Mulier |
| 6,595,934 B1 | 7/2003 | Hissong et al. |
| 6,605,084 B2 | 8/2003 | Acker et al. |
| 6,610,054 B1 | 8/2003 | Edwards et al. |
| 6,610,055 B1 | 8/2003 | Swanson et al. |
| 6,610,060 B2 | 8/2003 | Mulier |
| 6,613,048 B2 | 9/2003 | Mulier |
| 6,626,855 B1 | 9/2003 | Weng et al. |
| 6,628,987 B1 | 9/2003 | Hill et al. |
| 6,645,199 B1 | 11/2003 | Jenkins et al. |
| 6,648,883 B2 | 11/2003 | Francischelli |
| 6,656,175 B2 | 12/2003 | Francischelli |
| 6,656,950 B2 | 12/2003 | Puskas |
| 6,663,627 B2 | 12/2003 | Francischelli |
| 6,690,973 B2 | 2/2004 | Hill et al. |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,718,208 B2 | 4/2004 | Hill et al. |
| 6,719,694 B2 | 4/2004 | Weng et al. |
| 6,735,471 B2 | 5/2004 | Hill et al. |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,778,854 B2 | 8/2004 | Puskas |
| 6,807,968 B2 | 10/2004 | Francischelli |
| RE38,654 E | 11/2004 | Hill et al. |
| 6,827,715 B2 | 12/2004 | Francischelli |
| RE38,705 E | 2/2005 | Hill et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,904,318 B2 | 6/2005 | Hill et al. |
| 6,911,019 B2 | 6/2005 | Mulier |
| 6,912,419 B2 | 6/2005 | Hill et al. |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 7,058,447 B2 | 6/2006 | Hill et al. |
| 7,072,720 B2 | 7/2006 | Puskas |
| 7,142,910 B2 | 11/2006 | Puskas |
| 7,184,828 B2 | 2/2007 | Hill et al. |
| 7,184,829 B2 | 2/2007 | Hill et al. |
| 7,338,434 B1 | 3/2008 | Haarstad et al. |
| 2002/0095139 A1 | 7/2002 | Keogh et al. |
| 2002/0138109 A1 | 9/2002 | Keogh et al. |
| 2002/0156470 A1 | 10/2002 | Shadduck |
| 2003/0028111 A1 | 2/2003 | Vaezy et al. |
| 2003/0045872 A1 | 3/2003 | Jacobs |
| 2003/0079753 A1* | 5/2003 | Vaska .................. A61B 18/02 128/898 |
| 2003/0144656 A1 | 7/2003 | Ocel |
| 2003/0191462 A1 | 10/2003 | Jacobs |
| 2003/0195496 A1 | 10/2003 | Maguire et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0181178 A1* | 9/2004 | Aldrich ............ A61B 18/1477 601/3 |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0254570 A1 | 12/2004 | Hadjicostis et al. |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0080469 A1* | 4/2005 | Larson .................. A61N 7/02 607/101 |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0240127 A1 | 10/2005 | Seip et al. |
| 2005/0267454 A1 | 12/2005 | Hissong |
| 2006/0009756 A1 | 1/2006 | Francischelli |
| 2006/0009759 A1 | 1/2006 | Chrisitian |
| 2006/0025756 A1* | 2/2006 | Francischelli ........... A61N 7/02 606/27 |
| 2006/0106375 A1 | 5/2006 | Wemeth et al. |
| 2006/0229594 A1 | 10/2006 | Francischelli |
| 2008/0039746 A1 | 2/2008 | Hissong |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

(56) References Cited

OTHER PUBLICATIONS

Guiraudon et al., "Surgical Repair of Wolff-Parkinson-White Syndrome: A New Closed-Heart Techique," The Annals of Thoracic Surgery 37(1): 67-71, 1984.
Klein et al., "Surgical Correction of the Wolff-Parkinson-White Syndrome in the Closed Heart Using Cryosurgery: A Simplified Approach," JACC 3(2): 405-409, 1984.
Randall et al., "Local Epicardial Chemical Ablation of Vagal Input to Sino-Atrial and Atrioventricular Regions of the Canine Heart," Journal of the Autonomic Nervous System 11:145-159, 1984.
Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.
Gallagher et al., "Surgical Treatment of Arrhythmias," The American Journal of Cardiology 61:27A-44A, 1988.
Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.
Cox et al., Surgery for Atrial Fibrillation; Seminars in Thoracic and Cardiovascular Surgery , vol. 1, No. 1 (Jul. 1989) pp. 67-73.
Bredikis and Bredikis; Surgery of Tachyarrhythmia: Intracardiac Closed Heart Cryoablation; PACE, vol. 13, pp. 1980-1984.
McCarthy et al., "Combined Treatment of Mitral Regurgitation and Atrial Fibrillation with Valvuloplasty and the Maze Procedure," The American Journal of Cardiology 71: 483-486, 1993.
Yamauchi et al. "Use of Intraoperative Mapping to Optimize Surgical Ablation of Atrial Flutter," The Annals of Thoracic Surgery 56: 337-342, 1993.
Graffigna et al., "Surgical Treatment of Wolff-Parkinson-White Syndrome: Epicardial Approach Without the Use of Cardiopulmonary Bypass," Journal of Cardiac Surgery 8: 108-116, 1993.
Siefert et al., "Radiofrequency Maze Ablation for Atrial Fibrillation," Circulation 90(4): I-594.
Surgical treatment of atrial fibrillation: a review; Europace (2004) 5, S20-S29 (abstract only).
Elvan et al., "Radiofrequency Catheter Ablation of the Atria Reduces Inducibility and Duration of Atrial Fibrillation in Dog," Circulation 91: 2235-2244, 1995.
Cox et al., "Modification of the Maze Procedure for Atrial Flutter and Atrial Fibrillation. I. Rational and Surgical Results," The Journal of Thoracic Cardiovascular Surgery 110: 473-484, 1995.
Cox, "The Maze III Procedure for Treatment of Atrial Fibrillation," Sabiston DC, ed Atlas of Cardiothoracic Surgery, Philadelphia: WB Saunders: 460-475, 1994.
Sueda et al., "Simple Left Atrial Procedure for Chronic Atrial Fibrillation Associated with Mitral Valve Disease," The Annals of Thoracic Surgery 62(6): 1796-1800, 1996.
Tsui et al., "Maze 3 for Atrial Fibrillation: Two Cuts Too Few?" PACE 17: 2163-2166, 1994.
Kosakai et al., "Cox Maze Procedure for Chronic Atrial Fibrillation Associated with Mitral Valve Disease," The Journal of Thoracic Cardiovascular Surgery 108: 1049-1055, 1994.
Cox et al., "The Surgical Treatment of Atrial Fibrillation, IV Surgical Technique," *J of Thorac Cardiovasc Surg*, 1991: 101: 584-593.
Nardella, "Radio Frequency Energy and Impedance Feedback," SPIE vol. 1068, Catheter Based Sensing and Imaging Technology (1989).
Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.
Sie et al., "Radiofrequency Ablation of Atrial Fibrillation in Patients Undergoing Mitral Valve Surgery. First Experience," Circulation (Nov. 1996) 96:450,I-675,#3945.
Sie et al., "Radiofrequency Ablation of Atrial Fibrillation in Patients Undergoing Valve Surgery," Circulation (Nov. 1997) 84:I450,#2519.
Jais et al., "Catheter Ablation for Paroxysmal Atrial Fibrillation: High Success Rates with Ablation in the Left Atrium," Circulation (Nov. 1996) 94:I-675,#3946.
Cox, "Evolving Applications of the Maze Procedure for Atrial Fibrillation," Ann Thorac Surg, 1993;55:578-580.
Cox et al. "Five-Year Experience with the Maze Procedure for Atrial Fibrillation," Ann Thorac Surg, 1993; 56:814-824.
Avitall et al., "New Monitoring Criteria for Transmural Ablation of Atrial Tissues," Circulation, 1996;94(Supp 1):I-493, #2889.
Cox et al., "An 8½ Year Clinical Experience with Surgery for Atrial Fibrillation," Annals of Surgery, 1996;224(3):267-275.
Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.
Haissaguerre et al., "Right and Left Atrial Radiofrequency Catheter Therapy of Paroxysmal Atrial Fibrillation," Journal of Cardiovascular Electrophysiology, 1996;7(12):1132-1144.
Haissaguerre et al., "Role of Catheter Ablation for Atrial Fibrillation," Current Opinion in Cardiology, 1997;12:18-23.
Kawaguchi et al., "Risks and Benefits of Combined Maze Procedure for Atrial Fibrillation Associated with Organic Heart Disease," JACC, 1996;28(4):985-990.
Cox, et al., "Perinodal cryosurgery for atrioventricular node reentry tachycardia in 23 patients," Journal of Thoracic and Cardiovascular Surgery, 99:3, Mar. 1990, pp. 440-450.
Cox, "Anatomic-Electrophysiologic Basis for the Surgical Treatment of Refractory Ischemic Ventricular Tachycardia," Annals of Surgery, Aug. 1983; 198:2;119-129.
Williams, et al., "Left atrial isolation," J Thorac Cardiovasc Surg; 1980; 80: 373-380.
Scheinman, "Catheter-based Techniques for Cure of Cardiac Arrhythmias," Advances in Cardiovascular Medicine, 1996, ISSN 1075-5527, pp. 93-100.
Sueda et al., "Efficacy of a Simple Left Atrial Procedure for Chronic Atrial Fibrillation in Mitral Valve Operations," Ann Thorac Surg, 1997;63:1070-1075.
U.S. Appl. No. 60/123,505, filed Mar. 9, 1999.

\* cited by examiner

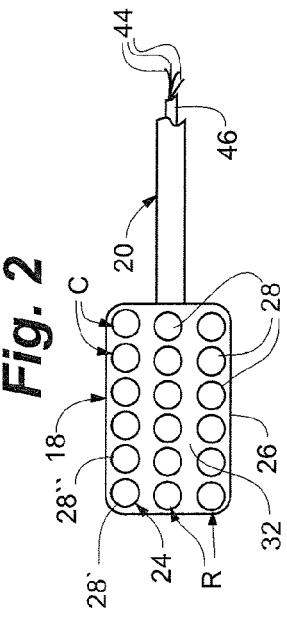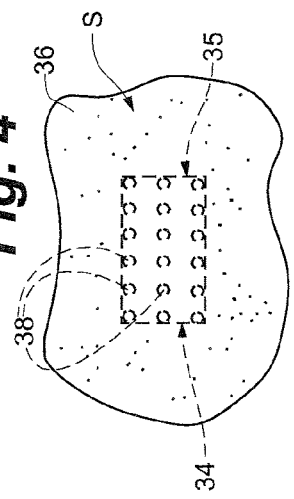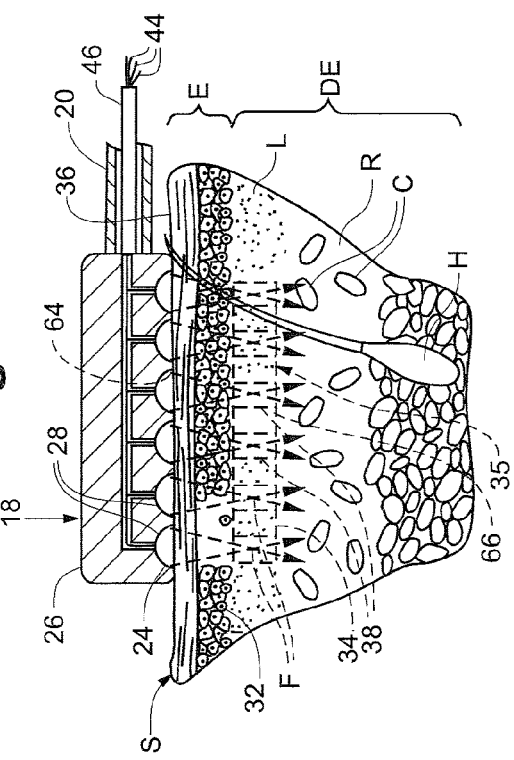

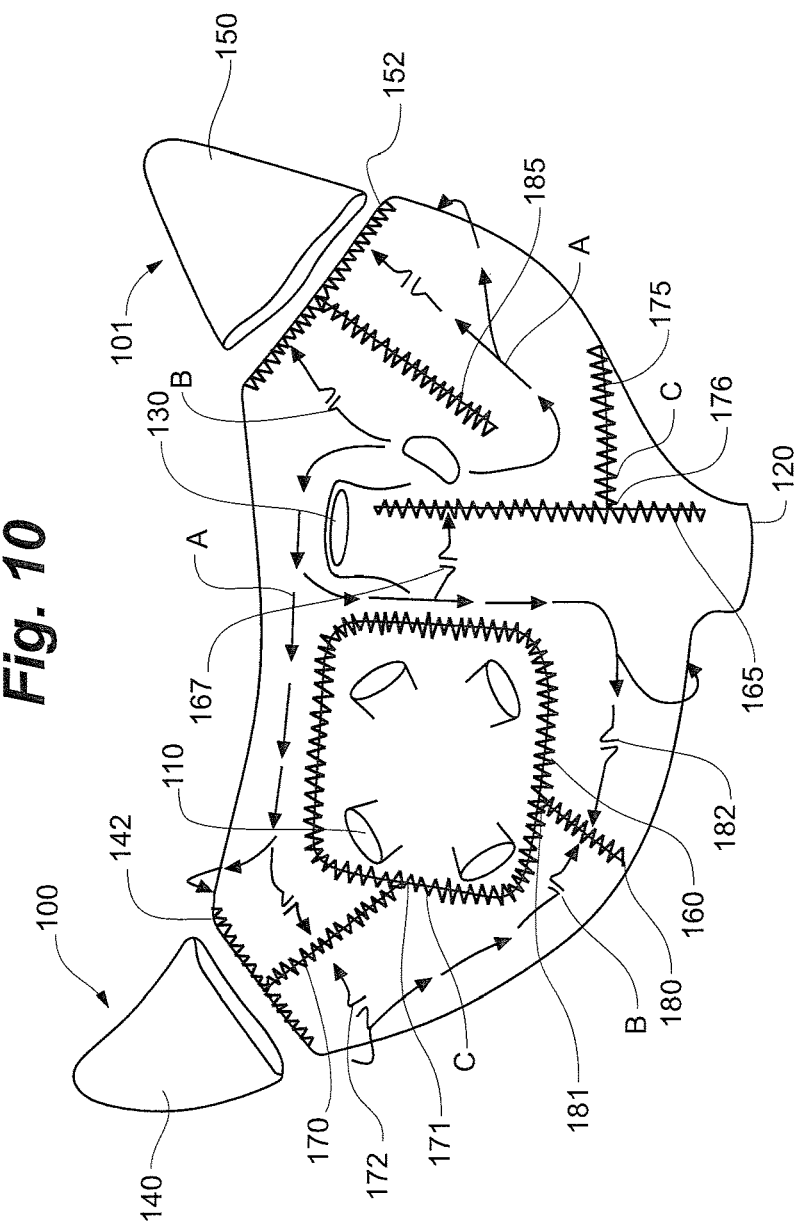

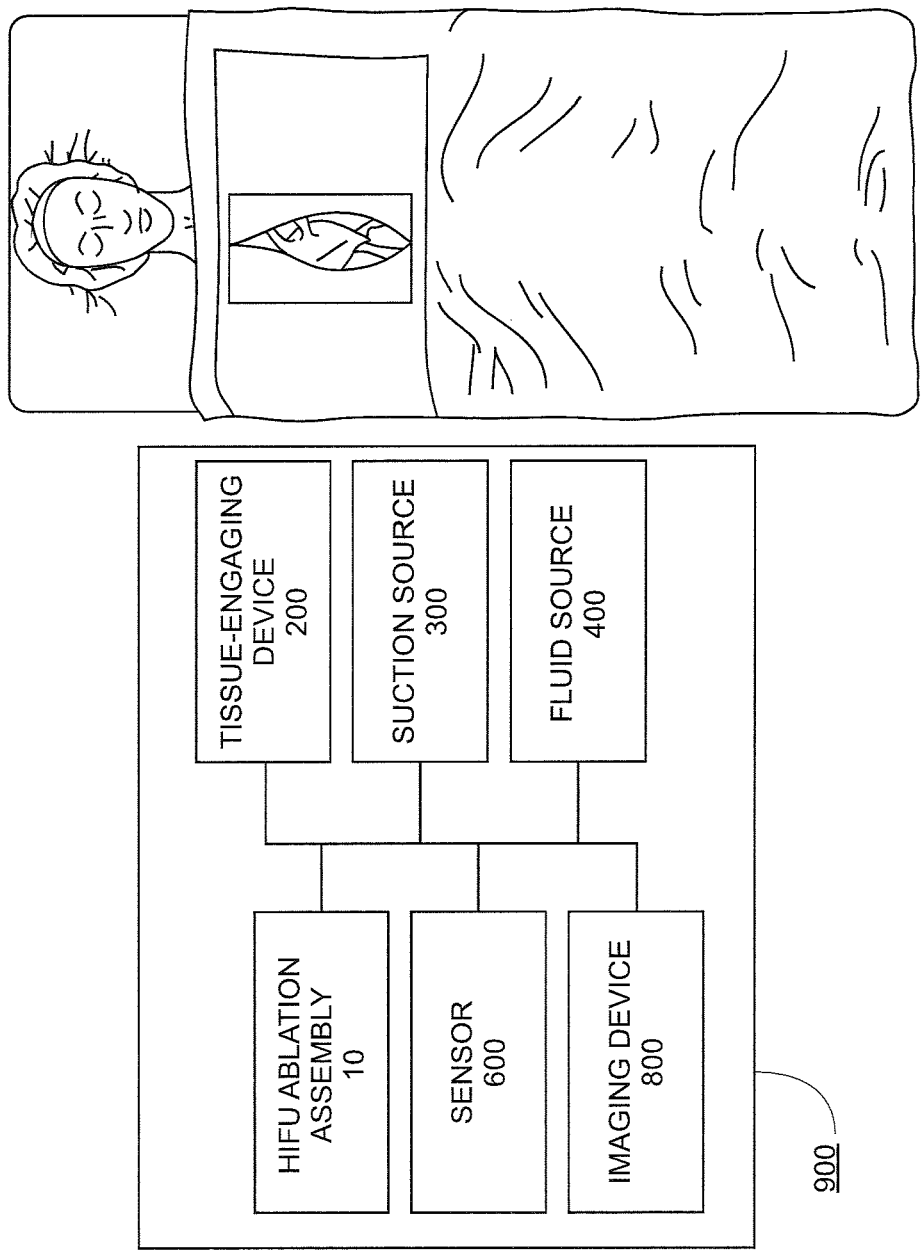

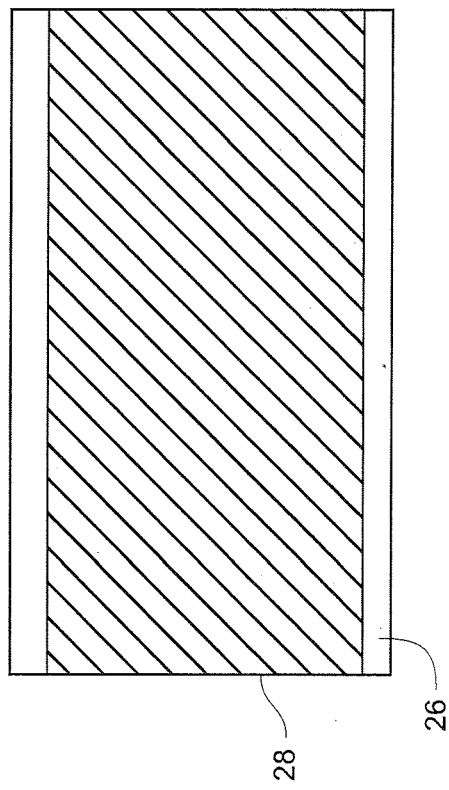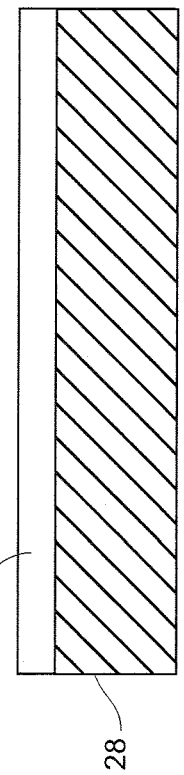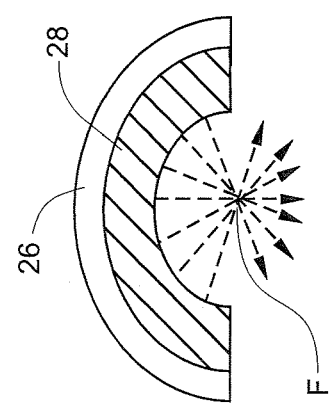

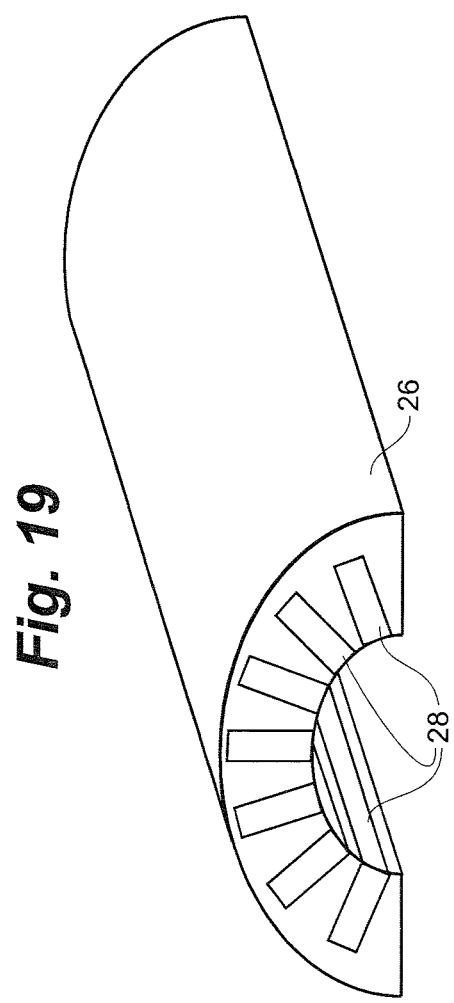

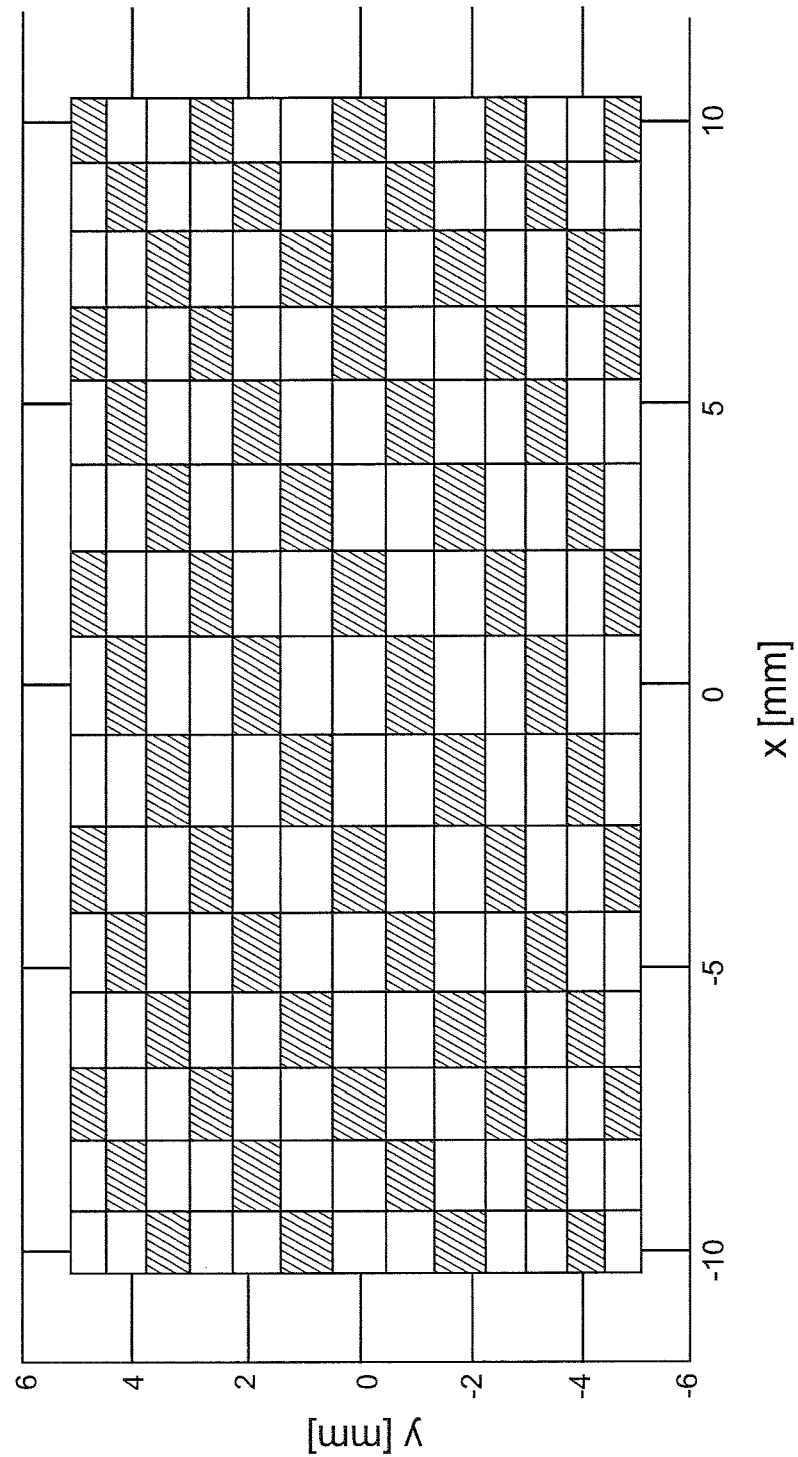

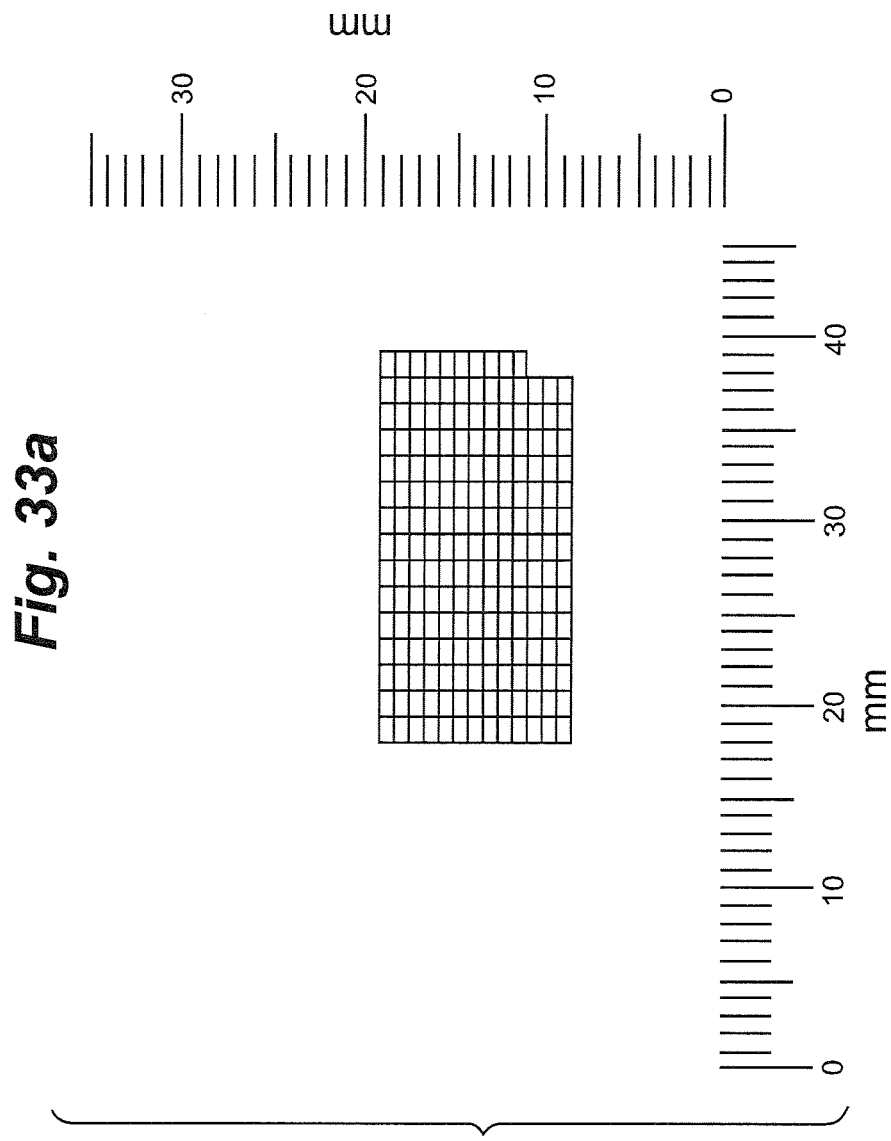

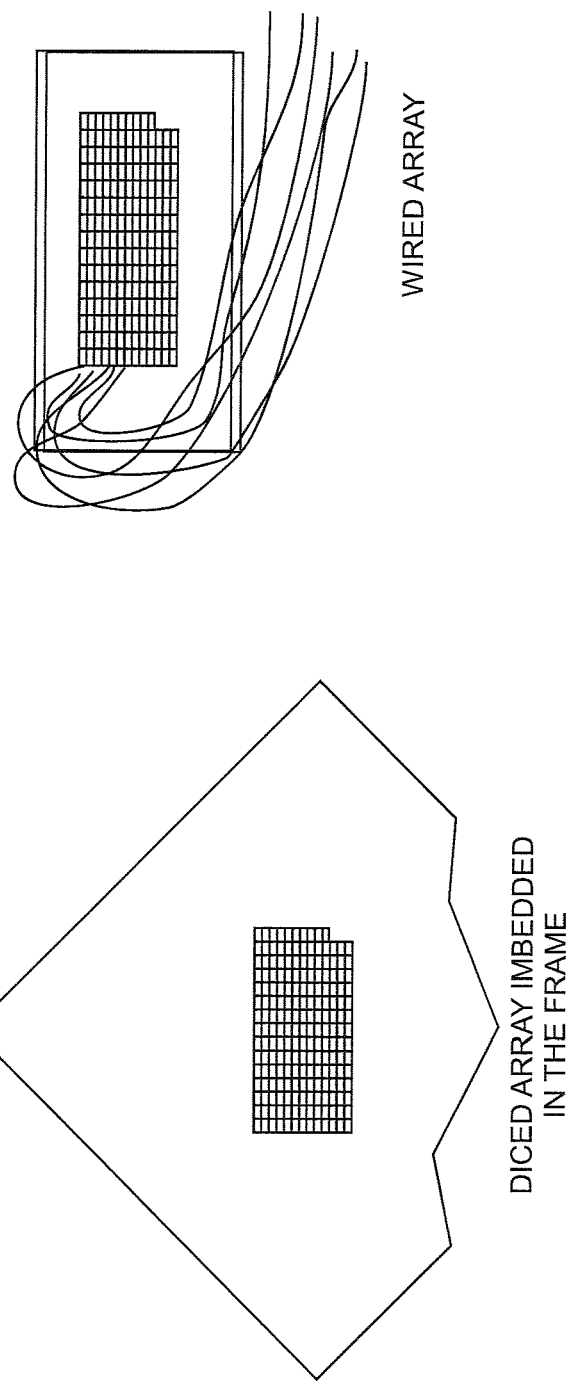

METHODS OF USING HIGH INTENSITY FOCUSED ULTRASOUND TO FORM AN ABLATED TISSUE AREA CONTAINING A PLURALITY OF LESIONS

RELATED APPLICATIONS

This application is a division of U.S. patent application Ser. No. 12/772,437, filed May 3, 2010, now allowed, which is a division of U.S. patent application Ser. No. 11/754,045, filed May 25, 2007, which claims priority to U.S. Provisional Patent Application No. 60/808,306, filed May 25, 2006.

FIELD OF THE INVENTION

The present invention relates generally to the treatment of tissue of a patient with ablative energy and, more particularly, to the ablation of tissue using image guidance.

BACKGROUND OF THE INVENTION

When ablative energy, e.g., high intensity focused ultrasound (HIFU) energy, radiofrequency (RF) energy, microwave energy and/or laser energy, is applied to tissue, significant physiological effects may be produced in the tissue resulting from thermal and/or mechanical changes or effects in the tissue. Thermal effects include heating of the tissue; and, when the tissue is heated to a sufficiently high temperature, tissue damage such as coagulative necrosis can be produced. In order to produce thermal effects in tissue, ablating members, e.g., ultrasound emitting members such as transducers or electrodes, have been used to emit ablative energy which is applied to tissue. For example, ablating members may by positioned adjacent or in contact with the tissue or by coupling the ablating members to the tissue via a coupling medium, stand-off and/or sheath. By focusing the ablating energy at one or more specific focusing zones within the tissue, thermal effect can be confined to a defined location, region, volume or area. Depending on the type of ablative energy used, the location, region, volume or area that is ablated may be remote from the ablating member.

With the use HIFU, one or more focusing zones at or within a designated target location, region, volume or area within a larger mass, body or area of tissue can be subjected to high intensity ultrasound energy while tissue surrounding the target area is subjected to much lower intensity ultrasound energy. In this manner, tissue in the target area can be heated to a sufficiently high temperature so as to cause a desired thermal effect such as tissue damage, ablation, coagulation, denaturation, destruction or necrosis while tissue surrounding the target area is not heated to damaging temperatures and, therefore, is preserved. Heating of tissue in a target location, volume, region or area to an ablative temperature creates an ablative lesion in the tissue in the target location, volume, region or area that is desirable in the treatment of various medical conditions, disorders or diseases. For example, the lesion may remain as tissue having altered characteristics or may be naturally degraded and absorbed by the patient's body and thusly eliminated such that the remaining body, mass or area of tissue is of smaller volume or size due to the absence of the ablated tissue.

The use of HIFU to eliminate tissue or to alter the characteristics of tissue in a target location, volume, region or area within a larger mass, body or area of tissue presents many advantages including minimization of trauma and pain for the patient, elimination of the need for a surgical incision, stitches and exposure of internal tissue, avoidance of damage to tissue other than that which is to be treated, altered or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an outpatient basis.

The action of the heart is known to depend on electrical signals within the heart tissue. Occasionally, these electrical signals do not function properly, thereby causing heart arrhythmias. Heart arrhythmias, such as atrial fibrillation, have been treated by surgery. For example, a surgical procedure called the "Maze" procedure was designed to eliminate atrial fibrillation permanently. The procedure employs incisions in the right and left atria which divide the atria into electrically isolated portions which in turn results in an orderly passage of the depolarization wave front from the sino-atrial node (SA node) to the atrial-ventricular node (AV node) while preventing reentrant wave front propagation. Although successful in treating AF, the surgical Maze procedure is quite complex and is currently performed by a limited number of highly skilled cardiac surgeons in conjunction with other open-heart procedures. As a result of the complexities of the surgical procedure, there has been an increased level of interest in procedures employing ultrasound devices or other types of ablation devices, e.g. thermal ablation, microwave ablation, RF ablation, cryo-ablation or the like to ablate tissue along pathways approximating the incisions of the Maze procedure. Electrosurgical systems for performing such procedures are described in U.S. Pat. No. 5,916,213 to Haissaguerre, et al., U.S. Pat. No. 5,957,961 to Maguire, et al. and U.S. Pat. No. 5,690,661, all incorporated herein by reference in their entireties. Procedures are also disclosed in U.S. Pat. No. 5,895,417 to Pomeranz, et al, U.S. Pat. No. 5,575,766 to Swartz, et al., U.S. Pat. No. 6,032,077 to Pomeranz, U.S. Pat. No. 6,142,994 to Swanson, et al. and U.S. Pat. No. 5,871,523 to Fleischman, et al., all incorporated herein by reference in their entireties. Cryo-ablation systems for performing such procedures are described in U.S. Pat. No. 5,733,280 to Avitall, also incorporated herein by reference in its entirety. High intensity focused ultrasound systems for performing such procedures are described in U.S. Patent Application Publication No. 2005/0080469 to Larson et al. and U.S. Pat. No. 6,858,026 to Sliwa et al., U.S. Pat. No. 6,840,936 to Sliwa et al., U.S. Pat. No. 6,805,129 to Pless et al. and U.S. Pat. No. 6,805,128 to Pless et al., all incorporated herein by reference in their entireties.

High intensity focused ultrasound is an attractive surgical ablation modality as the energy can be focused to create heat at some distance from the ablating member (or transducer). In epicardial applications, most of the heat loss is to the blood, which is also some distance from the transducer. This is in contrast to most other technologies, in which heating occurs close to the ablating element (or electrode) and deeper heating is by thermal conduction. Additionally, since the coronary arteries are typically towards the epicardial surface, they are theoretically less susceptible to heating and subsequent constriction by a device such as a HIFU device, which can generate heat deep within the myocardium. For example, a non-irrigated RF epicardial ablation approaches has the highest heating occurring at the epicardial surface. Any transfer of heat to the deeper endocardium is by thermal conduction. Irrigated RF epicardial ablation approaches allow the heat to penetrate deeper into the tissue, but tend to be limited in depth. In contrast, a HIFU approach can focus the energy to generate heat deeper within the tissue at a substantial distance from the transducer.

Another therapeutic method to terminate AF is to ablate an area that is sufficiently large enough such that there is not enough critical mass to sustain the reentrant waveform characteristic of the arrhythmia.

In conjunction with the use of ablation devices, various control mechanisms have been developed to control delivery of ablation energy to achieve the desired result of ablation, i.e. killing of cells at the ablation site while leaving the basic structure of the organ to be ablated intact. Such control systems may include measurement of temperature and/or impedance at or adjacent to the ablation site, as are disclosed in U.S. Pat. No. 5,540,681 to Struhl, et al., incorporated herein by reference in its entirety.

Additionally, there has been substantial work done toward assuring that the ablation procedure is complete, i.e. that the ablation extends through the thickness of the tissue to be ablated, before terminating application of ablation energy. This desired result is some times referred to as a "transmural" ablation. For example, detection of a desired drop in electrical impedance at the electrode site as an indicator of transmurality is disclosed in U.S. Pat. No. 5,562,721 to Marchlinski et al., incorporated herein by reference in its entirety. Alternatively, detection of an impedance rise or an impedance rise following an impedance fall are disclosed in U.S. Pat. No. 5,558,671 to Yates and U.S. Pat. No. 5,540,684 to Hassler, respectively, also incorporated herein by reference in their entireties.

Sometimes ablation is necessary only at discrete positions along the tissue. This is the case, for example, when ablating accessory pathways, such as in Wolff-Parkinson-White syndrome or AV nodal reentrant tachycardias. At other times, however, ablation is desired along a line, called linear ablation. This is generally the case for atrial fibrillation, where the aim is to reduce the total mass of electrically connected atrial tissue below a threshold believed to be critical for sustaining multiple reentry wavelets. Linear lesions are created between electrically non-conductive anatomic landmarks to reduce the contiguous atrial mass.

Various approaches have been employed to create elongated lesions using ablation devices. The first approach is simply to create a series of short lesions using an ablating member, e.g., an electrode, moving it along the surface of the organ wall to be ablated to create a linear lesion. This can be accomplished either by making a series of lesions, moving the ablating member between lesions or by dragging the ablating member along the surface of the organ to be ablated and continuously applying ablation energy, e.g., as described in U.S. Pat. No. 5,897,533 to Mulier, et al., incorporated herein by reference in its entirety.

A second approach to creation of elongated lesions is simply to employ an elongated ablating member, e.g., an elongated electrode, and to place the elongated ablating member along the desired line of lesion along the tissue. This approach is described in U.S. Pat. No. 5,916,213, cited above. A third approach to creation of elongated lesions is to provide a series of ablating elements, e.g., a series of spaced-apart band or coil electrodes, and arrange the series of ablating elements along the desired line of lesion. After the ablating portion of the ablation device has been properly positioned, the ablating elements are energized simultaneously or one at a time to create the desired lesion. If the ablating elements are close enough together the lesions can run together sufficiently to create a continuous linear lesion. Electrodes that may be activated individually or in sequence, are disclosed in U.S. Pat. No. 5,957,961, also cited above. In the case of multi-ablating element devices, individual feedback regulation of ablated energy applied via the ablating elements may also be employed.

A method used for guidance for various medical devices in minimally invasive and robotic surgery, e.g., cardiothoracic surgery, is that of endoscopic visualization. Images from endoscopic light guides and cameras placed within a patient's body, e.g., the patient's thoracic cavity, may be displayed on a video monitor that is viewed by a surgeon. The effective use of an endoscopic visualization method depends on there being sufficient open space within the working area of the body. Various retractors and tissue spreading instruments are sometimes used to hold tissues away from the working field within the body. Pressurized gas or gasses may be introduced into the thoracic cavity to help create space in which to work with a sufficient field of view. A lung may be deflated to drop it away from the working field. Without sufficient space and field of view, it is difficult for the surgeon to recognize the anatomical location and identity of structures viewed on the video display. The requirement for space surrounding the working field has the effect of limiting the regions which can be safely and confidently accessed by minimally invasive endoscopic techniques. For example, it is very difficult for the surgeon to endoscopically visualize the passage of instruments through the spaces posterior to and around portions of the heart such as the transverse and oblique sinuses. Due to these limitations, some procedures have not been attempted using minimally invasive endoscopic techniques. Other methods or techniques that may be used for guidance or navigation of various surgical instruments in minimally invasive medical procedures, include electromagnetic methods, electric field methods and ultrasound methods.

SUMMARY OF THE INVENTION

Accordingly, it is an object of the present invention to ablate tissue using navigation or guidance and, more particularly, to treat AF using ablation and navigation or guidance.

It is also an object of the present invention is to utilize ablation and navigation or guidance to perform one or more lesions of a Maze procedure.

Another object of the present invention is to utilize ablation and navigation or guidance to ablate a substantial portion of the atria in order to "debulk" the chamber such that the substrate is modified sufficiently to prevent the maintenance of AF.

Another object of the present invention is to utilize ablation and navigation or guidance to ablate the parasympathetic neurons and/or the autonomic ganglia and their regions of innervation of the heart such that the neural impulses promoting AF are blocked.

Another object of the present invention is to utilize ablation and navigation or guidance to ablate specific locations within the heart that are responsible for initiating arrhythmias. These locations are often referred to as "triggers".

Still further, the present invention has as an object to utilize navigation or guidance to navigate or guide at least a portion of an ablation device placed within the esophagus, the trachea, the vasculature and/or in a trans-thoracic approach from outside the chest, for example, to form one or more lesions of a Maze procedure. At least a portion of an ablation device may be placed within the thoracic cavity, for example, intercostally or subcostally as well as by a subxiphoid approach.

It is still another object of the present invention to have an organ positioning system and method that comprises a device that engages organ tissue and allows a surgeon to easily position, manipulate, stabilize and/or hold an organ during a guided or navigated ablation procedure.

It is still another object of the present invention to place a guided or navigated ablation device on the epicardial surface of the heart and ablate tissue. The ablating energy delivered by the device may be focused at a distance from the device to ablate the underlying myocardium without affecting the coronary arteries and sinus. Such a device may be used to ablate the left atrial isthmus, as well as other lesions, for example Maze-type lesions.

Another object of the present invention is to temporarily and controllably start and stop the heart during a guided or navigated ablation procedure. For example, controlled intermittent asystole (CIA) may be used to control or inhibit motion associated with cardiac contraction such that a relatively stationary volume of cardiac tissue may be targeted with ablating energy. Cardiac and/or respiration gating may also be used during a guided or navigated ablation procedure.

Another object of the present invention is to have an organ positioning system and method that comprises a device that engages organ tissue and allows a surgeon to easily position, manipulate, stabilize and/or hold an organ during a controlled intermittent asystole, guided or navigated ablation procedure.

Some of the advantages of the present invention are that varying intensity levels of ablating energy can be delivered to tissue for varying periods of time depending on desired ablative effect, the duration of ablating energy delivery or application to the tissue needed to accomplish a desired effect may be relatively brief depending on desired size for the lesions of the ablated tissue area and/or desired thermal effect on the tissue, the ablating member used to deliver the ablating energy may be stationary or may be movable, or may be a microprocessor-controlled phased array in order to scan a target area with ablating energy, a plurality of individual ablated tissue areas can be formed in the tissue with the ablated tissue areas being separate and discontinuous or being contacting, abutting, contiguous or overlapping to form a single continuous ablated tissue area of desired size and/or shape, the ablating member can remain stationary or can be moved along to scan a target area with ablating energy, the ablating member may be designed with a focusing configuration designed to ensure that the lesions of the ablated tissue area have a desired cross-sectional size, begin a desired depth within the tissue and have a desired depth, the ablating member may be positioned externally adjacent or in contact with an external surface of the tissue or may be acoustically coupled with the tissue to form an internal ablated tissue area without damaging the tissue surface and, in particular, a body cavity such as the esophagus or trachea, and an ablated tissue area of definitive size can be repeatedly and consistently produced. The esophagus is close to the posterior of the left atrium of the heart. This position makes it particularly attractive for trans-esophageal echocardiography (TEE) imaging as well as trans-esophageal ultrasound ablation.

The ablating elements of a phased array may be electronically controlled such that individual ablating elements can be controlled to interfere with the adjacent ablating elements. This interference, for example, can be used to "steer" the focal point of an acoustical energy to virtually any spot. For example, each element may be independently controlled and energized slightly out of phase with one another to electronically steer the focal point.

These and other objects, advantages and benefits are realized with the present invention as generally characterized in a method of tissue ablation using guidance or navigation. Ablating energy may be focused within the tissue at one or more overlapping or non-overlapping focusing zones contained in a target area. If multiple focusing zones are desired, the focusing zones may be spaced from one another. The tissue is heated at the focusing zones by the ablating energy, thereby forming an ablated tissue area. Once an ablated tissue area of desired extent has been obtained, the ablating member may be removed.

An ablating member may have a focusing configuration that causes the ablating energy to be focused a predetermined distance from an active face of the ablating member. Also, the focusing configuration results in formation of lesions of predetermined or known depth in accordance with the length of the focusing zones, the selected ablating energy intensities and frequencies and the selected duration times for ablating energy delivery. The lesion depths are selected so that the lesions do not extend deeper than desired, thereby avoiding unwanted damage to surrounding tissue. The plurality of lesions may be non-contacting, with each lesion surrounded by unablated tissue. One or more of the plurality of lesions may contact another one of the plurality of lesions. The cross-sectional size of the lesions and the location and arrangement of the focusing zones in the tissue result in formation of a specific size ablated tissue area having a specific cross-sectional configuration. A single, discrete ablated tissue area or a plurality of single, discrete ablated tissue areas can be formed in the tissue in a single procedure or treatment performed at one time or in multiple procedures or treatments performed at different times. Where a plurality of ablated tissue areas are formed, the ablated tissue areas can be contiguous, contacting, overlapping or in abutment with one another so that the ablated tissue areas together form or create a single ablated tissue area of larger cross-sectional size and/or of a desired cross-sectional configuration.

One aspect of the present invention provides a system for positioning, manipulating, holding, grasping, immobilizing and/or stabilizing an organ, such as a heart. The system may include one or more tissue-engaging devices, one or more suction sources, one or more fluid sources, one or more ablation devices, one or more sensors and one or more processors. The system may also include one or more imaging devices, guidance devices, drug delivery devices and/or illumination devices. A tissue-engaging device of the system may comprise a tissue-engaging head, a support apparatus and a clamping mechanism for attaching the tissue-engaging device to a stable object, such as a retractor that is fixed to a patient's chest or an operating table. A tissue-engaging device of the system may comprise one or more energy transfer elements connected to an energy source, one or more sensors connected to a processor, one or more suction openings connected to a suction source, and/or one or more fluid openings connected to a fluid source.

Another aspect of the present invention provides a method of positioning, manipulating, holding, grasping, immobilizing and/or stabilizing an organ, such as a heart. The method includes engaging and positioning an organ, such as a heart, during an ablation procedure. The ablation procedure may include intermittently stimulating a vagal nerve and/or pacing a heart. The ablation procedure may include placement of a lead on or within a heart. The ablation procedure may include the use of suction to engage and position an organ, such as a heart. The ablation procedure may include the delivery of fluids, gases, and/or agents, such as drugs.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

BRIEF DESCRIPTION OF THE DRAWINGS

FIG. 1 is a broken perspective view, partly schematic, illustrating a high intensity focused ultrasound stimulation or ablation assembly for use in the methods of the present invention.

FIG. 2 is a broken bottom view of an ultrasound emitting member of a focused ultrasound ablation device of the high intensity focused ultrasound stimulation or ablation assembly.

FIG. 3 is a broken side view, partly in section, of the ultrasound emitting member and depicting focusing of ultrasound energy in tissue to form an ablated tissue area containing unablated tissue and a plurality of lesions at which the tissue is ablated.

FIG. 4 is a broken top view illustrating the surface or cross-sectional configuration of the ablated tissue area of FIG. 3.

FIG. 10 shows a schematic picture of various transmural lesions of a Maze procedure which can be made with the instrument according to the invention, and which can block electrical impulses in directions crosswise to said lesions.

FIG. 11 is a schematic view of one embodiment of a system in accordance with the present invention.

FIG. 18a is a cross-sectional view of a portion of an ultrasound emitting member of a focused ultrasound ablation device of the high intensity focused ultrasound stimulation or ablation assembly.

FIG. 18b is a bottom view of a portion of an ultrasound emitting member of a focused ultrasound ablation device of the high intensity focused ultrasound stimulation or ablation assembly.

FIG. 18c is a side view of a portion of an ultrasound emitting member of a focused ultrasound ablation device of the high intensity focused ultrasound stimulation or ablation assembly.

FIG. 19 is a cross-sectional view of a portion of an ultrasound emitting member of a focused ultrasound ablation device of the high intensity focused ultrasound stimulation or ablation assembly.

FIG. 25 is a view of a phased array in accordance with one embodiment of the present invention.

FIGS. 33a, 33b and 33c are views of a portion of one embodiment of a medical device in accordance with the present invention.

DESCRIPTION OF THE PREFERRED EMBODIMENTS

Figure 7:
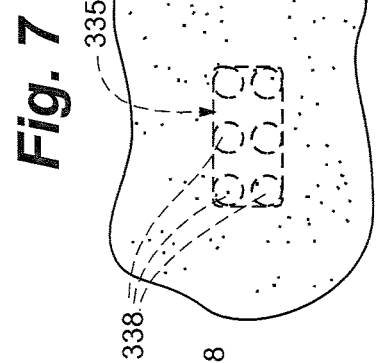
FIG. 7 is a broken top view illustrating the surface or cross-sectional configuration of another alternative ablated tissue area created in the tissue.

The entire content of U.S. patent application Ser. No. 11/754,045 filed May 25, 2007, and U.S. Provisional Patent Application No. 60/808,306 filed May 25, 2006, is hereby incorporated by reference.

One embodiment of an ablation or stimulation assembly or system 10 for use in the methods of the present invention is illustrated in FIG. 1 and is similar to the HIFU stimulation assembly described in prior U.S. patent application Ser. No. 10/464,213 and U.S. patent application Ser. No. 10/600,871, the disclosures of which are incorporated herein by reference. The high intensity focused ultrasound ablation or stimulation assembly or system 10 includes a focused ultrasound ablation or stimulation device 12, a power supply 14 and a controller 16. The focused ultrasound ablation or stimulation device 12 is similar to that described in U.S. patent application Ser. Nos. 10/464,213 and 10/600,871 and includes a focused ultrasound emitting member 18, an elongate handle shaft or body 20 having a distal end at which the ultrasound emitting member is disposed and a handle or handpiece 22 coupled to a proximal end of the handle shaft 20. As shown in FIGS. 2 and 3, the ultrasound emitting member includes a transducer 24 carried by or within a housing, carrier or case 26. The transducer, which includes one or more individual ultrasound emitting elements or transducer elements, is capable of generating and emitting ultrasound energy in response to being supplied with electrical power from power supply 14. In the case of ultrasound emitting member 18, the transducer includes a plurality of individual ultrasound emitting elements or transducer elements 28, each including a piezoelectric element that vibrates to produce ultrasound energy when an electrical potential or signal is supplied thereto. The transducer elements 28 have a focusing configuration or geometry that results in the ultrasound energy produced thereby being focused a fixed distance from the ultrasound emitting member. The transducer elements 28 have a partial spherical or concave configuration and/or include one or more lens causing the ultrasound energy generated thereby to be focused, as shown by arrows in FIG. 3, at focusing zones F, respectively.

The transducer elements 28 are arranged in an array on or in housing 26; and, therefore, the transducer 24 may be considered a multi-array transducer. In the case of ultrasound emitting member 18, the transducer elements are shown arranged in a planar array of three rows R and six columns C, although the transducer elements can be arranged in any number of rows and columns. Alternatively, the transducer elements may be angled to a more central area to create a lesion of a desired shape rather than in a row aimed along the same axis. In the case of focused ultrasound emitting member 18, each row R has an equal number of transducer elements, and each column C has an equal number of transducer elements. It should be appreciated that any number of transducer elements can be provided in each row and column and that the number of transducer elements provided in each row and column can be the same or different. Alternatively, the individual transducer element or elements mounted in the housing may be of an elongated or linear shape and may be largely aligned parallel with each other. Each of these linear elements would be capable of producing a line of focused energy.

The transducer elements 28 can be referenced by their location in the array. For example, the transducer element 28 in the first row, first column can be designated transducer element R1C1, the transducer element 28 in the first row, second column can be designated transducer element R1C2 and so on. The transducer elements may be disposed as close as possible to one another; however, it should be appreciated that the spacing between the individual transducer elements 28 of the array can vary so that adjacent transducer elements can be disposed closer together or further apart from one another. As explained further below, the transducer elements 28 may be selectively, independently actuatable to selectively emit or not emit ultrasound energy.

The transducer elements 28 can be designed in various ways as known in the art. In the case of transducer 24, the transducer elements each comprise a piezoelectric element formed by a layer of piezoelectric material carried by housing 26. The piezoelectric elements are recessed from a planar external lower or bottom surface 32 of housing 26. The piezoelectric elements are curved in a direction inwardly of surface 32 such that ultrasound energy generated by the piezoelectric elements is emitted from focused ultrasound emitting member 18 in a direction perpendicular to surface 32 for focusing at the focusing zones F, which are spaced outwardly of surface 32. Accordingly, surface 32 is an active surface or face of the ultrasound emitting member which, when positioned externally on, adjacent or in contact with tissue S, results in the ultrasound energy emitted by the transducer being focused at zones F, which will be disposed within the tissue S as shown in FIG. 3. When the ultrasound emitting member is positioned on, against or adjacent the tissue S at a location aligned with a designated target area 34 within the tissue S, the target area 34 being shown in dotted lines in FIGS. 3 and 4, the focusing zones will be disposed at or within the target area as best shown in FIG. 3.

Each focusing zone F consists of a single point or a plurality of points forming a zone at which the ultrasound energy is focused. Each focusing zone is in line with a central axis of the corresponding transducer element. Each focusing zone is disposed a fixed predetermined distance from a plane containing the active face 32, the predetermined distance for each focusing zone being perpendicular or normal to the active face 32. Therefore, the focusing zones F will also be disposed a predetermined perpendicular distance or a calculable or determinable perpendicular distance from an external surface 36 of tissue S with which the active face 32 is placed in contact or adjacent thereto. Where the active face 32 is placed in contact with the external tissue surface 36, the perpendicular distance that zones F are disposed from external tissue surface 36 will be the same as the predetermined distance. Where the active face 32 is not placed in contact with the external tissue surface 36 but, rather, is spaced from the external tissue surface 36 by a known amount, for example, the perpendicular distance that zones F are disposed from the external tissue surface will correspond to the predetermined distance minus the distance that the active face 32 is spaced from the external tissue surface 36. Where the active face 32 is spaced from the external tissue surface 36, an acoustic coupling medium can be disposed between the external tissue surface 36 and the member 18. Examples of acoustic coupling mediums are disclosed in U.S. Patent Application Publication No. 2004/0234453 to Smith and U.S. Pat. No. 6,039,694 to Larson et al., both incorporated herein by reference in their entireties. Acoustic coupling mediums may include stand-offs and/or sheaths, which may contain a gel that can act as a heat sink for cooling and/or as a medium for energy transfer. The stand-offs and/or sheaths may be disposable. For example, a disposable condom-like sheath could be placed over the device end.

The individual transducer elements, 28 of ultrasound emitting member 18 may be individually controlled in a manner to interfere with one another such that the focal zone can be precisely controlled. For example, individual elements can be driven at the same frequency, but different phases and possibly different amplitudes to form a phased array transducer and focus the energy more exactly. The transducers may have varying focal lengths or frequencies at differing, converging angles. In one embodiment, a series of two or more transducers may be aimed at the same focal point but could be alternated on and off to reduce heat generation of the transducers and the tissue directly in front of them thus preventing near-field tissue necrosis. This on/off cycling technique would allow a lesion to be made more quickly without intermediate tissue damage. In one embodiment of the present invention, an ultrasound conductive cooling field may be created with a cooling liquid, for example, delivered between the transducer elements and the tissue.

Since the ultrasound is focused at focusing zones F, which may be spaced from one another, the ultrasound is of greater or higher intensity at focusing zones F than in tissue surrounding the focusing zones F. Ultrasound energy is thusly focused or concentrated at the focusing zones F, causing the tissue at the focusing zones F to be heated to an ablative temperature resulting in formation of lesions 38 at the focusing zones, respectively. The tissue is ablated at the lesions 38; and, as used herein, "ablated" tissue includes tissue that has been thermally damaged, altered, necrotized, denatured, destroyed, coagulated or cauterized. When all of the transducer elements 28 are actuated, as shown in FIG. 3, heating of tissue S will occur at a focusing zone F for each transducer element, resulting in formation of a lesion 38 at each focusing zone F. The cross-sectional size of the lesions will normally depend on the width of the focusing zones. However, depending on the intensity and duration of the ultrasound energy, the lesions 38 may "grow" or "spread" somewhat beyond the focusing zones due to thermal conduction causing the dispersal or spread of heat from the focusing zones. Therefore, depending on procedural parameters and the dimensions of the focusing zones, each lesion 38 has a predetermined or predictable cross-sectional size, i.e. length and width, as well as depth. As an example, each lesion 38 spreads radially outwardly somewhat from the corresponding focusing zone. The lesions 38 have a generally circular surface or cross-sectional configuration as shown in FIGS. 3 and 4 and a specific depth as shown in FIG. 3. Depending on procedural parameters, the dimensions of the focusing zones and/or the type of tissue being ablated, the lesions may or may not have a uniform cross-section along their depth. Where the focusing zones are sufficiently close together, and where the intensity of the ultrasound energy emitted from the transducer elements is sufficiently high and is applied to the tissue for a sufficient duration, the individual lesions may merge to form a single continuous lesion at the target area so that the target area is filled with ablated tissue. However, depending on the spacing between the focusing zones, and depending on the intensity of the ultrasound energy emitted from the transducer elements and the duration of ultrasound energy delivery to the tissue, the lesions 38 may remain separate, discrete and not connected to one another as shown in FIGS. 3 and 4 so that the target area 34 contains unablated tissue and the lesions 38 at which the tissue is ablated. FIG. 4 illustrates a lesion 38 formed in tissue S for each focusing zone F wherein the lesions 38 are disposed within the target area 34 but do not merge with, contact, overlap or abut one another. Rather, each lesion 38 is surrounded or circumscribed perimetrically by unablated tissue. The non-contacting lesions 38 and unablated tissue are contained in an ablated tissue area 35 at, coincident, coextensive or aligned with the target area 34.

When all of the transducer elements 28 are actuated, an ablated tissue area of specific surface or cross-sectional configuration and size is created within the tissue S for the transducer 24 in accordance with the configuration and size of the array, the intensity level of the emitted ultrasound energy, the duration or time of ultrasound energy delivery to the tissue, and the size of the lesions. Accordingly, an ablated tissue area having a specific cross-sectional length, width and depth is formed in the tissue, with the perimeter of the ablated tissue area circumscribing the array of lesions 38. FIGS. 3 and 4 illustrate, in dotted lines, the ablated tissue area 35 formed in tissue S when all of the transducer elements are actuated. The ablated tissue area 35 has a generally rectangular surface or cross-sectional configuration or area with a predetermined cross-sectional length and width shown in FIG. 4 and a predetermined cross-sectional depth, shown in FIG. 3, the cross-sectional depth corresponding to the depth of the lesions 38. When the ultrasound emitting member 18 is positioned on, against or adjacent the tissue S at a location aligned with a designated target area 34, the ablated tissue area 35 will be formed at or coincide with the target area as shown in FIGS. 3 and 4. The ablated tissue area is surrounded, bordered or circumscribed perimetrically by unablated tissue, as well as having unablated tissue above and below it. Since the focusing zones F begin the predetermined distance or the calculable or determinable distance below the tissue surface 36, the ablated tissue area 35 is an internal or subsurface ablated tissue area beginning the predetermined distance or the calculable or determinable distance beneath the tissue surface. Accordingly, the lesions 38 and ablated tissue area 35 begin at a beginning or starting margin 64 located the predetermined or calculable distance below the external tissue surface 36 and end at an ending margin 66 disposed further below the external tissue surface than the beginning margin, the distance between the beginning and ending margins corresponding to the depth of the lesions 38 and, therefore, the depth of the ablated tissue area 35.

The housing 26 can have various external configurations and sizes and can be formed by a portion of the transducer or can mount the transducer elements in various ways. The handle shaft 20 comprises an elongate, hollow or tubular member of sufficient length to position the ultrasound emitting member 18 at various operative sites in or on the body of a patient while the handle 22 is maintained at a remote location, typically externally of the patient's body. The handle shaft 20 could be solid and may comprise a bar or other shaped member. Preferably, the handle shaft 20 is malleable as disclosed in U.S. patent application Ser. No. 09/488,844, the disclosure of which is incorporated herein by reference. The handle 22 has a forward end coupled to the proximal end of handle shaft 20 and has a rearward end. The handle 22 preferably has a configuration to facilitate grasping by a surgeon or other operator. One or more controls or switches 42 may be provided on handle 22 to effect operation of the focused ultrasound ablation device. The line of focused energy F, may be aligned with the long axis of the entire device. Alternatively, the housing 26 may be attached to the handle shaft 20 such that housing 20 may be manually or remotely rotated such that the line of focused energy F, is perpendicular to the long axis of the device or some angle between perpendicular and parallel to the long axis of the device.

One or more electrical transmission wires 44 is/are connected to the transducer 24 and extend through the handle shaft 20 for connection with power supply 14 in order to transmit or supply electric current from the power supply to the transducer. The power supply may be disposed partly or entirely in the handle, or may be provided separately as a console or unit coupled to the handle shaft or the handle via one or more appropriate transmission wires, which may be the same or different from the one or more transmission wires 44. For example, an electrical cord of suitable length may be removably coupled between the handle 22 and the power supply 14. The power supply 14 can be designed in various ways as a source or supply of electricity to activate or excite transducer 24 to generate and emit ultrasound energy. For example, the power supply can be designed to provide high frequency alternating electrical current to the transducer via the one or more transmission wires. The power supply may include a single or multiple channel RF generator, with or without an amplifier, providing a current or voltage source to power the transducer(s). Electrical current provided by the power supply is selectively discharged into all or selected ones of the piezoelectric elements producing vibration of all or selected ones of the piezoelectric elements and, therefore, producing acoustic or ultrasonic waves or energy. The power supply may be separate from the handle but may be operated via controls 42 on the handle. In addition, the transducer assembly may incorporate air or liquid cooling circulation channels to remove excess internal heat generated during operation.

Each transducer element, 28 may have slightly different physical characteristics such as efficiency, focal zone, etc. that significantly affect performance. These variances can be compensated for by controller 16. The handle 22 may have incorporated within it, a memory chip that is capable of being read by controller 16. The memory chip may store transducer properties, such as power requirements, temperature requirements, number and/or type of transducers, type of device, number of allowed uses, reuse information, variation in device to device characteristics, etc. that were characterized and recorded during manufacture, assembly and/or use. The memory chip may store information delivered by controller 16. For example, the controller may deliver a date and time of use stamp to the memory chip and/or details about a procedure. The controller and/or memory chip may be used to prevent the use of the device for more times than desired or acceptable. One or more reuse prevention features may be incorporated into ablation system 10.

In the case of focused ultrasound ablation device 12, a transmission wire 44 is provided for each piezoelectric element and, therefore, for each transducer element. As shown in FIG. 3, each transmission wire 44 is connected to its corresponding piezoelectric element and to the power supply so that the transducer elements are individually driven by or supplied with current from the power supply. The transmission wires 44 are disposed in respective passages within the housing and may be disposed within a sheath or sleeve 46 extending through shaft 20. However, the transmission wires can be disposed externally of the housing and/or the shaft. The transmission wires 44 are connected to switches (not shown), respectively, for controlling the supply or transmission of current from the power supply 14 to the piezoelectric elements, respectively. The switches can be incorporated in the ultrasound emitting member 18, the power supply 14 and/or the controller 16.

The controller or control unit 16 controls the supply of power from power supply 14 to transducer 24 so that the transducer can be driven to deliver various intensity levels of ultrasound energy for various durations, periods or lengths of time. In particular, the controller 16 controls the supply of power from the power supply to the individual piezoelectric elements so that the transducer elements can be individually driven or actuated to emit ultrasound energy. The controller, which may be designed as part of the power supply, will typically include a control panel and display monitor, one or more switches for current control, an input mechanism such as a keyboard, and/or a microprocessor including memory, storage and data processing capabilities for performing various functions. The controller is capable of selectively activating the switches for the transducer elements to "fire" or effect actuation of all or selected ones of the plurality of transducer elements to emit ultrasound energy. For example, switches on the controller 16 and/or the controller keyboard can be used to selectively couple and decouple the individual transducer elements 28 with the electrical drive signal or current from the power supply 14.

Input to the controller 16 provided by the surgeon or other medical personnel determines the transducer elements 28 to be actuated. For example, data entered via the controller keyboard is used to identify the particular transducer elements to be actuated, the transducer elements being identified, for example, by their location or position in the array as explained above. In this manner, the switches of selected transducer elements can be activated to permit transmission of electrical current from the power supply to the piezoelectric elements of the selected transducer elements while the switches of other non-selected transducer elements can remain deactivated to prevent transmission of electrical current thereto when the power supply is actuated or switched to an "on" mode. It should be appreciated that various components and/or methodology can be incorporated in the device 12, the power supply 14 and/or the controller 16 to permit selective actuation of selected ones of the transducer elements 28 and that such components and/or methodology would be within the purview of one skilled in the art. In addition, the precise location to focus ablative energy can be determined by various imaging modalities such as ultrasound imaging, CT, MRI, PET, fluoroscopy, etc. The coordinates for the desired area of ablation from any of these imaging modalities can be electronically fed to controller 16 such that the desired ablation pattern can be generated and ablated. Two or three-dimensional imaging may be performed as well as phased or annular array imaging may be performed. For example, two or three-dimensional echocardiography, such as transesophageal echocardiography, or ultrasound imaging, such as transthoracic ultrasound imaging may be employed as described in U.S. Patent Application Publication No. 2005/0080469, the disclosure of which is incorporated by reference in its entirety.

Various transducers can be used in the methods of the present invention. The piezoelectric elements can be made of various piezoelectric materials such as PZT crystal materials, hard lead, zirconate/lead titanium, piezoelectric ceramic, or lithium-niobate piezoceramic material. The transducer elements can be of various sizes and can have various focusing geometries. The frequency ranges of the transducers can vary depending on clinical needs. Transducer frequencies may be in the range of 0.5 to 12 MHz and, more typically, in the range of 5 to 12 MHz. Preferably, the transducer frequency will allow thermal ablation of the tissue to be effected in response to the application or delivery of ultrasound energy to the tissue for a relatively short duration or length of time.

In accordance with the present invention, the duration or length of time for ultrasound energy delivery or application to the tissue preferably ranges from 2 to 60 seconds depending on desired lesion size and/or ablative effect.

In accordance with the methods of the present invention, high intensity focused ultrasound may used to create an ablated tissue area containing unablated tissue and a plurality of lesions at which the tissue is ablated.

As shown in FIG. 3, the ultrasound emitting member 18 is placed against the tissue S of a patient to position the active face 32 in contact with the external tissue surface 36. The active face is placed at or on the surface 36 at a location aligned with a desired target area 34 in the tissue for creation of an ablated tissue area, such location corresponding to an area of the tissue that is to be ablated. The shaft 20 may be grasped and manipulated, as necessary, to facilitate positioning of the active face at the desired location on the external tissue surface. Typically, the ultrasound emitting member will be placed in contact with tissue at a location where an ablation lesion is desired. Also, all or specific ones of the transducer elements are selected for actuation or "firing" in accordance with the desired size and configuration for the ablated tissue area and/or the desired number of lesions to be contained in the ablated tissue area. The ablation device 12 is programmed via the controller to effect actuation or "firing" of the selected transducer elements when electric current or a signal is supplied to the transducer. Of course, selection and programming for actuation or "firing" of selected transducer elements can be performed prior to positioning of member 18.

Once the active face is positioned at the desired location, the power supply is activated or switched to an "on" mode to transmit electrical energy to the previously selected transducer elements. In response thereto, the piezoelectric elements corresponding to the selected transducer elements vibrate and produce ultrasound energy, which is focused within the tissue S at the corresponding focusing zones F. In the procedure of FIG. 3, all of the transducer elements are "fired" to emit ultrasound energy, causing the tissue to be heated to an ablative temperature at a focusing zone for each transducer element. The tissue S at the focusing zones is heated to a temperature in the range of 50 to 90 degrees Celsius for the time required to achieve ablation or thermal damage in the tissue. The focusing zones are contained in the target area 34. The tissue S is heated at the focusing zones to a sufficiently high temperature so as to cause a plurality of subsurface or internal lesions 38 to be simultaneously formed in the tissue S while the ultrasound emitting member 18 remains external of and does not physically penetrate the tissue S.

Lesions 38 have a generally circular surface or cross-sectional configuration as shown in FIGS. 3 and 4 and do not contact or touch one another. Lesions 38 contain ablated or damaged tissue while the tissue surrounding each lesion 38 is not heated to the ablative or thermally damaging temperature and, therefore, is unablated or undamaged. In this manner, eighteen discontinuous or non-contacting individual lesions 38 are formed in the tissue as represented in FIG. 4. Lesions 38 are contained in the internal ablated tissue area 35 coincident with the target area 34, the ablated tissue area 35 containing the lesions 38 and the unablated tissue between adjacent lesions 38. The lesions 38 have a cross-sectional length and width and a depth of known parameters depending on the size and focusing geometry of the transducer elements, the intensity of the ultrasound energy, the temperature to which the tissue is heated and the duration of ultrasound energy delivery or application to the tissue.

Due to the predetermined distance and the known length for the focusing zones, the lesions 38 and, therefore, the ablated tissue area 35, begin at the beginning or starting margin 64 located a predetermined or known depth beneath or below the external tissue surface 36 and end at the ending margin 66 located a greater predetermined or known depth beneath the external tissue surface 36, the distance between the beginning and ending margins corresponding to the depth of the lesions and, therefore, the depth of the ablated tissue area 35. By selecting the appropriate focusing zone depth and treatment parameters, a desired thickness or depth of unablated or undamaged tissue between the beginning margin 64 and the external tissue surface 36 is disposed outside the ablated tissue area. Preferably, the beginning margin is located 50 to 150 micrometers below the external tissue surface. In the method of FIGS. 3 and 4, a layer of unablated tissue about 100 micrometers thick is maintained between the external tissue surface 36 and the beginning or starting margin 64 of the lesions 38. The lesions 38 have a depth of 50 to 150 micrometers and, preferably, a depth of about 100 micrometers, in the direction perpendicular to tissue surface 36 such that the ablated tissue area and the lesions terminate or end at the ending margin 66 disposed a depth of about 200 micrometers beneath the external tissue surface 36 at the transducer/tissue interface. Accordingly, there is a perpendicular distance of about 200 micrometers from the external tissue surface to the ending margin of the ablated tissue area. By selecting the appropriate focusing zone length and treatment parameters, the depth of the ending margin 66 within the tissue is controlled.

As shown in FIG. 4, the ablated tissue area 35, which is surrounded above, below and perimetrically by unablated or undamaged tissue, has a surface or cross-sectional configuration or area of generally rectangular shape with a cross-sectional width and length varying from 3 mm to 50 mm in either dimension, i.e. 3 mm×3 mm to 50 mm×50 mm or in between, depending on the size of the area to be treated. Although the cross-sectional length and width or other external dimensions of the ablated tissue area can be determined by the locations of the "fired" transducer elements, it should be appreciated that the cross-sectional length and/or width of the ablated tissue area can alternatively be obtained by moving the member 18 along the tissue as described in U.S. patent application Ser. No. 09/487,705, the disclosure of which is incorporated herein by reference.

Depending on the desired lesion size and/or thermal effect, ultrasound energy may be delivered or applied to the tissue for a duration in the range of 2 to 60 seconds. The emission of ultrasound energy by ultrasound emitting member 18 is terminated by the surgeon or other operator once lesions of desired size or a desired amount of tissue ablation has been obtained, and the member 18 is removed. In order to terminate the emission of ultrasound energy by the ultrasound emitting member, the power supply is deactivated or switched to an "off" mode so that electrical current is no longer supplied to the selected piezoelectric elements.

Figure 5:
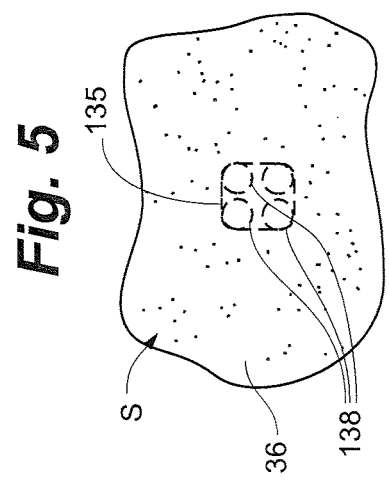
FIG. 5 is a broken top view illustrating the surface or cross-sectional configuration of an alternative ablated tissue area created in the tissue.

FIG. 5 is representative of a single treatment procedure in accordance with the present invention wherein a subsurface ablated tissue area 135 containing four non-contacting lesions 138 is formed. The ablated tissue area 135 is similar to ablated tissue area 35 except that it is of generally square surface or cross-sectional configuration or area and contains four generally circular lesions 138 each surrounded by unablated tissue. The ablated tissue area 135 can be formed using the ultrasound emitting member 18 by selecting and "firing" transducer elements R1C1, R1C2, R2C1 and R2C2, for example, to emit ultrasound energy. As described for the procedure illustrated in FIGS. 3 and 4, the ultrasound energy emitted by the selectively "fired" or actuated transducer elements is focused in the tissue at a focusing zone for each actuated transducer element, causing subsurface lesions 138 to be formed in the tissue at the focusing zones corresponding to transducer elements R1C1, R1C2, R2C1 and R2C2. The lesions 138 are similar to lesions 38 but are larger in diametric cross-sectional size than lesions 38. The ablated tissue area 135 is surrounded by unablated tissue above, below and perimetrically.

Figure 6:
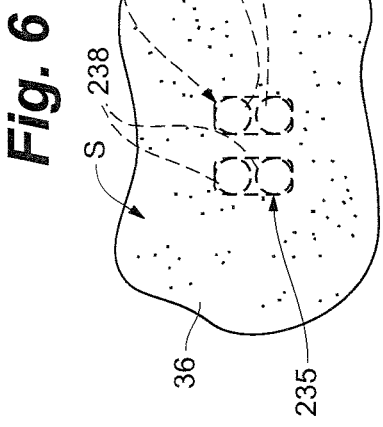
FIG. 6 is a broken top view illustrating the surface or cross-sectional configuration of a plurality of further alternative ablated tissue areas created in the tissue.

FIG. 6 is representative of a multiple treatment procedure in accordance with the present invention wherein a plurality of internal ablated tissue areas 235, each containing unablated tissue and a plurality of lesions 238, are formed or created in the tissue S. The ablated tissue areas 235 are spaced from one another, and each contains two generally circular lesions 238 similar to lesions 138 except that lesions 238 have a slightly larger cross-sectional diameter than lesions 138. The lesions 238 of each ablated tissue area 235 are spaced slightly from one another and are surrounded by unablated tissue so as to be non-contacting. Each ablated tissue area 235 has a surface or cross-sectional configuration or area of generally rectangular shape. The ablated tissue areas 235, which are similar to ablated tissue area 35 except for their cross-sectional configuration, can be formed using member 18 as described above by actuating an appropriate pair of transducer elements. The ablated tissue areas 235 are typically formed in separate treatments performed at different times. However, it should be appreciated that a plurality of ablated tissue areas, such as ablated tissue areas 235, can be formed in the tissue during a single procedure performed at one time.

FIG. 7 illustrates in dotted lines an ablated tissue area 335 of rectangular cross-sectional configuration formed in the tissue S and containing six generally circular non-contacting lesions 338 each surrounded by unablated tissue. The lesions 338 and ablated tissue area 335 are similar to the lesions 38 and ablated tissue area 35 except for the cross-sectional size of lesions 338 being different from the cross-sectional size of lesions 38. The ablated tissue area 335 will typically be formed in a single treatment or procedure. The ablated tissue area 335 can be formed using the ultrasound emitting member 18 by actuating six appropriate transducer elements.

Figure 8:
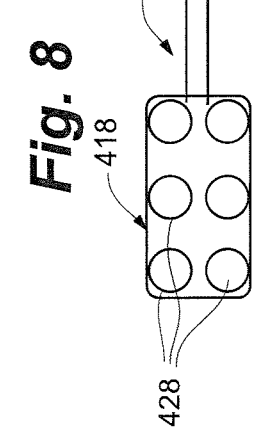
FIG. 8 is a broken bottom view of an alternative focused ultrasound ablation device having a modified ultrasound emitting member for use in the methods of the present invention.

It should be appreciated that the methods of tissue ablation according to the present invention can be performed using focused ultrasound ablation devices wherein the transducer elements of the ultrasound emitting members are not selectively actuatable. For example, FIG. 8 illustrates an alternative focused ultrasound ablation device 412 having focused ultrasound emitting member 418, which is similar to focused ultrasound emitting member 18 except that focused ultrasound emitting member 418 includes an array of six transducer elements 428 actuatable simultaneously or in unison to emit ultrasound energy. The transducer elements 428 are arranged in two rows and three columns and are used to form an ablated tissue area containing six lesions, such as ablated tissue area 335. Accordingly, it should be appreciated that various dedicated ultrasound emitting members having different arrays and/or numbers of transducer elements can be provided, with a particular ultrasound emitting member being capable of obtaining a particular ablated tissue area of predetermined size, configuration and number of lesions in response to actuation of all of the transducer elements of the particular ultrasound emitting member.

Figure 9:
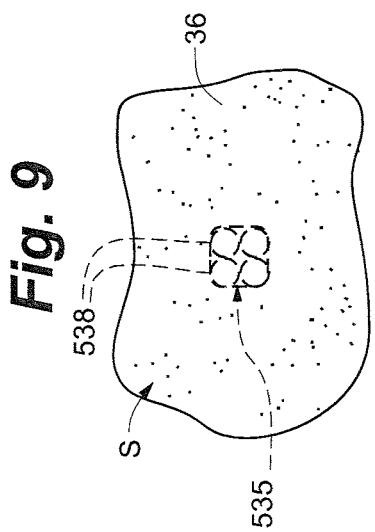
FIG. 9 is a broken top view illustrating the surface or cross-sectional configuration of an additional alternative ablated tissue area formed in the tissue.

FIG. 9 illustrates an alternative, subsurface ablated tissue area 535 formed in the tissue S in a manner similar to ablated tissue area 135. However, the ultrasound energy used to form ablated tissue area 535 is of higher intensity and/or is applied to the tissue for a longer duration than the ultrasound energy used to form ablated tissue area 135. Accordingly, the lesions 538 of ablated tissue area 535 have a generally circular surface or cross-sectional configuration larger in diameter than the generally circular cross-sectional configuration of lesions 138 due to greater dispersal of heat from the focusing zones. As a result, the lesions 538 contact or touch one another but still do not merge sufficiently to fill the entire ablated tissue area 535 with ablated tissue. Although each lesion 538 is not completely surrounded perimetrically by unablated tissue, there is still some unablated tissue within the ablated tissue area 535 as shown in FIG. 9 by unablated tissue disposed between adjacent lesions 538. It should be appreciated, therefore, that the ablated tissue areas formed in accordance with the present invention can include a plurality of non-contacting lesions each completely surrounded by unablated tissue and/or a plurality of contacting lesions with unablated tissue between the contacting lesions.

In the procedures described and illustrated above, the ultrasound emitting member is placed against the tissue at a desired location to form an ablated tissue area of final size and configuration in the tissue with focused ultrasound energy generated and emitted by the ultrasound emitting member without moving the ultrasound emitting member from the desired location. It should be appreciated, however, that where the largest size ablated tissue area capable of being formed in the tissue with the ultrasound emitting member is smaller than the final size and/or different from the final configuration desired for the ablated tissue area, the ultrasound emitting member can be moved along to form an ablated tissue area of desired final size and configuration as explained in U.S. patent application Ser. No. 09/487,705.

The methods of the present invention allow tissue ablation to be performed with minimal trauma and pain for the patient and with faster healing and recovery times. By controlling the delivery of ultrasound energy to the tissue, the temperature to which the tissue is heated by the ultrasound energy can be controlled to avoid undesired patient responses. The ultrasound emitting members can be provided with sensors for monitoring the amount of ultrasound energy delivered to the tissue and/or for detecting the temperature to which the tissue is heated, which can be provided as feedback to the controller. The delivery of ultrasound energy to tissue can be controlled to achieve a selected temperature, a selected amount of ablation, a desired lesion size or a desired duration of ultrasonic energy delivery. The transducer assembly can contain ultrasound imaging transducers that can be used to provide a real-time or multiplexed echo feedback on the progress of the ablation, in particular, the changes in mechanical properties of the tissue that are observed in eco imaging. This imaging can also be used to guide the steering and focus depth of the transducers energy focus to ensure that the desired target tissue is indeed being ablated. Furthermore, the ultrasound transducer may sense reflections from the targeted tissue such as backscatter echo and spatial compound imaging, etc. to estimate the thermal dose, tissue temperature and/or necrosis. The ultrasound emitting members can be disposable or can be designed to be reusable and thusly can be capable of being sterilized to medical standards. The ultrasound emitting members can be provided with disposable covers or guards which can be removed and discarded after use so that the ultrasound emitting members can be reused. The transducer or transducer elements can be removable from the ultrasound emitting members allowing disposability of the ultrasound emitting members and reuse of the transducer or transducer elements in another ultrasound emitting member. The ultrasound emitting members can be immobilized during use as may be accomplished with various types of stabilizing members provided on the shafts or on the ultrasound emitting members. The focused ultrasound ablation devices can be provided with imaging capabilities or can be used with various imaging devices as disclosed in U.S. patent application Ser. No. 09/487,705. The focused ultrasound ablation devices can be provided with cooling systems for cooling the ultrasound emitting members and/or the transducers as disclosed in U.S. patent application Ser. No. 09/487,705. The methods of tissue ablation can be performed using an acoustic coupling medium as disclosed in U.S. patent application Ser. No. 09/487,705. A single ultrasound emitting member can be used to form various different ablated tissue areas of various sizes, configurations, and number of lesions depending on the particular transducer elements selected for actuation. A plurality of different ultrasound emitting members having non-selectively actuatable transducer elements can be provided with each ultrasound emitting member having a different array and/or number of transducer elements to obtain a particular ablated tissue area of predetermined size, configuration and number of lesions when all of the transducer elements of the ultrasound emitting members are actuated. Any number of ablated tissue areas can be formed with each ablated tissue area surrounded by unablated tissue or with the ablated tissue areas contiguous to, in abutment with, contacting or overlapping one another to form a single ablated tissue area. The ultrasound emitting members, the transducers and/or the transducer elements can be moved relative to the tissue to scan target areas with focused ultrasound energy, and such scanning can be accomplished in various diverse ways. The ablated tissue areas can include unablated tissue and a plurality of non-contacting lesions, a plurality of contacting lesions or a combination of contacting and non-contacting lesions. Any number of lesions can be contained in the ablated tissue areas including even and odd numbers of lesions.

In one embodiment of the present invention, a hand-held probe having one or more HIFU transducers may be used to create epicardial lesions, for example, by dragging the device across the epicardial surface of the heart. In an alternative embodiment of the present invention, a trans-esophageal ablation device having one or more HIFU transducers may be used to create tissue lesions, for example, by placing the device in a patient's esophagus and ablating cardiac tissue. In another alternative embodiment of the present invention, a trans-tracheal ablation device having one or more HIFU transducers may be used to create tissue lesions, for example, by placing the device in a patient's trachea.

FIG. 10 shows diagrammatically a two-dimensional view of the two atria of a human heart, in which transmural lesions of a Maze procedure are indicated by reference letter C, the undisturbed electrical impulses by A, and the blocked electrical impulses by B. The lesions C are in the nature of scar tissue. One or more lesions C may be formed during an ablation procedure. The atria, as viewed epicardially from a lower aspect, include the left atrium 100 and the right atrium 101. Structural features of the atria include the bases of the pulmonary veins 110, the inferior vena cava 120, the superior vena cava 130, the left atrial appendage 140 and the right atrial appendage 150. A first lesion 160 is a curved lesion that is joined end-to-end such that it encircles the pulmonary veins 110, and is between the pulmonary veins 110 and conductive pathways in the left atrium 100 and between the pulmonary veins 110 and conductive pathways in the right atrium 101. A second lesion 165 extends between the superior vena cava 130 and the inferior vena cava 120 and blocks a first conductive pathway 167. A third lesion 170 extends across the left atrium 100 from an intersection 171 with a portion of the first lesion 160 toward the left atrial appendage 140 and blocks a second conductive pathway 172. A fourth lesion 175 extends along the right atrium 101 laterally from an intersection 176 with a portion of the second lesion 165 to the annulus of the tricuspid valve (not shown). A fifth lesion 180 extends from an intersection 181 with a portion of the first lesion 160 along the left atrium 100 to the annulus of the mitral valve (not shown) and blocks a third conductive pathway 182. A sixth lesion 185 extends along the right atrium 101 toward the right atrial appendage 150. Incisions 142 and 152 correspond to where the atrial appendages may be excised. Sutures may be used to close the incisions 142 and 152. Alternatively, incisions 142 and 152, or portions thereof, may be ablation lesions. One or more of the lesions discussed above may be created according to one or more embodiments of the present invention. For further details regarding the lesion pattern shown in FIG. 10, see U.S. Pat. No. 6,165,174, the disclosure of which is incorporated herein by reference. In addition, U.S. Pat. No. 6,807,968, the disclosure of which is incorporated herein by reference, also discloses the lesion pattern of a Maze ablation procedure.

In one embodiment of the present invention, ablation device 12 may be used to create a right atrial flutter lesion that extends from the tricuspid valve to the coronary sinus. In another embodiment of the present invention, ablation device 12 may be used to ablate the SA and/or AV nodes. In another embodiment of the present invention, ablation device 12 may be used to form the Wolf-Parkinson-White ablation procedure. In another embodiment of the present invention, ablation device 12 may be used to isolate the four pulmonary veins by forming a single lesion encircling of all four veins (as shown in FIG. 10). Alternatively, ablation device 12 may be used to isolate a first pair of pulmonary veins by forming a lesion encircling two of the four veins. In addition, ablation device 12 may be used to isolate the second pair of pulmonary veins by forming a lesion encircling the remaining two veins. The two encircling lesions may then be connected with a connecting lesion placed in between the two lesions, which connect the two encircling lesions together. In another embodiment of the present invention, ablation device 12 may be used to isolate each pulmonary vein individually by forming four separate lesions encircling each of the four veins. Connecting lesions may also be formed connecting the four separate lesions together, if desired.

FIG. 11 shows a schematic view of one embodiment of a system 900 for ablating tissue while positioning, manipulating, holding, grasping, immobilizing and/or stabilizing tissue in accordance with the present invention. In this embodiment, system 900 is shown to comprise tissue-engaging device 200, a suction source 300, a fluid source 400, a HIFU ablation assembly 10, a sensor 600 and an imaging device 800. The HIFU ablation assembly 10 includes a focused ultrasound ablation or stimulation device 12, a power supply 14 and a controller 16. System 900 may also include a drug delivery device, a guidance device and/or a nerve and/or cardiac stimulation device (all not shown in FIG. 11). The tissue-engaging device may comprise one or more suction or vacuum ports, openings, orifices, channels or elements positioned on, along, within or adjacent a tissue contact surface. The suction ports, openings, orifices, channels or elements may communicate suction through the tissue contact surface to the atmosphere to engage or grasp tissue via suction. The drug delivery device may be used to deliver drugs and/or biological agents to a patient. The imaging device may be used to illuminate a surgical site. The imaging and guidance devices may be used to help control and guide the HIFU device.

In one embodiment of the present invention, the tissue-engaging device may comprise one or more mechanical means for engaging and/or grasping tissue. For example, the tissue-engaging head may comprise one or more hooks, clamps, screws, barbs, sutures, straps, tethers and/or staples. The tissue-engaging device may comprise a cuff or basket-type device designed to fit completely or partially around an organ, e.g., a heart. The tissue-engaging device may comprise one or more chemical means for engaging and/or grasping tissue. For example, the tissue-engaging device may comprise tissue glue or adhesive. The tissue-engaging device may comprise one or more coupling means for engaging and/or grasping tissue. For example, a suction means in addition to a mechanical means may be used to engage or grasp tissue. A magnetic means may also be used to engage or grasp tissue.

In one embodiment of the present invention, the tissue-engaging device may include a sufficiently resiliently flexible head that may be flexed to allow it to be pushed through a small incision, cannula or port. Once inside the chest cavity, the flexible head will return to its original shape. For example, the head may be configured to be collapsable for entering into a thoracic cavity through a small incision, cannula or port in endoscopic and/or closed chest surgery. In addition, to closed chest surgery, this invention is applicable to open chest/split sternum surgery, in particular open chest, beating heart surgery for repositioning the heart to improve access to various locations of the heart.

The tissue-engaging device may include one or more fluid openings for delivery and/or removal of one or more fluids. The tissue-engaging device may include needles for injection of fluids, drugs and/or cells into organ tissue. The tissue-engaging device may comprise a catheter or cannula for blood removal or delivery into an organ, e.g., a heart. In the case of the heart, the cannula or catheter may be placed through the wall of the heart and into an interior chamber of the heart comprising blood, for example, into the left ventricle. Blood may be removed or delivered via a blood pump. For example, a catheter or cannula of the tissue-engaging device may be attached to a CPB circuit or a cardiac assist circuit such as an LVAD circuit. The tissue-engaging device may include one or more openings for delivery or removal of one or more gases including smoke evacuation.

One or more parts or portions of the tissue-engaging device may be designed to be implantable. For example, following an ablation procedure, a head portion of the tissue-engaging device may be left within the patient, thereby providing benefit to the patient. The tissue-engaging head may be made of one or more biodegradable materials, thereby allowing the head to be absorbed by the patient over time.

The tissue-engaging device may comprise a maneuvering or support apparatus or means such as a shaft, a handle or an arm connected to a tissue-engaging head to position the head to thereby position or hold tissue such as the heart. The tissue-engaging head of the tissue-engaging device may be rigidly, permanently, moveably, or removeably coupled, connected or mounted onto the maneuvering or support apparatus or means. The support shaft, handle or arm may be rigid, flexible, telescoping or articulating. The shaft, handle or arm may comprise one or more hinges or joints for maneuvering and placing the device against tissue. The hinges or joints of the maneuvering or support apparatus may be actuated remotely, for example with pull wires, from outside a patients body. The shaft, handle or arm may be malleable or shapeable. The maneuvering or support means may be made of a shape memory alloy wherein heat may be use to change the shape of the maneuvering or supporting means.

In one method of the present invention, the medical procedure may include the use of a tissue-engaging device as described, for example, in U.S. patent application Ser. No. 10/643,299, U.S. Patent Application Publication No. 2004/0138522 and U.S. Pat. No. 6,447,443, the disclosures of which are incorporated herein by reference, in combination with one or more focused ultrasound ablation devices. The combination of one or more tissue-engaging devices and one or more tissue ablation devices may be used to position and ablate tissue, e.g., endocardial, myocardial and/or epicardial tissue of the heart, located within a body cavity, e.g., the thoracic cavity. Other body organ tissue, such as the liver, lungs or kidney, may also be positioned and ablated. An ablation procedure that utilizes a tissue-engaging device may be an open chest procedure, a closed chest procedure, a minimally invasive procedure, a beating heart procedure, and/or a stopped heart procedure. The tissue-engaging device may be positioned and used, for example, through a sternotomy, through a thoracotomy that avoids the sternal splitting incision of conventional cardiac surgery, through a mini-thoracotomy, through a sub-xyphoid incision, percutaneously, transvenously, arthroscopically, endoscopically, for example, through a percutaneous port, through a stab wound or puncture, through a small or large incision, for example, in the chest, in the groin, in the abdomen, in the neck or in the knee, or in combinations thereof. The tissue-engaging device may be guided into a desired position using various imaging and/or guidance techniques, e.g., fluoroscopic guidance techniques.

Tissue-engaging device 200 may be used to grasp and position the pericardium away from the surface of the heart thereby creating space between the surface of the heart and the pericardium. This type of procedure may be termed "tenting". Tissue-engaging device 200 may be used to grasp and position a heart away from a rib cage, for example in an endoscopic procedure, thereby creating space for a surgeon to work between the heart and the rib cage. Tissue-engaging device 200 may be used to grasp and position a heart away from other adjacent or nearby organs thereby creating space for a surgeon to work.

An endoscope or thoracoscope may be used to view on or more aspects of the medical procedure. Incisions may be maintained open by insertion of a cannula or port through the incision so that instruments, such as a tissue-engaging device and/or HIFU ablation device, can be advanced through the lumen of the cannula or port. If a trocar is used, a trocar rod is inserted into the trocar sleeve, and the sharpened tip of the trocar rod is advanced to puncture the abdomen or chest to create the incision into the thoracic cavity. The trocar rod is then withdrawn leaving the trocar sleeve in place so that one or more surgical instruments may be inserted into the thoracic cavity through the trocar sleeve lumen.

In one embodiment of the invention, the surgeon may decide to stop the heart. For example, a series of catheters may be used to stop blood flow through the aorta and to administer cardioplegia solution. A closed chest, stopped heart procedure may utilize groin cannulation to establish cardiopulmonary bypass (CPB) and an intra-aortic balloon catheter that functions as an internal aortic clamp by means of an expandable balloon at its distal end used to occlude blood flow in the ascending aorta. A full description of one example of an endoscopic technique is found in U.S. Pat. No. 5,452,733, the disclosure of which is incorporated herein by reference.

Figure 12:
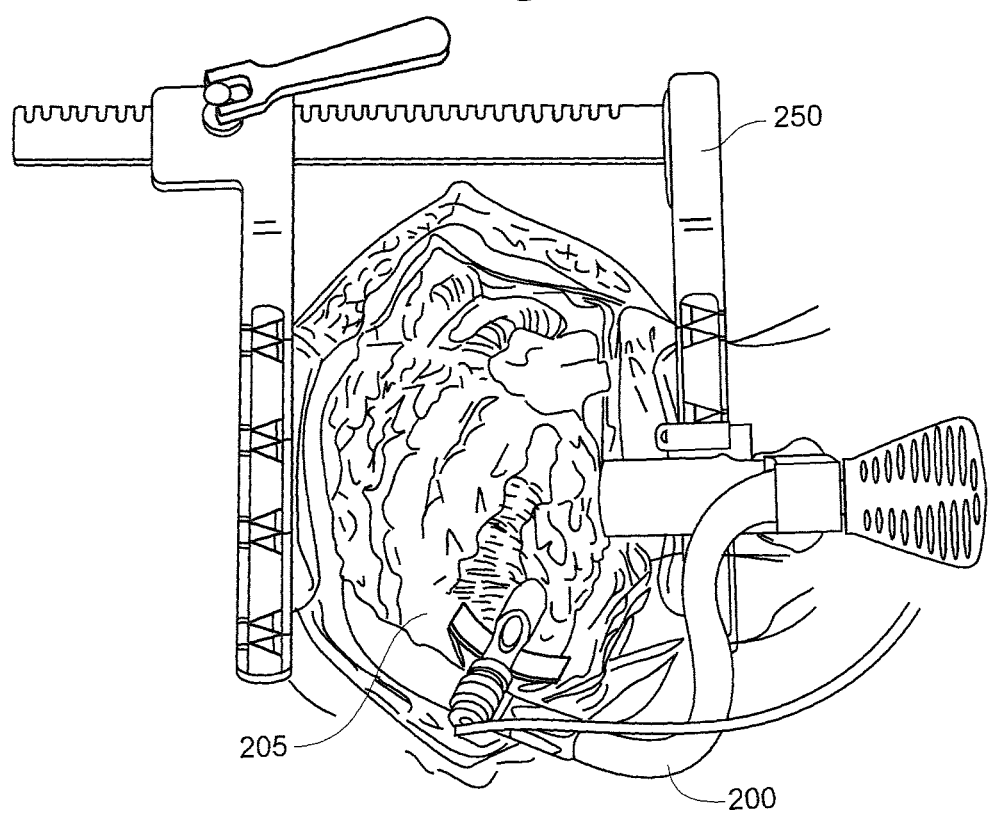
FIG. 12 is an illustration of one embodiment of a medical device in use in accordance with the present invention.
Figure 13:
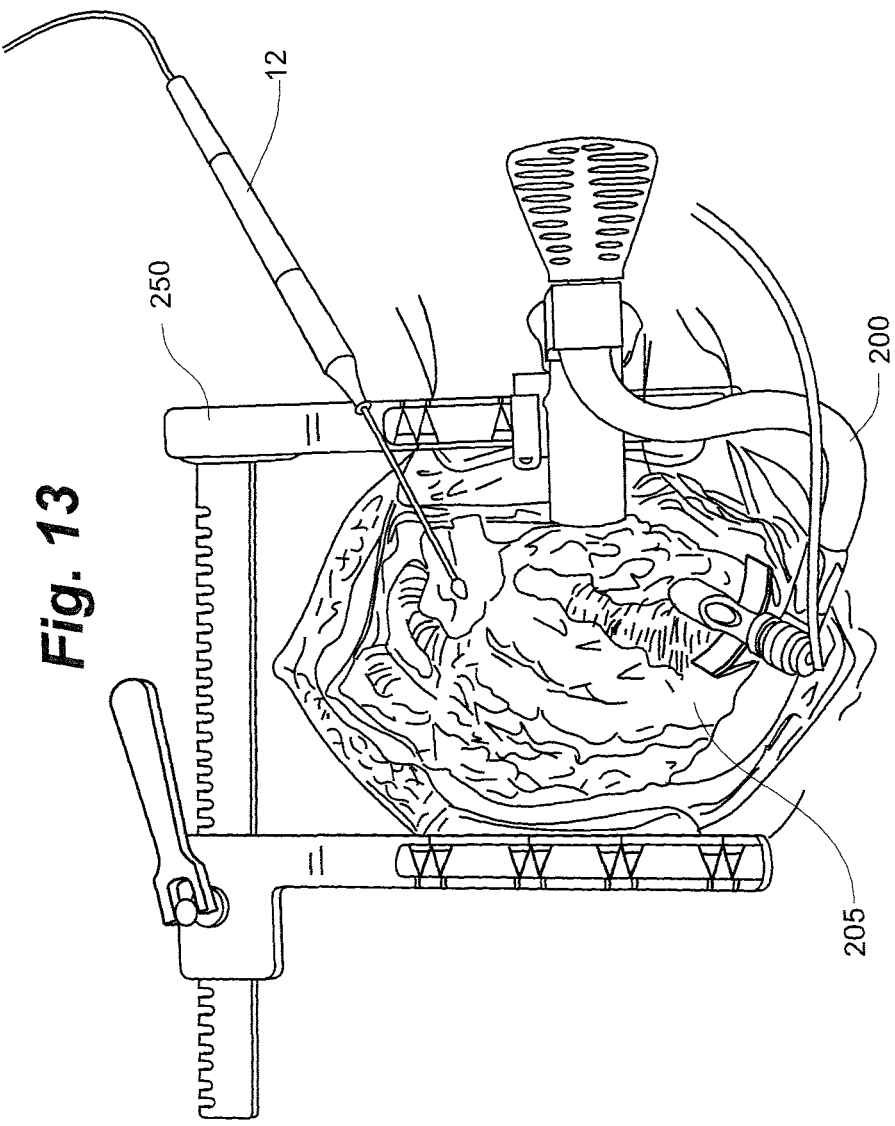
FIG. 13 is an illustration of one embodiment of a medical device in use in accordance with the present invention.

The tissue-engaging device may be used to position, manipulate, hold, grasp, immobilize and/or stabilize an area of tissue and/or an organ, such as a heart, during an ablation procedure. For example, the tissue-engaging device may be used to engage an area of tissue, such as an organ, and position the area of tissue or organ into a non-physiological orientation. For example, the tissue-engaging device 200, shown in FIG. 12, is shown being used in an open chest, sternotomy procedure to position the heart into a non-physiological orientation, thereby creating access to areas of the heart that an ablation device positioned, for example, through the chest opening or sternotomy would not have had ablative access to prior to positioning of the heart. FIG. 12 shows tissue-engaging device 200 locked onto a sternal retractor 250 fixed to a patient's chest. In FIG. 12, tissue-engaging device 200 is shown supporting a patient's heart 205 while it is engaged or attached to the apex of the patient's heart. The patient's heart may be beating or stopped. As shown in FIG. 13, a hand-held ablation device 12 positioned through a sternotomy and having at least one HIFU transducer may be used to create one or more epicardial lesions, for example, by moving or dragging the device across the epicardial surface of the heart. As shown in FIG. 13, the one or more epicardial lesions may be made while the heart is positioned in a non-physiological orientation.

Figure 14:
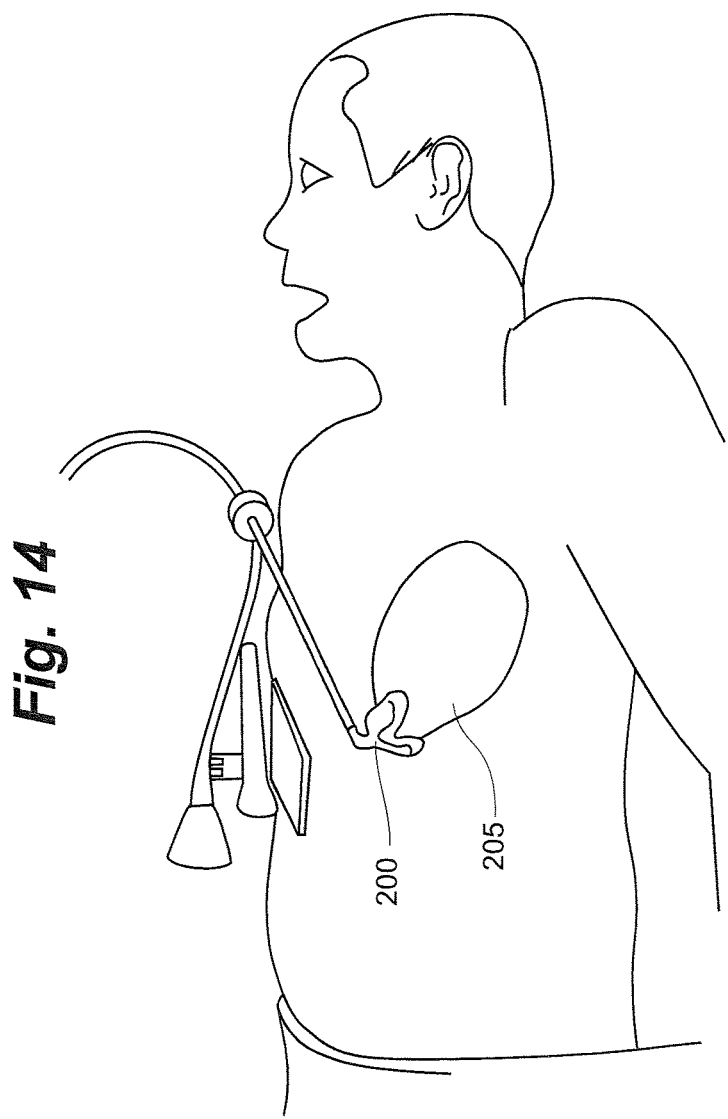
FIG. 14 is an illustration of one embodiment of a medical device in use in accordance with the present invention.

The tissue-engaging device 200, shown in FIG. 14, is shown being used in a closed chest, non-sternotomy procedure to position the heart 205 into a non-physiological orientation. Positioning the heart in a non-physiological can create access to areas of the heart that an ablation device positioned, for example, through a thoracotomy or port, through the patient's esophagus or trachea, or positioned outside the chest would not have had ablative access to prior to positioning of the heart.

In one method of the present invention, a focused ultrasound ablation device 12 is placed within the trachea and/or bronchi of the lungs to ablate tissue within the thoracic cavity of a patient. The ultrasound ablation device is sized and shaped to fit within the trachea and/or bronchi of the lungs. Shaft 20 may be of a sufficient length to allow insertion of an appropriately sized ultrasound emitting member 18 into the trachea and/or bronchi of the lungs of a patient through the patient's oral cavity. Once placed in the desired position, ultrasound energy may be focused through the wall of the trachea or bronchi and into tissue to be ablated. To ablate tissue not positioned within the focusing range of the ultrasound ablation device, a tissue-engaging device, as described earlier, may be used to move and position tissue of interest within the focusing range of the ablation device. The tissue-engaging device may be used to position tissue prior to an ablation procedure, during an ablation procedure and/or following an ablation procedure. A variety of tissue types and/or organs may be ablated or treated by one or more ultrasound ablations device placed within the trachea and/or bronchi of the lungs. Alternatively, a variety of tissue types and/or organs may be ablated or treated by one or more ultrasound ablation devices positioned through one or more other body cavity openings of the patient and/or positioned on the skin of the patient. For example, one or more ultrasound ablation devices may be positioned through the mouth, the nose, the anus, the urethra and/or the vagina. The ablation procedure may include one or more imaging methods or devices.

Figure 15:
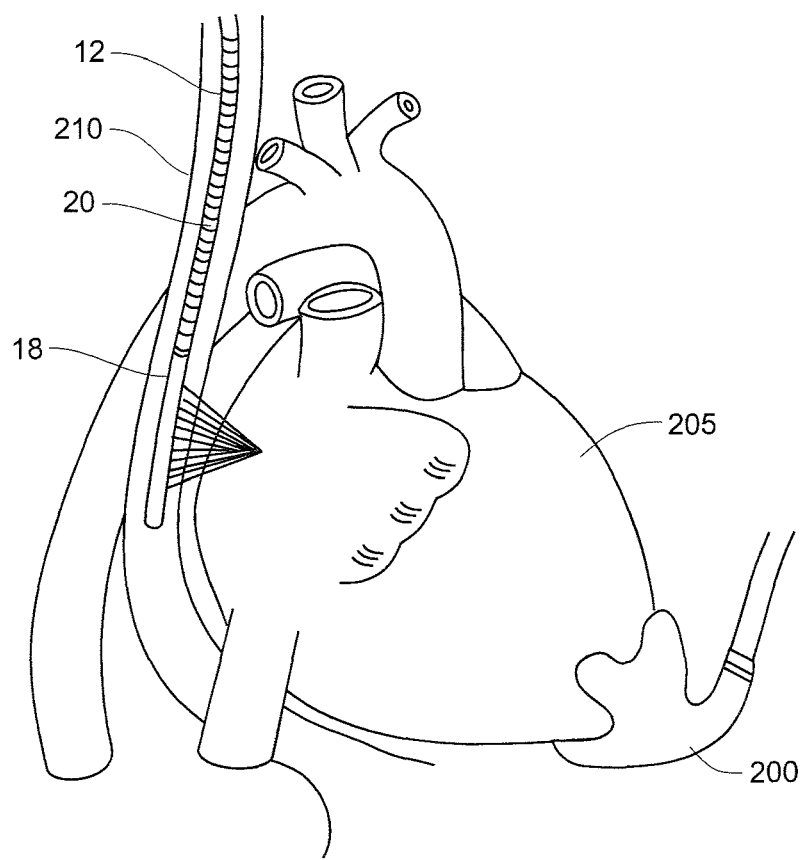
FIG. 15 is an illustration of one embodiment of a medical device in use in accordance with the present invention.

In one method of the present invention, see FIG. 15, a focused ultrasound ablation device 12 is placed within the esophagus 210 to ablate tissue of the heart 205, for example, in a Maze procedure. The ultrasound ablation device may be sized and shaped to fit within the esophagus 210. Shaft 20 may be of a sufficient length to allow insertion of an appropriately sized ultrasound emitting member 18 into the esophagus of a patient through the patient's oral cavity. Once placed in the desired position, ultrasound energy may be focused through the wall of the esophagus and into cardiac tissue to be ablated. Cardiac tissue is then ablated. To ablate cardiac tissue not positioned within the focusing range of the ultrasound ablation device, a tissue-engaging device 200, as described earlier, may be used to move and position the heart to move tissue of interest within the focusing range of the ablation device. The tissue-engaging device 200 may be used to position tissue prior to an ablation procedure, during an ablation procedure and/or following an ablation procedure. In addition to cardiac tissue, other tissue types and/or organs may be ablated or treated by one or more ultrasound ablation devices placed within the esophagus of the patient.

In one embodiment of the invention, ablation device 12 may comprise, for example, one or more inflatable and/or compressible members, which may be inflated or decompressed with air or liquid, for example, while the device is positioned within a body cavity to press the surface of the ablating member 18 firmly against the body cavity wall. For example, device 12 may comprise a balloon, which may be inflated with air or liquid while the device is positioned within the esophagus, the trachea and/or bronchi of the lungs to press the surface of the ablating member 18 firmly against the body cavity wall.

Figure 16:
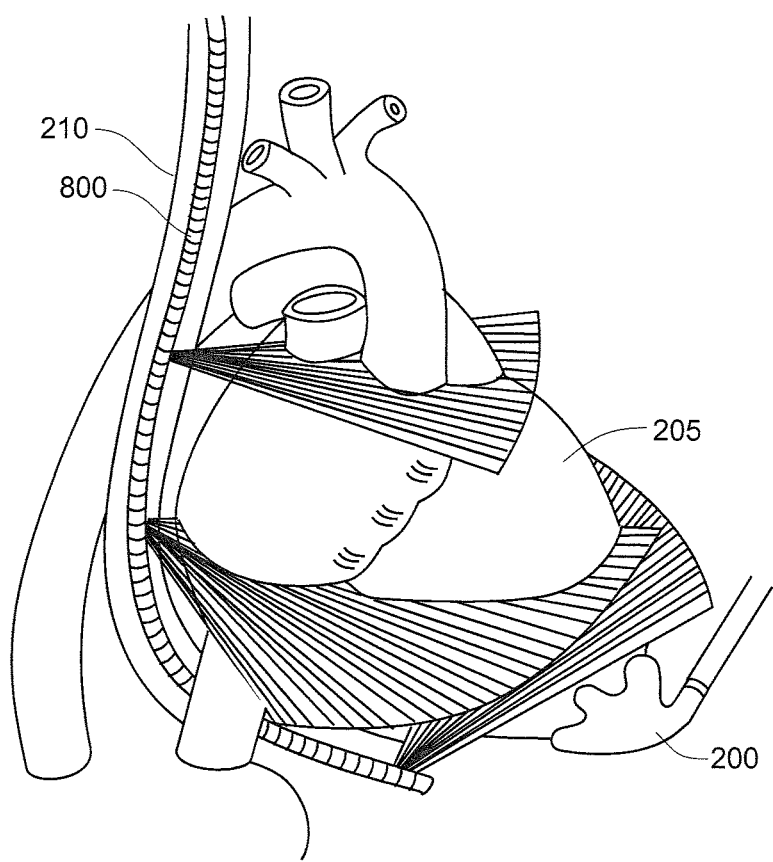
FIG. 16 is an illustration of one embodiment of a medical device in use in accordance with the present invention.

In one method of the present invention, an imaging device 800 may be used to image tissue such as heart tissue as shown in FIG. 16. The imaging device may be appropriately sized to allow its placement within the esophagus of the patient. Alternatively, the imaging device may be appropriately sized to allow its placement within the trachea and/or bronchi of the lungs of the patient. Alternatively, one or more imaging devices may be positioned through one or more other body cavity openings of the patient and/or positioned on the skin of the patient. For example, one or more imaging devices may be positioned through the mouth, the nose, the anus, the urethra and/or the vagina. In one embodiment of the present invention, ablation system 10 may include one or more imaging capabilities. For example, ultrasound imaging capabilities may be incorporated into ultrasound ablation device 12 so that a single device could be used to both image and ablate tissue. Once placed in the desired position, for example in the esophagus, ultrasound energy may be focused through the wall of the esophagus and into cardiac tissue to be imaged. Cardiac tissue is then imaged and the location of tissue to be ablated is determined. To image cardiac tissue not positioned within the focusing range of the imaging device, a tissue-engaging device 200, as described earlier, may be used to move and position the tissue of interest within the focusing range of the imaging device. The tissue-engaging device 200 may be used to position tissue prior to an imaging procedure, during an imaging procedure and/or following an imaging procedure. In addition to cardiac tissue, other tissue types and/or organs may be positioned and imaged by one or more positioning and imaging devices. In one embodiment of the present invention, the positioning or tissue-engaging device may comprise one or more imaging capabilities, e.g., ultrasound imaging.

In one embodiment of the present invention, a nerve stimulator comprising one or more nerve stimulation electrodes may be used to stimulate the patient's vagal nerve to slow or stop the patient's heart during an ablation procedure. The patient may be given one or more drugs to help stop the beating of the heart and/or to prevent "escape" beats. Following vagal stimulation, the heart may be allowed to return to its usual cardiac rhythm. Alternatively, the heart may be paced, thereby maintaining a normal cardiac output. Vagal stimulation, alone or in combination with electrical pacing and/or drugs, may be used selectively and intermittently to allow a surgeon to perform an ablation procedure on a temporarily stopped heart. For example, stimulation of the vagus nerve in order to temporarily and intermittently slow or stop the heart is described in U.S. Pat. No. 6,006,134, U.S. Pat. No. 6,449,507, U.S. Pat. No. 6,532,388, U.S. Pat. No. 6,735,471, U.S. Pat. No. 6,718,208, U.S. Pat. No. 6,228,987, U.S. Pat. No. 6,266,564, U.S. Pat. No. 6,487,446 and U.S. patent application Ser. No. 09/670,370 filed Sep. 26, 2000, Ser. No. 09/669,961 filed Sep. 26, 2000, Ser. No. 09/670,440 filed Sep. 26, 2000. These patents and patent applications are incorporated herein by reference in their entireties.

Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present invention may include various electrodes, catheters and electrode catheters suitable for vagal nerve stimulation to temporarily stop or slow the beating heart alone or in combination with other heart rate inhibiting agents.

Nerve stimulation electrodes may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation electrodes. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon, which may be inflated with air or liquid to press the electrodes firmly against the vessel wall. Similar techniques may be performed by insertion of a catheter-type device into the trachea or esophagus. Additionally, tracheal devices, e.g., tracheal tubes, tracheal ablation devices, tracheal imaging devices, and/or esophageal devices, e.g., esophageal tubes, esophageal ablation devices, esophageal imaging devices, comprising electrodes may be used.

Nerve stimulation electrodes may be oriented in any fashion along the catheter device, including longitudinally or transversely. Various imaging techniques or modalities, as discussed earlier, such as ultrasound, fluoroscopy and echocardiography may be used to facilitate positioning of the electrodes. If desired or necessary, avoidance of obstruction of air flow or blood flow may be achieved with notched catheter designs or with catheters, which incorporate one or more tunnels or passageways.

In one embodiment of the present invention, the location of the electrodes is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with the vagal nerve or selected tissues.

Figure 17:
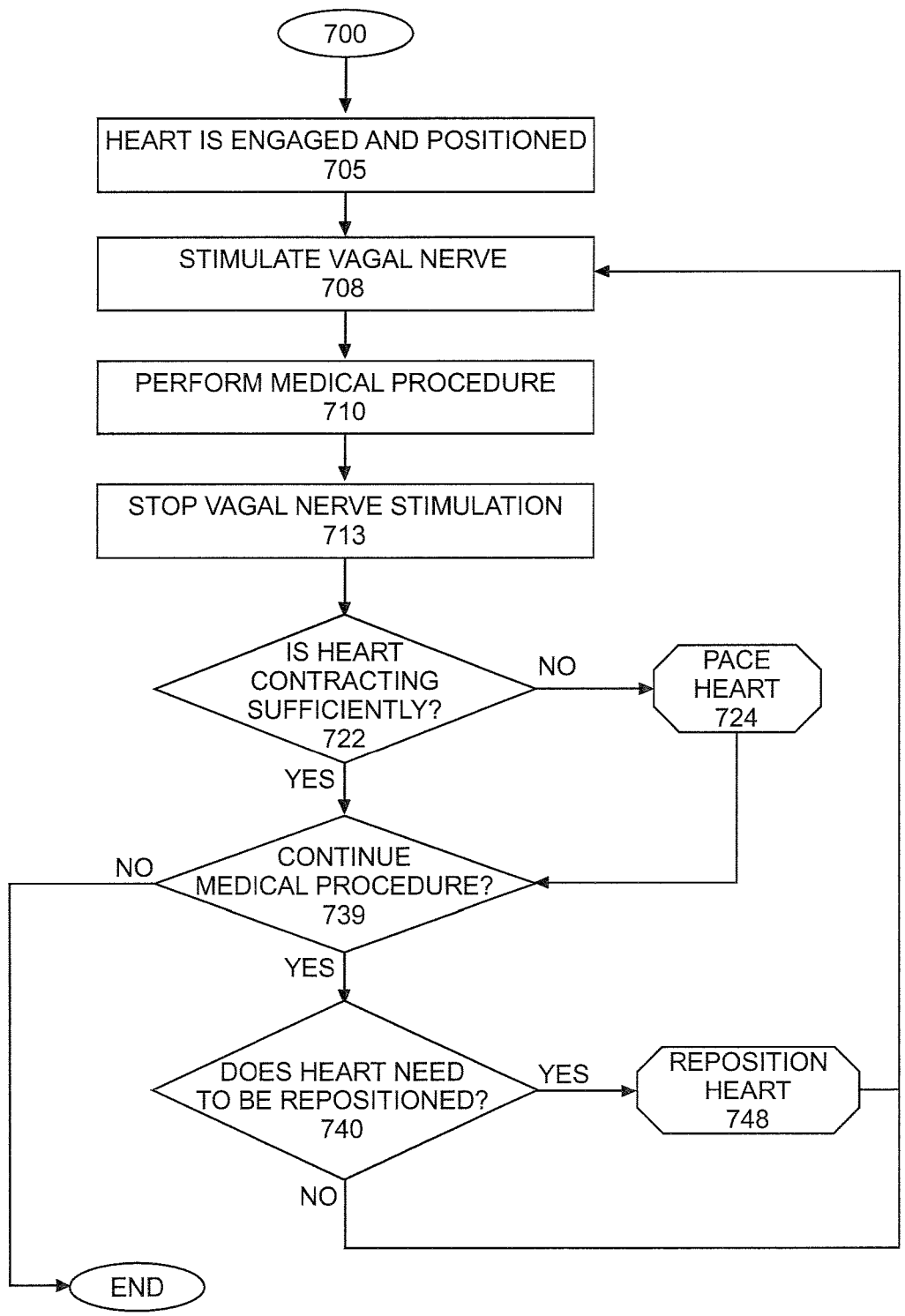
FIG. 17 is a flow diagram of one embodiment of the present invention.

FIG. 17 shows a flow diagram of one embodiment of the present invention. The patient is prepared for a medical procedure at 700. Once the patient is prepared, the heart is engaged and positioned using tissue-engaging device 200 (Block 705). Once the heart is positioned in a desired orientation, e.g., a non-physiological orientation, a nerve that controls the beating of the heart is stimulated to slow down or stop the contractions of the heart (Block 708). Such a nerve may be for example a vagal nerve. During this time, one or more of a variety of pharmacological agents or drugs may be delivered to the patient. Drugs may be administered without nerve stimulation. The types of drugs administered may produce reversible asystole of a heart while maintaining the ability of the heart to be electrically paced. Other drugs may be administered for a variety of functions and purposes. Drugs may be administered at the beginning of the procedure, intermittently during the procedure, continuously during the procedure or following the procedure. Examples of one or more drugs that may be administered include a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrhythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

Typically, vagal nerve stimulation prevents the heart from contracting. This non-contraction must then be followed by periods without vagal nerve stimulation during which the heart is allowed to contract, and blood flow is restored throughout the body. Following initial slowing or stopping of the heart, a medical procedure, such as imaging and/or ablation, is begun (Block 710). In one embodiment of the invention, one or more ultrasound ablation devices are positioned within the trachea, bronchi of the lungs and/or esophagus of the patient and ultrasound energy is emitted from the one or more ablation devices and is focused within tissue, e.g., cardiac tissue. Alternatively, an ablation device may be placed on the patient, e.g., on the chest of the patient. Following a brief interval of nerve stimulation while the ablation procedure is performed, nerve stimulation is ceased (Block 713) and the heart is allowed to contract.

The heart may be free to beat on its own or a cardiac stimulator or pacemaker comprising one or more cardiac stimulation electrodes may be used to cause the heart to contract (Blocks 722 and 724). Cardiac stimulation electrodes used to stimulate the heart may be, for example, non-invasive, e.g., clips, or invasive, e.g., needles or probes. Cardiac electrodes may be positioned through a thoracotomy, sternotomy, endoscopically through a percutaneous port, through a stab wound or puncture, through a small incision in the chest, placed on the chest or in combinations thereof. The present invention may also use various electrodes, catheters and electrode catheters suitable for pacing the heart, e.g., epicardial, patch-type, intravascular, balloon-type, basket-type, umbrella-type, tape-type electrodes, suction-type, pacing electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. Guided or steerable catheter devices comprising electrodes may be used alone or in combination with the electrodes. One or more cardiac electrodes, e.g., stimulation and/or monitoring electrodes, may be positioned on tissue-engaging device 200.

If the ablation procedure needs to continue or a new ablation procedure is to be performed, the heart again may be slowed or stopped via vagal nerve stimulation. In addition, the heart may be repositioned if necessary or desired at Block 748.

In one embodiment of the present invention, a probe device sized and shaped to fit within the trachea, bronchi and/or esophagus of the patient may comprise one or more nerve stimulation electrodes, members or elements and one or more ultrasound ablation members or elements. The probe device may be positioned within the trachea, bronchi and/or esophagus of the patient. The nerve stimulation electrodes may be used to stimulate one or more nerves of the patient, e.g., a vagal nerve, as disclosed earlier, while the probe device is positioned within the trachea, bronchi and/or esophagus of the patient. The ultrasound ablation members may be used to emit ultrasound energy to ablate tissue, e.g., cardiac tissue, as disclosed earlier, while the probe device is positioned within the trachea, bronchi and/or esophagus of the patient. The nerve stimulation electrodes may be coupled to a nerve stimulator, e.g., used to stimulate the patient's vagal nerve to slow or stop the patient's heart during an ablation procedure.

In one embodiment of the present invention, the tissue-engaging device may include one or more ultrasound ablation elements, as described earlier. The tissue-engaging device comprising one or more ultrasound ablation elements may be used to move and position tissue, e.g., heart tissue, as well as to ablate tissue within the focusing range of the one or more ultrasound ablation elements. The tissue-engaging device may be used to position tissue prior to an ablation procedure, during an ablation procedure and/or following an ablation procedure. In addition to cardiac tissue, other tissue types and/or organs may be ablated or treated by one or more ultrasound ablation elements of the device.

The distal end of the tissue-engaging device may be positioned within a patient through an incision, a stab wound, a port, a sternotomy and/or a thoracotomy. An endoscope may be used to help position the tissue-engaging device.

In one embodiment of the present invention, the ultrasound ablation device or system may comprise one or more switches to facilitate its regulation by a physician or surgeon. One example of such a switch is a foot pedal. The switch may also be, for example, a hand switch, or a voice-activated switch comprising voice-recognition technologies. The switch may be incorporated in or on one of the surgeon's instruments, such as surgical site retractor, or any other location easily and quickly accessed by the surgeon.

The ultrasound ablation device or system may include a display and/or other means of indicating the status of various components of the device to the surgeon such as a numerical display, gauges, a monitor display or audio feedback. The ultrasound ablation device may also include one or more visual and/or audible signals used to prepare a surgeon for the start or stop of the ablation procedure. Controller 16 may synchronize delivery of ablation energy to the ablation device 12 between heart beats to reduce inadvertent tissue damage. Controller 16 may be slaved to a nerve stimulator and/or a cardiac stimulator. Alternatively, a nerve stimulator and/or cardiac stimulator may be slaved to controller 16. Alternatively, controller 16 may be capable of nerve stimulation and/or cardiac stimulation.

In one embodiment of the present invention, one or more diagnostic transducers may be used to measure the desired ablative tissue area. System 900 would then suggest and/or control a specific transducer based on the desired lesion depth and configuration. The system could then deliver the amount and type of energy required to create the desired lesion. Electrodes of system 900 may be used for cardiac pacing, defibrillation, cardioversion, sensing, stimulation, and/or mapping.

System 900 may include suction source 300 for providing suction to tissue-engaging device 200 and/or ablation device 12. Tissue-engaging device 200 and/or ablation device 12 may be attached to a flexible or rigid hose or tubing for supplying suction and/or fluids from a suitable suction source and/or fluid source to the target tissue surface through suction and/or fluid elements, openings, orifices, or ports of device 200 and/or device 12. The hose or tubing may comprise one or more stopcocks and/or connectors such as luer connectors. Suction may be provided to device 200 and/or device 12 by the standard suction available in the operating room. Suction source 300 may be coupled to tissue-engaging device 200 and/or device 12 with a buffer flask and/or filter. Suction may be provided at a negative pressure of between 200-600 mm Hg with 400 mm Hg preferred. As used herein, the terms "vacuum" or "suction" refer to negative pressure relative to atmospheric or environmental air pressure in the operating room.

Suction may be provided via one or more manual or electric pumps, syringes, suction or squeeze bulbs or other suction or vacuum producing means, devices or systems. Suction source 300 may comprise one or more vacuum regulators, resistors, stopcocks, connectors, valves, e.g., vacuum releasing valves, filters, conduits, lines, tubes and/or hoses. The conduits, lines, tubes, or hoses may be flexible or rigid. For example, a flexible suction line may be used to communicate suction to device 200 and/or device 12, thereby allowing device 200 and/or device 12 to be easily manipulated by a surgeon. Another method that would allow the surgeon to easily manipulate device 200 and/or device 12 includes incorporation of suction source 300 into device 200 and/or device 12. For example, a small battery operated vacuum pump or squeeze bulb may be incorporated into device 200 and/or device 12.

Suction source 300 may be slaved to ablation assembly 10, tissue-engaging device 200, fluid source 400, sensor 600, imaging device 800, a drug delivery device, a guidance device and/or a stimulation device. For example, suction source 300 may be designed to automatically stop suction when controller 16 sends a signal to stop suction. Suction source 300 may include a visual and/or audible signal used to alert a surgeon to any change in suction. For example, a beeping tone or flashing light may be used to alert the surgeon when suction is present. Suction source 300 may be slaved to a robotic system or a robotic system may be slaved to suction source 300. Suction may be used to secure, anchor or fix tissue-engaging device 200 and/or device 12 to an area of tissue. The area of tissue may comprise a beating heart or a stopped heart. Suction may be used to remove or aspirate fluids from the target tissue site. Fluids removed may include, for example, blood, saline, Ringer's solution, ionic fluids, contrast fluids, irrigating fluids and energy-conducting fluids. Steam, vapor, smoke, gases and chemicals may also be removed via suction.

System 900 may include fluid source 400 for providing fluids, for example, to tissue-engaging device 200, ablation device 12 and/or the patient. Tissue-engaging device 200 may be attached to a flexible or rigid hose or tubing for supplying fluids from fluid source 400 to the target tissue through fluid elements, openings, orifices, or ports of device 200. Ablation device 12 may be attached to a flexible or rigid hose or tubing for receiving fluids from fluid source 400 and for supplying fluids, if desired, to the target tissue through fluid elements, openings, orifices, or ports of device 12.

Fluid source 400 may be any suitable source of fluid. Fluid source 400 may include a manual or electric pump, an infusion pump, a peristaltic pump, a roller pump, a centrifugal pump, a syringe pump, a syringe, or squeeze bulb or other fluid moving means, device or system. For example, a pump may be connected to a shared power source or it may have its own source of power. Fluid source 400 may be powered by AC current, DC current, or it may be battery powered either by a disposable or re-chargeable battery. Fluid source 400 may comprise one or more fluid regulators, e.g., to control flow rate, valves, fluid reservoirs, resistors, filters, conduits, lines, tubes and/or hoses. The conduits, lines, tubes, or hoses may be flexible or rigid. For example, a flexible line may be connected to devices 12 and/or 200 to deliver fluid and/or remove fluid, thereby allowing device 200 to be easily manipulated by a surgeon. Fluid reservoirs may include an IV bag or bottle, for example.

Fluid source 400 may be incorporated into tissue-engaging device 200 and/or ablation device 12, thereby delivering fluid or removing fluid at the target tissue site. Fluid source 400 may be slaved to tissue-engaging device 200 and/or ablation device 12, suction source 300, sensor 600 and/or imaging device 800. For example, fluid source 400 may be designed to automatically stop or start the delivery of fluid while tissue-engaging device 200 is engaged with tissue or while ablation device 12 is ablating tissue. Ablation system 10, tissue-engaging device 200, suction source 300, fluid source 400, sensor 600 and/or imaging device 800 may be slaved to a robotic system or a robotic system may be slaved to ablation system 10, tissue-engaging device 200, suction source 300, fluid source 400, sensor 600 and/or imaging device 800.

Fluid source 400 may comprise one or more switches, e.g., a surgeon-controlled switch. One or more switches may be incorporated in or on fluid source 400 or any other location easily and quickly accessed by the surgeon for regulation of fluid delivery by the surgeon. A switch may be, for example, a hand switch, a foot switch, or a voice-activated switch comprising voice-recognition technologies. A switch may be physically wired to fluid source 400 or it may be a remote control switch. Fluid source 400 and/or system 10 may include a visual and/or audible signal used to alert a surgeon to any change in the delivery of fluid. For example, a beeping tone or flashing light may be used to alert the surgeon that a change has occurred in the delivery of fluid.

Fluids delivered to tissue-engaging device 200 and/or ablation device 12 may include saline, e.g., normal, hypotonic or hypertonic saline, Ringer's solution, ionic, contrast, blood, and/or energy-conducting liquids. An ionic fluid may electrically couple an electrode to tissue thereby lowering the impedance at the target tissue site. An ionic irrigating fluid may create a larger effective electrode surface. An irrigating fluid may cool the surface of tissue thereby preventing over heating or cooking of tissue which can cause popping, desiccation, and charring of tissue. A hypotonic irrigating fluid may be used to electrically insulate a region of tissue. Fluids delivered to tissue-engaging device 200 and/or ablation device 12 may include gases, adhesive agents and/or release agents.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered with or without a fluid to the patient. Biological agents may be found in nature (naturally occurring) or may be chemically synthesized. Cells and cell components, e.g., mammalian and/or bacterial cells, may be delivered to the patient. A platelet gel or tissue adhesive may be delivered to the patient.

One or more of a variety of pharmacological agents, biological agents and/or drugs may be delivered or administered to a patient, for a variety of functions and purposes as described below, prior to a medical procedure, intermittently during a medical procedure, continuously during a medical procedure and/or following a medical procedure. For example, one or more of a variety of pharmacological agents, biological agents and/or drugs, as discussed above and below, may be delivered before, with or after the delivery of a fluid.

Drugs, drug formulations or compositions suitable for administration to a patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present invention, system 900 may include a drug delivery device (not shown). The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the iontophoresis electrodes may also be used as nerve stimulation electrodes or as cardiac stimulation electrodes.

A drug delivery device may be incorporated into tissue-engaging device 200 and/or ablation device 12, thereby delivering drugs at or adjacent the target tissue site or the drug delivery device may be placed or used at a location differing from the location of tissue-engaging device 200 and/or ablation device 12. For example, a drug delivery device may be placed in contact with the inside surface of a patient's heart while tissue-engaging device 200 and/or ablation device 12 is placed or used on the outside surface of the patient's heart.

The drug delivery device may be slaved to ablation system 10, tissue-engaging device 200, suction source 300, fluid source 400, sensor 60 and/or imaging device 800. For example, a drug delivery device may be designed to automatically stop or start the delivery of drugs during tissue engagement of tissue-engaging device 200 and/or during tissue ablation via ablation device 12. The drug delivery device may be slaved to a robotic system or a robotic system may be slaved to the drug delivery device.

The drug delivery device may comprise one or more switches, e.g., a surgeon-controlled switch. One or more switches may be incorporated in or on the drug delivery device or any other location easily and quickly accessed by the surgeon for regulation of drug delivery by the surgeon. A switch may be, for example, a hand switch, a foot switch, or a voice-activated switch comprising voice-recognition technologies. A switch may be physically wired to the drug delivery device or it may be a remote control switch. The drug delivery device and/or system 900 may include a visual and/or audible signal used to alert a surgeon to any change in the medical procedure, e.g., in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blacker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

The drug delivery device may include a vasodilative delivery component and/or a vasoconstrictive delivery component. Both delivery components may be any suitable means for delivering vasodilative and/or vasoconstrictive drugs to a site of a medical procedure. For example, the drug delivery device may be a system for delivering a vasodilative spray and/or a vasoconstrictive spray. The drug delivery device may be a system for delivering a vasodilative cream and/or a vasoconstrictive cream. The drug delivery device may be a system for delivering any vasodilative formulation such as an ointment or medicament etc. and/or any vasoconstrictive formulation such as an ointment or medicament etc. or any combination thereof.

The drug delivery device may comprise a catheter, such as a drug delivery catheter or a guide catheter, for delivering a vasodilative substance followed by a vasoconstrictive substance. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. In one embodiment, one catheter may be used to deliver both a vasodilative component and a vasoconstrictive component. The drug delivery device may be a patch, such as a transepicardial patch that slowly releases drugs directly into the myocardium, a cannula, a pump and/or a hypodermic needle and syringe assembly. The drug delivery device may be an iontophoretic drug delivery device placed on the heart.

A vasodilative component may comprise one or more vasodilative drugs in any suitable formulation or combination. Examples of vasodilative drugs include, but are not limited to, a vasodilator, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine and a dopamine D1-like receptor agonist, stimulant or activator. The vasodilative component may include a pharmaceutically acceptable carrier or solution in an appropriate dosage.

A vasoconstrictive component may comprise one or more suitable vasoconstrictive drugs in any suitable formulation or combination. Examples of vasoconstrictive drugs include, but are not limited to, a vasoconstrictor, a sympathomimetic, methoxamine hydrochloride, epinephrine, midodrine hydrochloride, desglymidodrine, and an alpha-receptor agonist, stimulant or activator. The vasoconstrictive component may include a pharmaceutically acceptable carrier or solution in an appropriate dosage.

Controller 16 may process sensed information from a sensor. The controller may store and/or process such information before, during and/or after a medical procedure, e.g., an ablation procedure. For example, the patient's tissue temperature may be sensed, stored and processed prior to and during the ablation procedure.

Controller 16 may be used to control the energy supplied to one or more energy transfer elements, e.g., electrodes or transducers, of tissue-engaging device 200 and/or ablation device 12. Controller 16 may also gather and process information from one or more sensors. This information may be used to adjust energy levels and times. Controller 16 may incorporate one or more switches to facilitate regulation of the various system components by the surgeon. One example of such a switch is a foot pedal. A switch may also be, for example, a hand switch, or a voice-activated switch comprising voice-recognition technologies. A switch may be physically wired to controller 16 or it may be a remote control switch. A switch may be incorporated in or on one of the surgeon's instruments, such as surgical site retractor, e.g., a sternal or rib retractor, tissue-engaging device 200 and/or ablation device 12, or any other location easily and quickly accessed by the surgeon. Controller 16 may also include a display. Controller 16 may also include other means of indicating the status of various components to the surgeon such as a numerical display, gauges, a monitor display or audio feedback.

Controller 16 may incorporate a cardiac stimulator and/or cardiac monitor. For example, electrodes used to stimulate or monitor the heart may be incorporated into tissue-engaging device 200 and/or ablation device 12. Controller 16 may incorporate a nerve stimulator and/or nerve monitor. For example, electrodes used to stimulate or monitor one or more nerves, e.g., a vagal nerve, may be incorporated into tissue-engaging device 200 and/or ablation device 12. Controller 16 may comprise a surgeon-controlled switch for cardiac stimulation and/or monitoring, as discussed earlier. Controller 16 may comprise a surgeon-controlled switch for nerve stimulation and/or monitoring, as discussed earlier. Cardiac stimulation may comprise cardiac pacing and/or cardiac defibrillation. Controller 16, tissue-engaging device 200 and/or ablation device 12 may incorporate a cardiac mapping device for mapping the electrical signals of the heart.

A visual and/or audible signal used to alert a surgeon to the completion or resumption of energy delivery, suction, sensing, monitoring, stimulation and/or delivery of fluids, drugs and/or cells may be incorporated into controller 16. For example, a beeping tone or flashing light that increases in frequency as the energy delivered increases.

System 900 may include sensor 600. Sensor 600 may be incorporated into tissue-engaging device 200 and/or ablation device 12 or it may be incorporated into another separate device. A separate sensor device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof.

Sensor 600 may comprise one or more switches, e.g., a surgeon-controlled switch. One or more switches may be incorporated in or on a sensor device or any other location easily and quickly accessed by the surgeon for regulation of sensor 600 by the surgeon. A switch may be, for example, a hand switch, a foot switch, or a voice-activated switch comprising voice-recognition technologies. A switch may be physically wired to sensor 600 or it may be a remote control switch.

Sensor 600 may include a visual and/or audible signal used to alert a surgeon to any change in the measured parameter, for example, tissue temperature, cardiac hemodynamics or ischemia. A beeping tone or flashing light may be used to alert the surgeon that a change has occurred in the parameter sensed.

Sensor 600 may comprise one or more temperature-sensitive elements, such as a thermocouple, to allow a surgeon to monitor temperature changes of a patient's tissue. Alternatively, sensor 600 may sense and/or monitor voltage, amperage, wattage and/or impedance. For example, an ECG sensor may allow a surgeon to monitor the hemodynamics of a patient during a heart positioning procedure. The heart may become hemodynamically compromised during positioning and while in a non-physiological position. Alternatively, sensor 600 may be any suitable blood gas sensor for measuring the concentration or saturation of a gas in the blood or tissues. For example, sensor 600 may be a sensor for measuring the concentration or saturation of oxygen or carbon dioxide in the blood or tissues. Alternatively, sensor 600 may be any suitable sensor for measuring blood pressure or flow, for example a Doppler ultrasound sensor system, or a sensor for measuring hematocrit (HCT) levels.

Alternatively sensor 600 may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

Sensor 600 may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

Sensor 600 may be used to detect naturally detectable properties representative of one or more characteristics, e.g., chemical, physical, mechanical, thermal, electrical or physiological, of system 900 and/or a patient's bodily tissues or fluids. For example, naturally detectable properties of patient's bodily tissues or fluids may include pH, fluid flow, electrical current, impedance, temperature, pressure, tension, components of metabolic processes, chemical concentrations, for example, the absence or presence of specific peptides, proteins, enzymes, gases, ions, etc. Naturally detectable properties of system 900 may include, for example, pressure, tension, stretch, fluid flow, electrical, mechanical, chemical and/or thermal. For example, sensor 600 may be used to sense, monitor and/or control suction or vacuum delivered from suction source 300. Sensor 600 may be used to measure suction between device 200 and tissue. Sensor 600 may be used to sense, monitor and/or control fluid delivered from fluid source 400. Sensor 600 may be used to sense, monitor and/or control energy delivered from power supply 14 via controller 16.

Sensor 600 may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor.

Sensor 600 may be incorporated into tissue-engaging device 200 and/or ablation device 12 or sensor 600 may be placed or used at a location differing from the location of tissue-engaging device 200 and/or ablation device 12. For example, sensor 600 may be placed in contact with the inside surface of a patient's heart while tissue-engaging device 200 and/or ablation device 12 is placed or used on the outside surface of the patient's heart.

Ablation assembly 10, tissue-engaging device 200, suction source 300, fluid source 400, drug delivery device and/or processor 800 may be slaved to sensor 600. For example, tissue-engaging device 200 may be designed to automatically adjust suction if sensor 600 measures a predetermined sensor value, e.g., a particular suction value, or ablation device 12 may be designed to stop or start the ablation of tissue if sensor 600 measures a predetermined sensor value, e.g., a particular tissue temperature.

Sensor 600 may include a visual and/or audible signal used to alert a surgeon to any change in the one or more characteristics the sensor is sensing and/or monitoring. For example, a beeping tone or flashing light that increases in frequency as tissue temperature rises may be used to alert the surgeon.

Controller 16 may include one or more processors. A processor may receive and preferably interpret the signal from sensor 600. A processor may comprise software and/or hardware. A processor may comprise fuzzy logic. A suitable amplifier may amplify signals from sensor 600 before reaching a processor. The amplifier may be incorporated into a processor. Alternatively the amplifier may be incorporated into sensor 600 or tissue-engaging device 200 or ablation device 12. Alternatively, the amplifier may be a separate device. A processor may be a device separate from ablation assembly 10, tissue-engaging device 200, suction source 300, fluid source 400, sensor 600 and/or imaging device 800. A processor may be incorporated into ablation device 12, tissue-engaging device 200, suction source 300, fluid source 400, sensor 600 and/or imaging device 800. A processor may control the energy delivered from the power supply 14. For example, a signal of a first intensity from sensor 600 may indicate that the energy level from power supply 14 should be lowered; a signal of a different intensity may indicate that power supply 14 should be turned off. Preferably, a processor may be configured so that it may automatically raise or lower the suction delivered to device 12 and/or device 200 from suction source 300, the fluids delivered to device 12 and/or device 200 from fluid source 400 and/or the energy delivered to device 12 and/or device 200 from power supply 14. Alternatively, the control of suction source 300, fluid source 400 and/or power supply 14 based on output from a processor may be manual.

Controller 16 may include a visual display or monitor, such as, for example, a LCD or CRT monitor, to display various amounts and types of information. By software control, the user may choose to display the information in a number of ways. The monitor may show, for example, a currently sensed parameter, e.g., temperature. The monitor may also lock and display the maximum sensed value achieved. Sensed information may be displayed to the user in any suitable manner, such as for example, displaying a virtual representation of ablation device 12 and/or tissue-engaging device 200 on the monitor.

Alternatively, the monitor may display the voltage corresponding to the signal emitted from sensor 600. This signal corresponds in turn to the intensity of a sensed parameter at the target tissue site. Therefore a voltage level of 2 would indicate that the tissue was, for example, hotter than when the voltage level was 1. In this example, a user would monitor the voltage level and, if it exceeded a certain value, would turn off or adjust the power supply 14.

The display of controller 16 may alternatively be located on ablation device 12, power supply 14, tissue-engaging device 200, suction source 300, fluid source 400, sensor 600 and/or imaging device 800. An indicator, such as an LED light, may be permanently or removeably incorporated into ablation device 12, power supply 14, tissue-engaging device 200, suction source 300, fluid source 400, sensor 600 and/or imaging device 800. The indicator may receive a signal from sensor 600 indicating that the tissue had reached an appropriate value, for example temperature. In response, the indicator may turn on, change color, grow brighter or change in any suitable manner to indicate that the flow of energy from power supply 14 should be modified or halted. The indicator may also be located on ablation device 12, power supply 14, tissue-engaging device 200, suction source 300, fluid source 400, sensor 60 and/or imaging device 800 and/or may be located on another location visible to the user.

Controller 16 may include an audio device that indicates to the user that the delivery of suction, fluids and/or energy should be halted or adjusted. Such an audio device may be, for example, a speaker that broadcasts a sound (for example, a beep) that increases in intensity, frequency or tone as a parameter sensed by sensor 600 increases. The user may adjust, for example, turn down or turn off power supply 14 when the sound emitted reaches a given volume or level. In another embodiment, the audio device may also give an audible signal (such as the message "turn off energy source"), for example, when a parameter sensed by sensor 600 reaches a certain level. Such an audio device may be located on tissue-engaging device 200, suction source 300, fluid source 400, sensor 600 and/or imaging device 800. The audio device may also be a separate device.

In one embodiment of the present invention, system 900 may include an imaging device 800. Imaging device 800 may be based on one or more imaging modalities such as ultrasound imaging, CT, MRI, PET, fluoroscopy, echocardiography, etc. The coordinates for the desired area of ablation, for example, from any of these imaging modalities can be electronically fed to controller 16 such that the desired ablation pattern can be generated and ablated. The imaging device may have two and/or three-dimensional imaging capabilities as well as phased and/or annular array imaging capabilities. For example, two or three-dimensional echocardiography, such as transesophageal echocardiography (TEE), or ultrasound imaging, such as transthoracic ultrasound imaging may be possible with use of imaging device 800.

The imaging device may comprise one or more light sources and/or illuminating materials, e.g., glow-in-the-dark materials. For example, the tissue-engaging head of device 200 and/or one or more portions of ablation device 12 may comprise one or more glow-in-the-dark materials. The imaging device may be based on fluorescence technologies. The imaging device may comprise fiber optic technologies; for example a fiber optic conduit may deliver light from a remote light source to an area adjacent tissue-engaging device 200 and/or ablation device 12 for illumination of a treatment site.

The imaging device may comprise a light pipe, for example, to illuminate the tissue-engaging head of device 200 and/or ablation device 12 and/or the surgical field adjacent device 200 and/or device 12. A transparent, semi-transparent or translucent tissue-engaging head may be illuminated merely by placement of the end of a light pipe or other light source adjacent the tissue-engaging head of device 200. A transparent, semi-transparent or translucent portion of ablation device 12 may be illuminated merely by placement of the end of a light pipe or other light source adjacent the transparent, semi-transparent or translucent portion of ablation device 12.

The imaging device may include a visual display or monitor, such as, for example, a LCD or CRT monitor, to display various amounts and types of information. By software control, the user may choose to display the information in a number of ways. The imaging device may be powered by AC current, DC current, or it may be battery powered either by a disposable or re-chargeable battery. The imaging device may provide UV, IR and/or visible light. The imaging device may include a laser. The imaging device may be incorporated into tissue-engaging device 200 and/or ablation device 12 or it may be incorporated into a separate device. A separate imaging device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. A separate imaging device may be positioned through one or more body cavity openings of the patient and/or positioned outside the patient, e.g., on the skin of the patient. One or more imaging devices may be positioned in the esophagus, the trachea and/or the bronchi of the lungs.

The imaging device may comprise one or more switches, e.g., a surgeon-controlled switch. One or more switches may be incorporated in or on the imaging device or any other location easily and quickly accessed by the surgeon for regulation of the imaging device by the surgeon. A switch may be, for example, a hand switch, a foot switch, or a voice-activated switch comprising voice-recognition technologies. A switch may be physically wired to the imaging device or it may be a remote control switch.

Ablation assembly 10, tissue-engaging device 200, suction source 300, fluid source 400, a drug delivery device and/or imaging device may be slaved to a robotic system or a robotic system may be slaved to ablation assembly 10, tissue-engaging device 200, suction source 300, fluid source 400, sensor 60, a drug delivery device and/or imaging device. Computer- and voice-controlled robotic systems that position and maneuver endoscopes and/or other surgical instruments for performing microsurgical procedures through small incisions may be used by the surgeon to perform precise and delicate maneuvers. These robotic systems may allow the surgeon to perform a variety of microsurgical procedures. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

A medical procedure wherein one or more components of system 900 may be used may be non-invasive, minimally invasive and/or invasive. The medical procedure may entail a port-access approach, a partially or totally endoscopic approach, a sternotomy approach or a thoracotomy approach. The medical procedure may include the use of various robotic or imaging systems. The medical procedure may be surgery on the heart. Alternatively, the medical procedure may be surgery performed on another organ of the body.

In one embodiment of the present invention, a positioning or tissue-engaging device may comprise one or more sensors and/or electrodes, e.g., sensing electrodes and/or stimulation electrodes. In another embodiment of the present invention, an imaging device may comprise one or more sensors and/or electrodes, e.g., sensing electrodes and/or stimulation electrodes. In another embodiment of the present invention, a positioning or tissue-engaging device may comprise imaging capabilities, e.g., ultrasound imaging, and one or more sensors and/or electrodes, e.g., sensing electrodes and/or stimulation electrodes.

In one embodiment of the present invention, an ablation device may comprise one or more sensors and/or electrodes, e.g., sensing electrodes and/or stimulation electrodes. In another embodiment of the present invention, an ablation device may comprise imaging capabilities, e.g., ultrasound imaging, and/or one or more electrodes, e.g., stimulation electrodes. In another embodiment of the present invention, an ablation device may comprise tissue-positioning capabilities, e.g., suction engagement of tissue. In one embodiment of the invention, ablation device 12 may be guided or steerable.

In one embodiment of the present invention, transducer elements 28 may comprise one or more configurations varying in size and shape. For example, transducer elements 28 may be round, as shown in FIG. 2. Alternatively, transducer elements 28 may be elongated or linear in shape, as shown in FIGS. 18 and 19. Transducers elements 28 may be arranged on or in housing 26 in various configurations. In FIG. 2, for example, transducers elements 28 are shown arranged in a planar array of three rows R and six columns C, although the transducer elements can be arranged in any number of rows and columns. Alternatively, the transducer elements may be angled to a more central area to create a lesion of a desired shape rather than in a row aimed along the same axis. In FIG. 19, elongated transducer elements 28 are shown arranged along a curve. Housing 26 may be configured to have one or more shapes, such as a round shape, an oval shape, a square shape, a rectangular shape, a triangular shape, a concave cave shape, a convex shape, a flat shape, etc. In FIG. 2, for example, housing 26 is shown to have a flat, rectangular shape. Alternatively, in FIGS. 18 and 19, for example, housing 26 is shown to have a concave, rectangular shape. The transducer elements 28, in FIG. 19, are shown aligned relatively parallel to each other. Linear transducer elements as shown in FIGS. 18 and 19 would be capable of producing a line of focused energy.

In one embodiment of the present invention, devices, systems, and methods that may be used for guidance of a medical device, e.g., an ablation device, in a minimally invasive medical procedure, include electromagnetic devices, systems and methods, electric field devices, systems and methods, and ultrasound devices, systems and methods. Examples of various tracking, monitoring, positioning, guiding and/or navigating technologies are disclosed in U.S. Pat. Nos. 5,782,765; 6,190,395; 6,235,038; 6,379,302; 6,381,485; 6,402,762; 6,434,507; 6,474,341; 6,493,573; 6,636,757; 6,669,635; 6,701,179; 6,725,080, the entire disclosures of which are incorporated herein by reference.

A guidance device, system, and/or method that may be used according to one embodiment of the invention include the use of electrical fields, for example, electric fields passing in three axes through a patient's body. In one embodiment, three pairs of sensors, e.g., electrode patches, are positioned in electrical contact with the patient's body. In one embodiment, one set of the electrode patch sensors are oriented in each of the three axes, side-to-side, front-to-back, and head-to-toe, e.g., electrode patch sensors located on neck and thigh. A 40.1 KHz, 40.2 KHz, and 40.3 KHz signal is transmitted, for example, between each of the three sets of electrode patch sensors, respectively. The three signals transmitted between the electrode patch sensors, may be picked up by sensors, e.g., electrodes, positioned on medical devices placed within the patient's body, e.g., within the patient's cardiovascular system or thoracic cavity. Sensor electrodes that are in contact with electrically conductive tissue and/or fluids, e.g., blood, may be monitored from outside of the body via the three signals transmitted between the three pairs of electrode patch sensors, since there will be a voltage drop across each of the three inter-patch spaces within the body associated with electrodes of the medical devices. The voltage drop may be used to calculate the location of the monitored sensor electrode(s) in 3-D space within the patient's body. One embodiment of an electric field guidance device may track the position of up to 10 sensor electrodes simultaneously. An electric field guidance device or system may include a visual monitor or display to display electrode locations or positions. For example, the monitored sensor electrodes may be shown on a three axis coordinate grid on a monitor or display. In one embodiment, the electric field guidance device achieves the best accuracy when the electric field gradients are uniform. Distortions to the electric fields may cause inaccuracies in the rendered position of the electrodes. Electric field distortions may be caused by air voids, for example, within the thoracic cavity. Therefore, sensor electrodes that are being tracked should maintain contact with conductive tissue and/or fluids to have their positions monitored continuously, for example, on the coordinate system.

A guidance device, system, and/or method may use one or more imaging devices to acquire images, for example, previously acquired ultrasound, CT, MRI, PET, fluoroscopy and/or echocardiography images, to provide real-time medical device monitoring, positioning, tracking and/or guidance. Previously acquired images may be registered to the patient. For example, acquired images of anatomical structures of the patient may be accurately registered to the patient's anatomy in real-time. The guidance device or system may then show, for example, on a visual monitor or display, the locations or positions of the medical device sensors relative to a previously acquired image or images, thereby providing real-time monitoring, positioning, tracking and/or guidance of the medical device or devices relative to an image or images of the patient's anatomy.

A guidance device, system, and method that may be used according to one embodiment of the invention include the use of a magnetic field. In one embodiment, sensors comprising three small coils are positioned and oriented in three different axes of a medical device, e.g., an ablation device, and a sensor, e.g., an antenna pad, is placed in contact with the patient's body, for example, the antenna sensor pad is placed under the patient. The magnetic field guidance device and method senses the 3-D location of the three sensor coils of the medical device. The 3-D location of the sensor coils may then be displayed or represented on a visual monitor or display, for example, as shown on a three axis coordinate grid. Again, the guidance device, system, and/or method may use one or more imaging devices to acquire images to provide real-time medical device monitoring, positioning, tracking and/or guidance. For example, a device comprising sensor coils may be monitored as the portion of the device comprising the sensor coils is moved around a space, cavity or chamber, e.g., a cardiac chamber, within the patient. The geometry of the space, cavity or chamber may then be mapped and displayed, for example, on a visual monitor or display. The accuracy of the geometric mapping of a space, cavity or chamber is generally related to the number of data points collected or monitored. A magnetic field guidance device or system is generally not sensitive to air voids within the patient's body.

A guidance device and method that may be used according to one embodiment of the invention includes the use of ultrasound. In one embodiment, sensors comprising ultrasound transducers are incorporated into a medical device, e.g., an ablation device. The ultrasound transducer sensors of the medical device to be tracked emit ultrasonic energy. The ultrasonic energy is then received by ultrasonic transducer sensors on other devices within the patient's body or in contact with the patient's body. The ultrasound guidance device may then display the relative positions of one or more of the ultrasound transducer sensors and renders images of the devices incorporating the ultrasound transducer sensors. Again, the guidance device, system, and/or method may use one or more imaging devices to acquire images to provide real-time medical device monitoring, positioning, tracking and/or guidance. The 3-D location of the ultrasound transducer sensors may be displayed or represented on a visual monitor or display, for example, as shown on a three axis coordinate grid layered onto a previously acquired image. The ultrasound guidance device or system can be very sensitive to air voids or differences in the speed of sound within various types of tissues and/or fluids.

A guidance device, system, and method that may be used according to one embodiment of the invention include the use of an electromagnetic field transmitter that may be coupled to an image intensifier of a fluoroscopic imaging device, e.g., a fluoroscope. In one embodiment, the guidance device or system may transmit three alternating magnetic fields that may be received by coils within the field of interest. The electromagnetic field transmitter may contain a matrix of small metal spheres that may be used to normalize a fluoroscopic image. In one embodiment, fluoroscopic images are acquired in one or more directional orientations using a fluoroscopic imaging device or system. The acquired images are then viewed by a physician who is then able to track and guide a medical device within the field of interest. In one embodiment, each medical device tracked and/or guided comprises at least one receiving sensor coil that allows the medical device to which it is attached to be tracked in 3D space with respect to the previously acquired fluoroscopic image or images.

In embodiment of the present invention, previously acquired images, e.g., images of a patient's thoracic cavity, acquired by one or more imaging devices may be displayed while displaying images and precise locations of one or more medical devices inserted into the patient, e.g., the patient's thoracic cavity. The medical devices may be hand held, manually controlled, remotely controlled, e.g., by magnetic fields, and/or robotically controlled. Each medical device that is to be tracked in real-time comprises at least one sensor coil. In one embodiment, electromagnetic navigation or guidance technology utilizes a system that transmits three separate electromagnetic fields that are sensed by a single sensor coil or multiple sensor coils mounted on the medical device to be tracked. In one embodiment, each medical device to be monitored and/or tracked in 3-D space requires at least one sensor coil. Additional medical device sensor coils may provide details regarding the shape and/or path of the medical device, for example. The shape of a flexible and/or articulating portion of a medical device may be provided via sensor coils positioned on or within the flexible and/or articulating portion. For example, an elongated flexible member of a medical device may have multiple sensor coils positioned along its length. In one embodiment, accurate registration of a previously acquired anatomical image may be performed using surface fiducial registration points as well as internal, implanted and/or indwelling reference devices. The form of reference points required to register the image to the true anatomy may depend on the accuracy needed for the particular procedure and anatomy of interest. In terms of information management to the surgeon, one embodiment of this invention couples visual imaging, e.g., endoscopic imaging, with navigation or guidance through the virtual anatomy.

One embodiment of the present invention involves first imaging of the patient's area of interest, e.g., the patient's thoracic cavity anatomy, using, for example, one or more plane fluoroscopy, computed tomography (CT), magnetic resonance (MR) imaging, and/or one or more plane 2-D or 3-D ultrasound imaging prior to the procedure. The initial imaging may be carried out by first placing fiduciary markers on specific points on or in the patient's body. The fiduciary markers may be easily identified on the images via use of one or more contrast agents or materials identifiable to the particular imaging technique used. The fiduciary markers may be attached to the skin, positioned subcutaneously, implanted, positioned in the trachea, bronchi, and/or esophagus, or may be inserted into the cardiovascular system, for example. In one embodiment, a medical device, e.g., a catheter or catheter-like device, having multiple sensor coils may be placed through the venous system through the inferior vena cava and/or superior vena cava and extended into various additional portions of the right side of the heart, e.g., the right atrial appendage, the coronary sinus, the right ventricle, the inter-ventricular septum, the right ventricular apex, the right ventricular outflow tract, and/or the pulmonary arteries. In one embodiment, delivery to sites such as the pulmonary arteries may be aided by the addition of a balloon positioned at or near the distal end of the fiduciary marking device to make use of blood flow to force the device downstream into the distal end of the right side of the cardiovascular system and into one or more of the pulmonary arteries. Additionally, such a fiduciary marking device may be placed in the arterial side of the cardiovascular system, whereby it may be introduced via an artery into the ascending aorta and extended through the descending aorta (or into superior arterial vessels) and into the aortic valve, the left ventricle, the inter-ventricular septum, the left ventricular apex, the mitral valve annulus, the left atrium, the left atrial appendage, and/or the pulmonary veins. In one embodiment, on or more fiduciary devices inserted into the esophagus and/or trachea may be used to track in-real time respiration effects on the posterior aspects of the heart. One or more reference sensor coils or marking points may be incorporated into a tracheal tube used for a patient on a respirator. One or more reference sensor coils or marking points may be incorporated into an esophageal tube. An esophageal reference may provide information of the location or position of the esophagus during procedures, e.g., involving ablation of regions of the left atrium. The location or position of the esophagus, for example, during an ablation procedure may be valuable to prevent or minimize any damage that could occur during the delivery of an ablation therapy.

In one embodiment, the guidance device or system may include one or more fiducial marking and/or reference devices. The fiducial marking and reference devices may be placed, for example, in and around the heart, e.g., endocardially, epicardially and/or in the pericardial space, to define the real-time precise location of the heart's surfaces and structures. An imaging device may be used to perform an imaging technique while one or more fiduciary marking and reference devices are positioned at one or more locations. Imaging may be performed with regard to respiration and/or cardiac cycle of the patient, such that the motions associated with respiration and/or the beating of the heart may be accounted for during the timing of the acquisition of the images. Placement of fiduciary marking and reference devices may be determined by the physician according to the anatomy of interest where the highest accuracy of the medical devices with respect to the anatomical structures is required. Placements of fiduciary marking and reference devices may be performed using fluoroscopy.

In one embodiment, the guidance device or system may be used during a heart valve replacement or repair procedure. For example, a pulmonic valve replacement procedure using a transvascular approach may involve preliminary imaging with an imaging device, wherein imaging is performed with skin surface fiduciary markers and a fiduciary marking catheter device placed through the venous system into the right ventricular outflow tract and to the site of the pulmonic valve annulus. After the preliminary imaging is complete and the patient is in the operating room, the pre-acquired image is then registered to the patient using the surface fiduciary markers as well as the internal catheter to provide high accuracy in the region of critical interest at the pulmonic valve annulus. The fiduciary catheter device may then be removed and a valve delivery and deployment device may be advanced into the site of the pulmonic valve for delivery and deployment of a replacement valve. During valve delivery and deployment, a physician may use the image guidance navigation device or system to view the real-time location and advancement of the valve delivery and deployment device and to view its motion through the cardiovascular system all the way to the site of deployment at the pulmonic valve annulus, for example.

In one embodiment, the guidance device or system may be used during a minimally invasive ablation procedure, e.g., an epicardial ablation procedure, to treat, for example, atrial fibrillation. One such procedure may involve the dissection and/or retraction of tissue to form a path around the cardiac anatomy through which an ablation device may be placed to create one or more ablation lesions from the epicardial aspect. In one embodiment of the present invention, the ablation procedure may be performed from the right side of the patient. One or more structures that may be of interest to a surgeon upon entry into a patient's thoracic cavity, e.g., entry through a small incision or port access, may be the location of the pericardial sac and associated structures such as the phrenic nerve. Also of interest may be the location and courses of the caval veins, i.e., the inferior and superior vena cava, the pulmonary arteries, and/or the pulmonary veins. In one embodiment, the caval veins and other structures may be registered to one or more pre-acquired images using fiducial marking devices placed in the venous cardiovascular system. In one embodiment, the pericardial reflections that are located between the superior pulmonary veins are separated. In this region, a surgeon must be careful to avoid damage to the atrial walls, pulmonary veins, and in particular, the pulmonary arteries. Therefore, it may be advantageous to place a fiduciary marking device into one or more of the pulmonary arteries to ensure precise registration of these structures upon start of the procedure in the operating room. Such precise location registration may greatly aid the surgeon in performance of the dissections of these pericardial reflections. In one embodiment, the location of the lung surface may be of interest. In one embodiment, the tracking of the lung surface may be performed via placement of one or more devices comprising one or more tracking sensor coils on the surface of the lung. In one embodiment, an imaging device, e.g., an endoscopic camera and/or light guide, may be used to allow visual imaging of the surgical site or sites. The imaging device may be used to produce one or more images that may be displayed on a monitor. The one or more images may be coupled with the visual display produced from a guidance or navigation device or system. The imaging device may comprise one or more sensor coils, thereby allowing at least a portion of the imaging device to be tracked and/or guided in 3-D space by the guidance or navigation device or system. The visual display produced by the guidance device may be coupled in an appropriate manner to the visual display produced by the imaging device, thereby providing a physician with real-time monitoring of the imaging device and, thereby providing additional information to allow the physician to easily identify anatomical structures located in the viewing area of the imaging device. In one embodiment, imaging devices may be equipped with one or more sensor coils of a guidance system, thereby allowing distal and proximal portions to be identified easily. For example, flexible and/or deflectable medical devices may require multiple sensors, e.g., sensor coils, to define the location and path of multiple portions of the medical device, e.g., the proximal and distal portions of a flexible and/or deflectable distal medical device.

In one embodiment, sensors may be incorporated in one or more medical devices. A sensor may be attached or coupled directly to the surface of a medical device. A sensor may be incorporated into a medical device. A sensor may be incorporated into a removable sheath, cover or insert that may be placed over or inserted into at least a portion of a medical device. A removable sensor sheath, cover or insert may be disposable or re-useable. A sheath or cover may serve to protect one or more portions of a medical device from one or more body fluids and/or tissues. A sheath or cover may comprise one or more lumens that allow suction, irrigation, and/or passage of guide-wires, catheters or similar flexible, and/or polymeric devices through the sheath and into the working region at the distal end of the medical device. In one embodiment, the guidance device or system may be used during a procedure of guiding, delivery and placement of a stent-graft, e.g., to repair an aneurism, e.g., an abdominal aortic aneurism and/or a thoracic aortic aneurism. In one embodiment, an imaging device or system may be used to acquire a detailed CT or MRI scan of the aortic arterial system, not only to show the aneurism in detail, but to identify the branch sites of numerous arteries. The branch arteries of interest may include the carotid, brachiocephalic trunk, subclavian, bronchial, phrenic, hepatic, cephalic trunk, splenic, mesenteric, renal, lumbar, and iliac arteries. It is generally important to identify these branch arteries and their locations prior to placement of a stent-graft so as to not to occlude any of them during the stent-graft placement procedure. In one embodiment, the delivery stent-graft delivery device may be equipped with one or more sensor coils to allow precise tracking and guidance of the delivery system through the aortic anatomy. A previously acquired image would be critical in determining the optimal stent-graft placement site that may prevent further distension and rupture. During a procedure, branch artery locations would be avoided whenever possible but when the stent-graft placement does cause an occlusion to occur, a previously acquired image may be used to guide the placement of a perforation device and side branch perfusion channel to supply the occluded artery through the wall of the stent-graft.

In one embodiment, one or more images of a patient's anatomy may be produced using one or more imaging device, e.g., an x-ray device, a fluoroscopy device, a CT device, a MRI device, a PET device and/or an ultrasound imaging device. These images may be used in combination with tracked positions of one or more medical devices placed in a patient. These medical devices may be tracked using one or more guidance devices comprising, for example, one or more sensors. The medical devices may also comprise one or more sensors. In one embodiment, a computer generated display showing a medical device's position created by a guidance device or system may be superimposed on a previously acquired image or images produced by one or more imaging devices. In one embodiment, a guidance device or system may include one or more imaging devices. In one embodiment, a guidance device or system may include a controller, e.g., a controller as discussed above. In one embodiment, a guidance device or system may include one or more sensors, e.g., wherein the sensors are coupled to a controller. In one embodiment, a guidance device or system may be slaved to a robotic system or a robotic system may be slaved to a guidance device or system.

In one embodiment, a method of real-time image registration includes monitoring in real-time fixed surface and indwelling fiduciary marking devices so as to update and correct the registration of previously acquired images, e.g., x-ray images, fluoroscopy images, CT images, MRI images, PET images and/or ultrasound images, thereby providing real-time changes in position of the anatomical structures of interest, e.g., respiration, cardiac motion, and intestinal peristalsis.

In one embodiment, a guidance device or system may comprise an electrical sensor, a magnetic field sensor, an optical sensor, an acoustic sensor and/or an inertial sensor. In one embodiment, a guidance device or system may comprise a magnetic field generator. In one embodiment, a sensor coil may comprise an electrically conductive, magnetically sensitive element that may be responsive to time-varying magnetic fields for generating induced voltage signals as a function of, and representative of, the applied time-varying magnetic field.

One embodiment of the present invention comprises an ablation device having one or more ablating elements, e.g. electrodes, ultrasound transducers, microwave elements, cryo-ablation elements, and/or laser elements and one or more sensors, e.g., receiving sensor coils that allow electromagnetic tracking and navigation in 3-D space of the location of one or more of the ablating elements of the ablation device. In one embodiment, the ablation device is a monopolar ablation device. In one embodiment, the ablation device is a bipolar ablation device. In one embodiment, the ablation device is a surgical ablation device. In one embodiment, the ablation device is a minimally invasive device and/or an endoscopic device. In one embodiment, the ablation device comprises one or more portions that are flexible, articulating, malleable and/or rigid.

One embodiment of the present invention includes one or more fiduciary marking or reference devices that may be used to update and correct the registration of previously acquired images, e.g., x-ray images, fluoroscopy images, CT images, MRI images, PET images and/or ultrasound images, thereby providing real-time changes in position of the anatomical structures of interest, e.g., respiration, cardiac motion, and intestinal peristalsis. In one embodiment, a fiduciary marking or reference device is visualizable and/or detectable by one or more means of non-invasive imaging such as x-ray, fluoroscopy, computed tomography, magnetic resonance, PET and/or ultrasound imaging. In one embodiment, the fiduciary marking or reference device may include one or more sensors, e.g., sensor coils, thereby allowing the device's location in 3-D space to be easily determined and used as a reference and/or real-time registration point or points for tracking, navigation and/or guidance, e.g., electromagnetic tracking, navigation and/or guidance, in 3-D space.

One embodiment of the present invention includes a fiduciary reference or marking device which may be fixed in location on or within a patient's body via an adhesive, a tissue fixation screw, helix, barb and/or hook, a suction source, an inflatable balloon, an expandable structure, and/or via physical pressure.

One embodiment of the present invention includes an esophageal device that comprises one or more sensors, e.g., receiving sensor coils, which allow determination of the location of the esophageal device in 3-D space. One embodiment of the present invention includes a trans-esophageal device, e.g., a trans-esophageal imaging device, trans-esophageal stimulation device and/or ablation device, which comprises one or more sensors, e.g., receiving sensor coils, which allow determination of the location of the trans-esophageal device in 3-D space.

One embodiment of the present invention includes a tracheal device that comprises one or more sensors, e.g., receiving sensor coils, which allow determination of the location of the tracheal device in 3-D space. One embodiment of the present invention includes a trans-tracheal device, e.g., trans-tracheal imaging device, trans-tracheal stimulation device and/or trans-tracheal ablation device, which comprises one or more sensors, e.g., receiving sensor coils, which allow determination of the location of the trans-tracheal device in 3-D space.

One embodiment of the present invention includes a vascular device that comprises one or more sensors, e.g., receiving sensor coils, which allow determination of the location of the vascular device in 3-D space. One embodiment of the present invention includes a trans-vascular device, e.g., trans-vascular imaging device, trans-vascular stimulation device and/or trans-vascular ablation device, which comprises one or more sensors, e.g., receiving sensor coils, which allow determination of the location of the trans-vascular device in 3-D space.

One embodiment of the present invention includes a guiding device, e.g., a guiding catheter device, which comprises one or more sensors, e.g., receiving sensor coils, which allow determination of the location of the guiding device in 3-D space. One embodiment of the present invention includes a catheter-like insert device, which may be inserted through the lumen of a larger catheter device, the catheter-like insert device comprising one or more sensors, e.g., receiving sensor coils, which allow determination of the location of the catheter-like insert device in 3-D space.

One embodiment of the present invention includes a stimulation device that comprises one or more sensors, e.g., receiving sensor coils, which allow determination of the location of the stimulation device in 3-D space. One embodiment of the present invention includes a nerve stimulation device, e.g., a vagal nerve stimulation device, which comprises one or more sensors, e.g., receiving sensor coils, which allow determination of the location of the nerve stimulation device in 3-D space.

One embodiment of the present invention includes a tissue-engaging device that comprises one or more sensors, e.g., receiving sensor coils, which allow determination of the location of the tissue-engaging device in 3-D space. One embodiment of the present invention includes a tissue dissection device, which comprises one or more sensors, e.g., receiving sensor coils, which allow determination of the location of the tissue dissection device in 3-D space. One embodiment of the present invention includes a tissue retraction device, which comprises one or more sensors, e.g., receiving sensor coils, which allow determination of the location of the tissue retraction device in 3-D space.

One embodiment of the present invention may comprise one or more tissue ablation devices and/or mapping devices, for example, disclosed in U.S. patent application Ser. No. 10/853,594 filed May 25, 2004, Ser. No. 11/040,663 filed Jan. 21, 2005, Ser. No. 11/128,786 filed May 13, 2005, Ser. No. 11/142,954 filed Jun. 2, 2005, Ser. No. 11/143,400 filed Jun. 2, 2005, Ser. No. 11/143,128 filed Jun. 2, 2005, Ser. No. 11/143,399 filed Jun. 2, 2005, and Ser. No. 11/155,699 filed Jun. 17, 2005. These patent applications are assigned to Medtronic, Inc. and are incorporated herein by reference in their entirety.

A medical procedure according to one embodiment of the present invention may be a non-invasive, minimally invasive and/or invasive procedure. In one embodiment, the medical procedure may entail a port-access approach, a partially or totally endoscopic approach, a sub-xyphoid approach, a sternotomy approach and/or a thoracotomy approach. The medical procedure may include the use of various robotic, imaging systems, and/or guidance systems. The medical procedure may be a procedure comprising the heart. Alternatively, the medical procedure may be a procedure comprising another organ of the body. The medical procedure may be a procedure comprising more than one organ of the body. In one embodiment, on or more medical devices of the present invention may be positioned and used, for example, through a sternotomy, through a thoracotomy that avoids the sternal splitting incision of conventional cardiac surgery, through a mini-thoracotomy, through a sub-xyphoid incision, percutaneously, transvenously, arthroscopically, endoscopically, for example, through a percutaneous port, through a stab wound or puncture, through a small or large incision, for example, in the chest, in the groin, in the abdomen, in the neck or in the knee, or in combinations thereof. In one embodiment, on or more medical devices of the present invention may be guided into a desired position using various imaging and/or guidance techniques as described herein.

Figure 20:
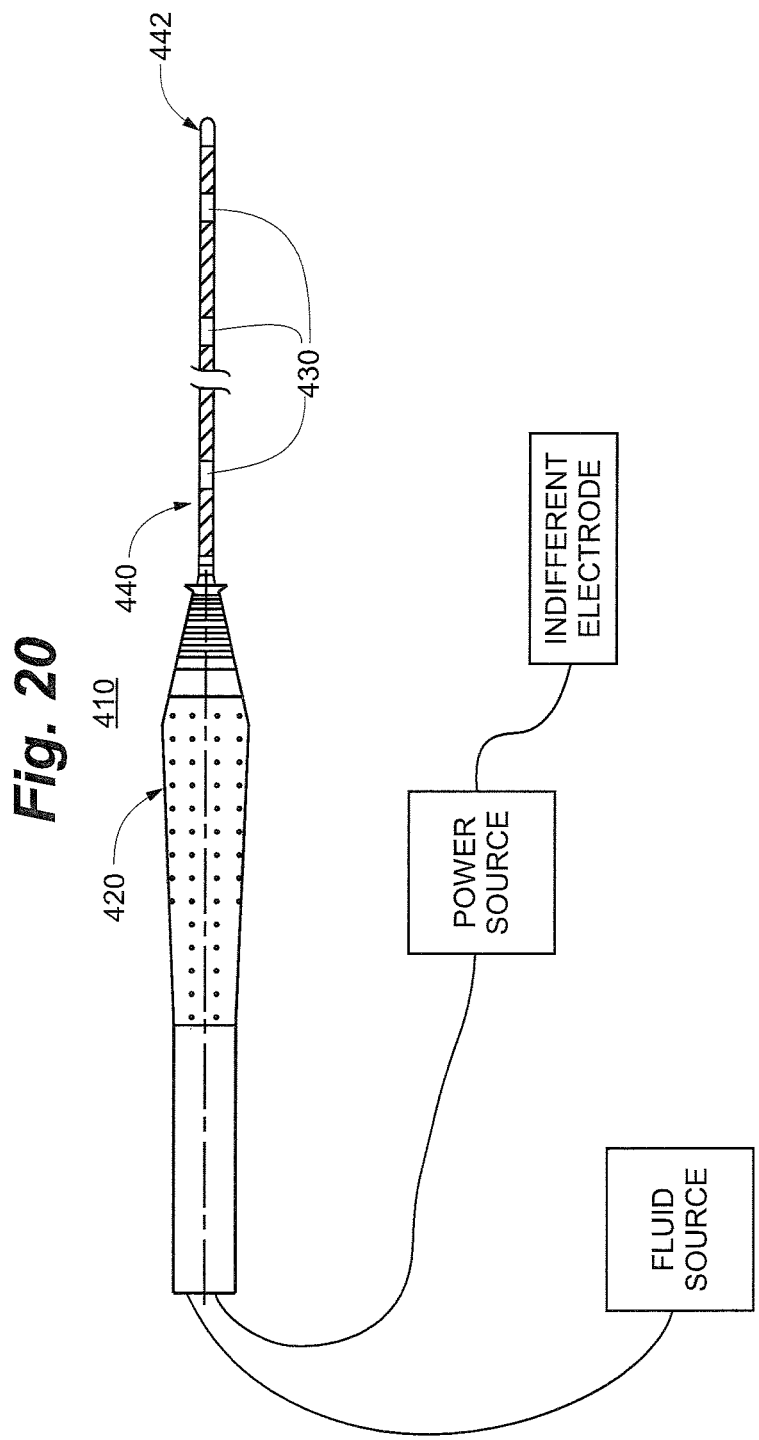
FIG. 20 is an illustration of one embodiment of a medical device in use in accordance with the present invention.

FIG. 20 shows an ablation device 410 which may be used according to one embodiment of the present invention. Ablation device 410 comprises an elongated member or shaft 440, which couples an ablating tip 442, which comprises one or more ablating elements, to a handle 420 that may be held and manipulated by a surgeon. In one embodiment, ablation device 410 comprises one or more sensors. For example, shaft 440 of ablation device 410 may comprise one or more sensors 430, e.g., one or more sensor coils, thereby allowing the device to be tracked within a patient's body via an image guidance device or system as described herein. The ablation device may include a fluid source, an indifferent electrode and an ablating power source, e.g., an RF energy source.

In one embodiment, once the target site (e.g., right atrium, left atrium, epicardial surface, endocardial surface, etc.) is accessible, the surgeon guides the ablating tip 442 of the ablation device 410 to the target site. The surgeon may use pre-acquired images, as described above, and an image guidance system, as described above, to help guide the ablating tip 442 into position. Once the ablating tip 442 is located in a desired position, the ablating tip 442 is then energized, ablating (or for some applications, cauterizing) the contacted tissue. A desired lesion pattern may then be created (e.g., portions of a known "Maze" procedure) by guiding the tip in a desired fashion along the target site, for example. The image guidance system of the present invention may allow a minimally invasive ablation procedure to occur without a physician having direct visualization. The image guidance system described herein may enable a physician to know the proximity of an ablating member to a cardiac structure, e.g., a coronary artery, and/or extra-cardiac structures, e.g., an esophagus, prior to ablating. The image guidance system of the present invention may allow an ablation lesion path or line that a physician creates to be marked on a cardiac image, thereby helping to guide the physician in creating a complete lesion set of an ablation procedure.

Figure 21:
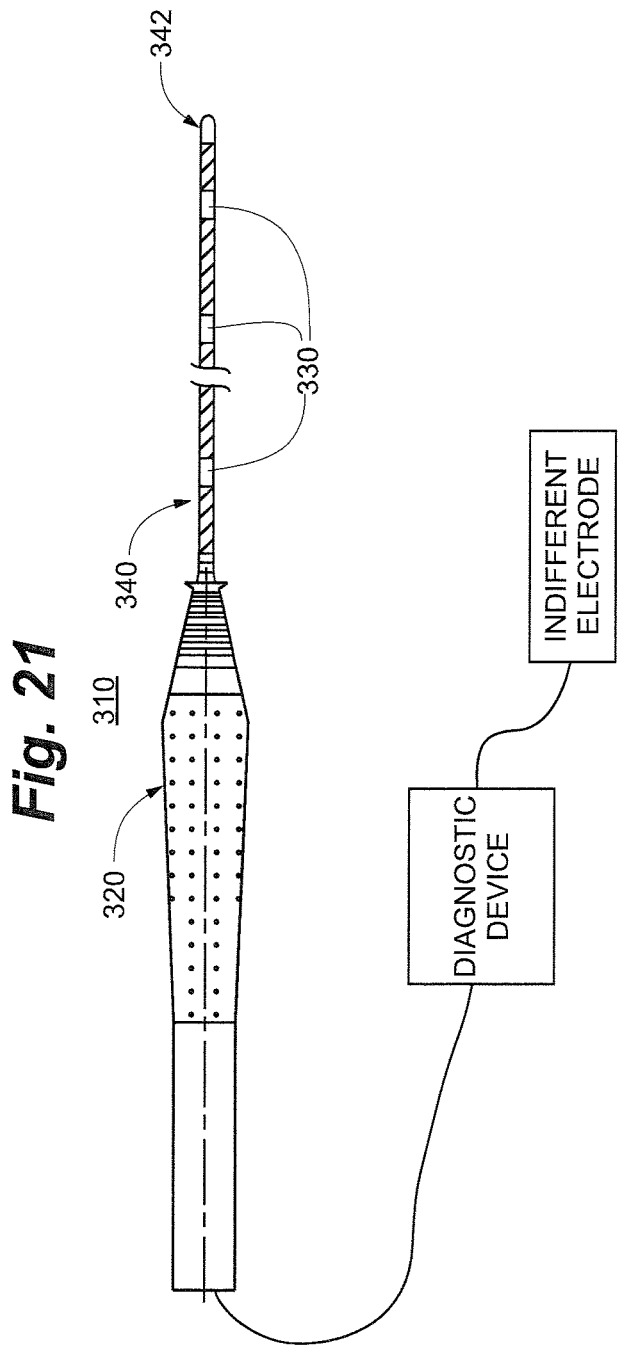
FIG. 21 is an illustration of one embodiment of a medical device in use in accordance with the present invention.

FIG. 21 shows a mapping device 310 which may be used according to one embodiment of the present invention. Mapping device 310 comprises an elongated member or shaft 340, which couples a mapping tip 342, which may comprise one or more mapping electrodes, to a handle 320 that may be held and manipulated by a surgeon. In one embodiment, mapping device 310 comprises one or more sensors. For example, shaft 340 of mapping device 310 may comprise one or more sensors 330, e.g., one or more sensor coils, thereby allowing the device to be tracked within a patient's body via an image guidance device or system, as described herein. The mapping device may include a diagnostic device and an indifferent electrode.

In one embodiment of the present invention, it may be desirable to identify an origination point of an undesired electrical impulse of the heart prior to ablation. Mapping may be accomplished by placing one or more mapping electrodes into contact with the tissue in question. Mapping of tissue may occur by placing one or more mapping electrodes into contact with the endocardial surface of the heart and/or the epicardial surface of the heart. In one embodiment, once the target site (e.g., right atrium, left atrium, epicardial surface, endocardial surface, etc.) is accessible, the surgeon guides the mapping tip 342 of the mapping device 310 to the target site. The surgeon may use pre-acquired images, as described above, and an image guidance system, as described above, to help guide the mapping tip 342 into position. Once the mapping tip 342 is located in a desired position, mapping may occur.

Mapping may occur on isolated or non-isolated tissues on or near the left atrium for lesion evaluation following an ablation procedure, for example. Mapping may also allow marking and cataloging of sites where autonomic ganglia are found. In cases where biventricular pacing leads are to be placed, the mapping device may be guided into various locations to identify the optimal pacing site. The optimal pacing site may then be marked on a previously acquired cardiac image. The location of various structures, e.g., a phrenic nerve, may be marked on a previously acquired image as well when it is located by a mapping/stimulation device according to one embodiment.

Figure 22:
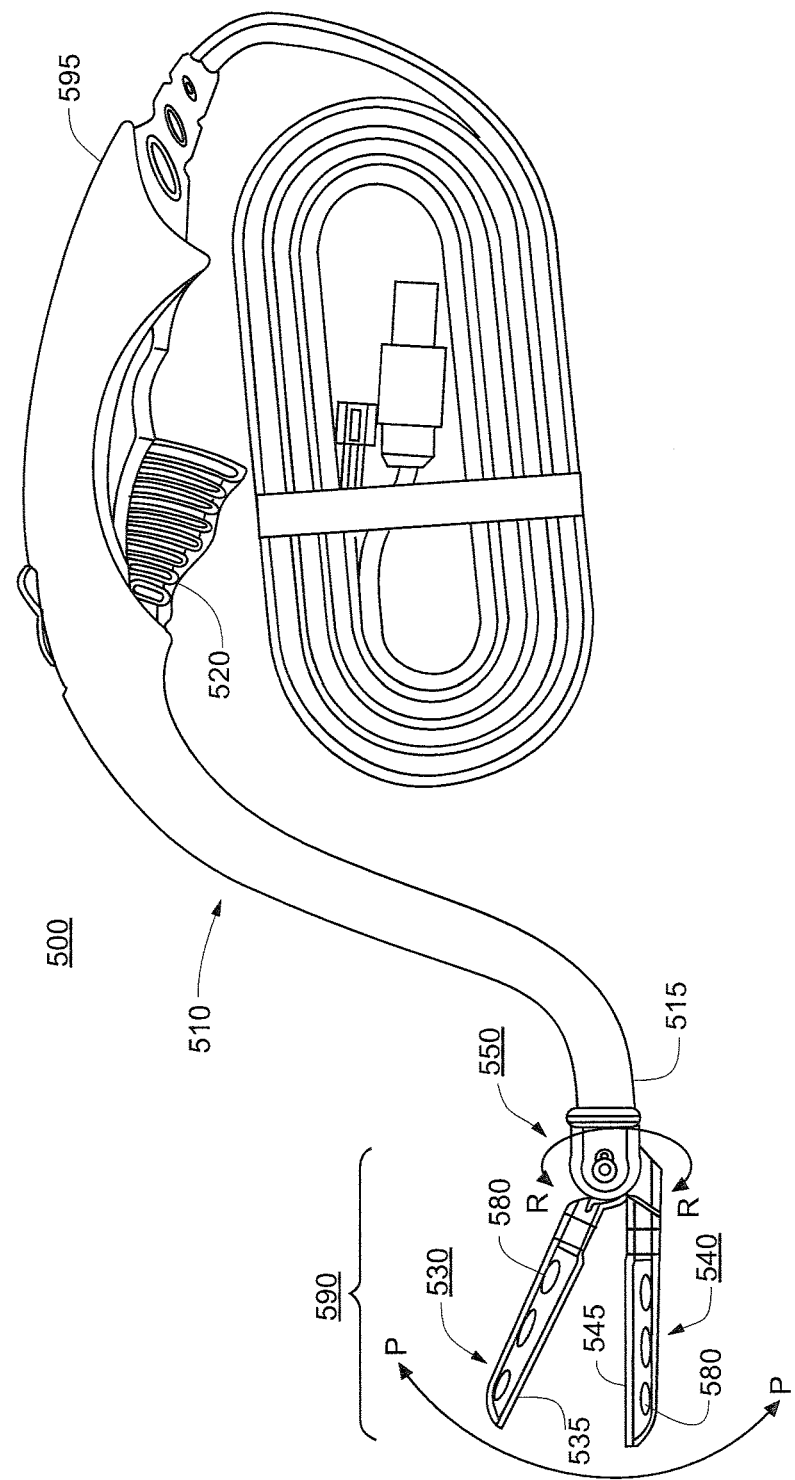
FIG. 22 is an illustration of one embodiment of a medical device in use in accordance with the present invention.

FIG. 22 shows an ablation device 500 which may be used according to one embodiment of the present invention. Ablation device 500 generally comprises an elongated handle assembly 510 having a jaw assembly 590 mounted at handle distal end 515, a trigger 520 intermediate the handle proximal and distal ends 595 and 515. The trigger 520 is employed to move the jaws of the first or lower jaw assembly 540 with respect to the second or upper jaw assembly 530 of the jaw assembly 590 together to compress tissue therebetween to allow for creation of a linear ablation lesion to occur by emitting ablative energy from ablating jaw members 530 and 540.

The upper jaw and lower jaw assemblies 530 and 540 have opposed upper and lower jaws 535 and 545, respectively, each comprising an ablating element, e.g., an electrode assembly. The swivel assembly 550 provides the physician with the opportunity to position the jaw assembly 590 in a variety of orientations relative to the handle 510, to facilitate placing the 535 and 545 jaws against tissue to form desired lines of lesions, e.g., the heart wall in performance of a Maze procedure or a modified Maze procedure. In one embodiment, the physician may manually grasp and rotate the swivel assembly 550 and the jaw assembly 590 to provide a roll adjustment R, preferably through an arc of at least 300 degrees, relative to the axis of the distal end 515 of the handle 510 through interaction of components of the handle and swivel assembly. In one embodiment, the physician may manually grasp the jaw assembly 590 and adjust it in pitch P relative to the swivel assembly 550 through the interaction of components of the jaw assembly 590 and the swivel assembly 550. In one embodiment, the available arc of pitch P adjustment extends over at least 90 degrees. Moreover, the upper and lower jaws 535 and 545 may be malleable. In one embodiment, ablation device 500 comprises one or more sensors. For example, jaw assembly 590 may comprise on or more sensors 580, e.g., one or more sensor coils, thereby allowing the device jaws to be tracked within a patient's body via an image guidance device or system as described herein. The ablation device may include a fluid source and an ablating power source, e.g., an RF energy source.

In one embodiment, once the target site (e.g., right atrium, left atrium, epicardial surface, endocardial surface, etc.) is accessible, the surgeon guides the jaw assembly 590 of the ablation device 500 to the target site. The surgeon may use pre-acquired images, as described above, and an image guidance system, as described above, to help guide the jaw assembly 590 into position. The image guidance system may allow a physician to verify that the ablating elements of the jaw assembly are positioned properly prior to ablation. Once the jaw assembly 590 is located in a desired position, the ablating elements of jaw assembly 590 are then energized to ablate (or for some applications, cauterize) the contacted tissue. A desired lesion pattern may then be created (e.g., portions of a known "Maze" procedure) by guiding the jaw assembly into one or more desired positions. The image guidance system of the present invention may allow a minimally invasive ablation procedure to occur without a physician having direct visualization. The image guidance system described herein may enable a physician to know the proximity of an ablating member to a cardiac structure, e.g., a coronary artery, and/or extra-cardiac structures, e.g., an esophagus, prior to ablating. The image guidance system of the present invention may allow an ablation lesion path or line that a physician creates to be marked on a cardiac image, thereby helping to guide the physician in creating a complete lesion set of an ablation procedure. Multiple sensors, e.g., sensor coils, incorporate into ablation device 500 may allow a physician to tell if the ablation jaws are bent to either side and/or if the jaws are skewed. The line of tissue clamped between the jaws may be marked on a cardiac image to record the lesion location.

Figure 23:
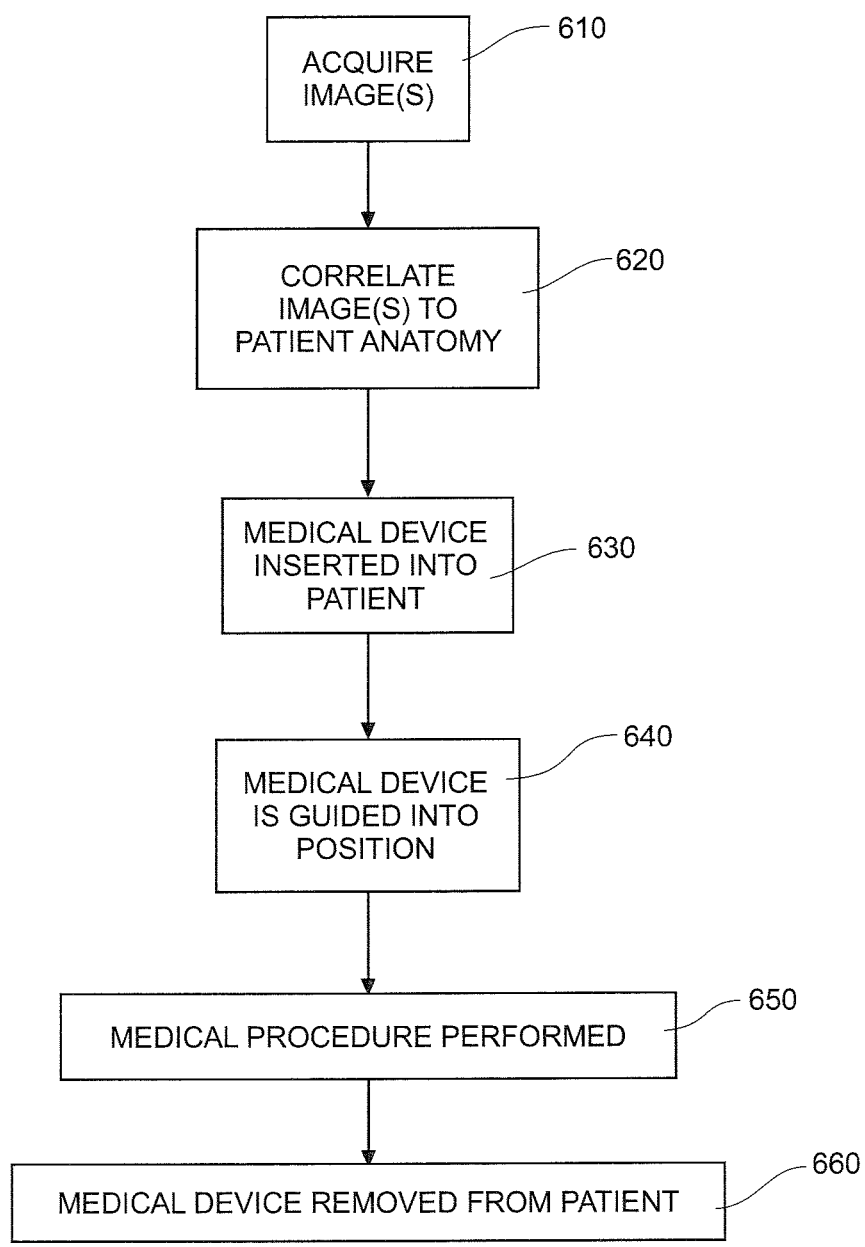
FIG. 23 is a flow diagram of one embodiment of the present invention.

One embodiment of a method according to the present invention is outlined in FIG. 23. An imaging device acquires one or more images, as described herein, of a patient's anatomy of interest at 610. Next an image guidance system comprising reference markers, as described herein, is used to correlate the acquired image(s) with the patient's anatomy at 620. A medical device, e.g., an ablation device, comprising one or more image guidance sensors is then inserted into the patient at 630. The medical device is then guided into a desired position, e.g., adjacent cardiac tissue, using the image guidance system at 640. A medical procedure, e.g., an ablation procedure comprising the ablation of cardiac tissue, is performed at 650. The medical device is removed from the patient at 660.

As described herein, an imaging device may be used to acquire an image (or images) of an anatomy of interest, or an anatomical area of interest, within the patient. Examples of types of imaging devices that may be used in various embodiments of the invention include ultrasound, CT, MRI, PET, fluoroscopy, and echocardiography devices. The acquired image may be registered to the patient, which may allow for correlation of the acquired image with the anatomy of the patient, for example, to provide real-time (or near real-time) monitoring and guidance of a medical device with respect to a patient's anatomy. An image guidance system according to an embodiment of the invention may provide a visual display of the locations or positions of medical devices (or portions of medical devices, such as sensors) relative to one or more of the acquired images, for example, during medical procedures such as cardiac ablations.

In some embodiments, the method outlined generally in FIG. 23 includes guiding the ablation device to an energy delivery location within the patient. Suitable energy delivery locations within the patient include areas within the patient's body that are relatively easily accessible, and which may allow placement of the ablation device (or a portion of the ablation device) so that it is disposed a known or appropriate distance from a target area of tissue. For example, in some embodiments, the energy delivery location may be selected from any of the following: the esophagus, the trachea, or bronchi of the lungs of the patient. Such locations may, for example, be suitable for delivering HIFU energy to an anatomy of interest in the patient, such as cardiac tissue located a distance from the energy delivery location. The anatomy of interest may include cardiac tissue to be ablated to treat atrial fibrillation in certain embodiments, for example, according to a Maze procedure. HIFU energy may be emitted from a HIFU emitting member of the ablation device disposed at the energy delivery location to the cardiac tissue to be ablated according to a Maze procedure according to certain embodiments of the invention. The anatomy of interest may include cardiac tissue near the pulmonary veins, for example. Certain embodiments may include guiding at least a portion of an ablation device (such as a HIFU emitting member) to the energy delivery location using transesophageal echocardiography (TEE).

Figure 24:
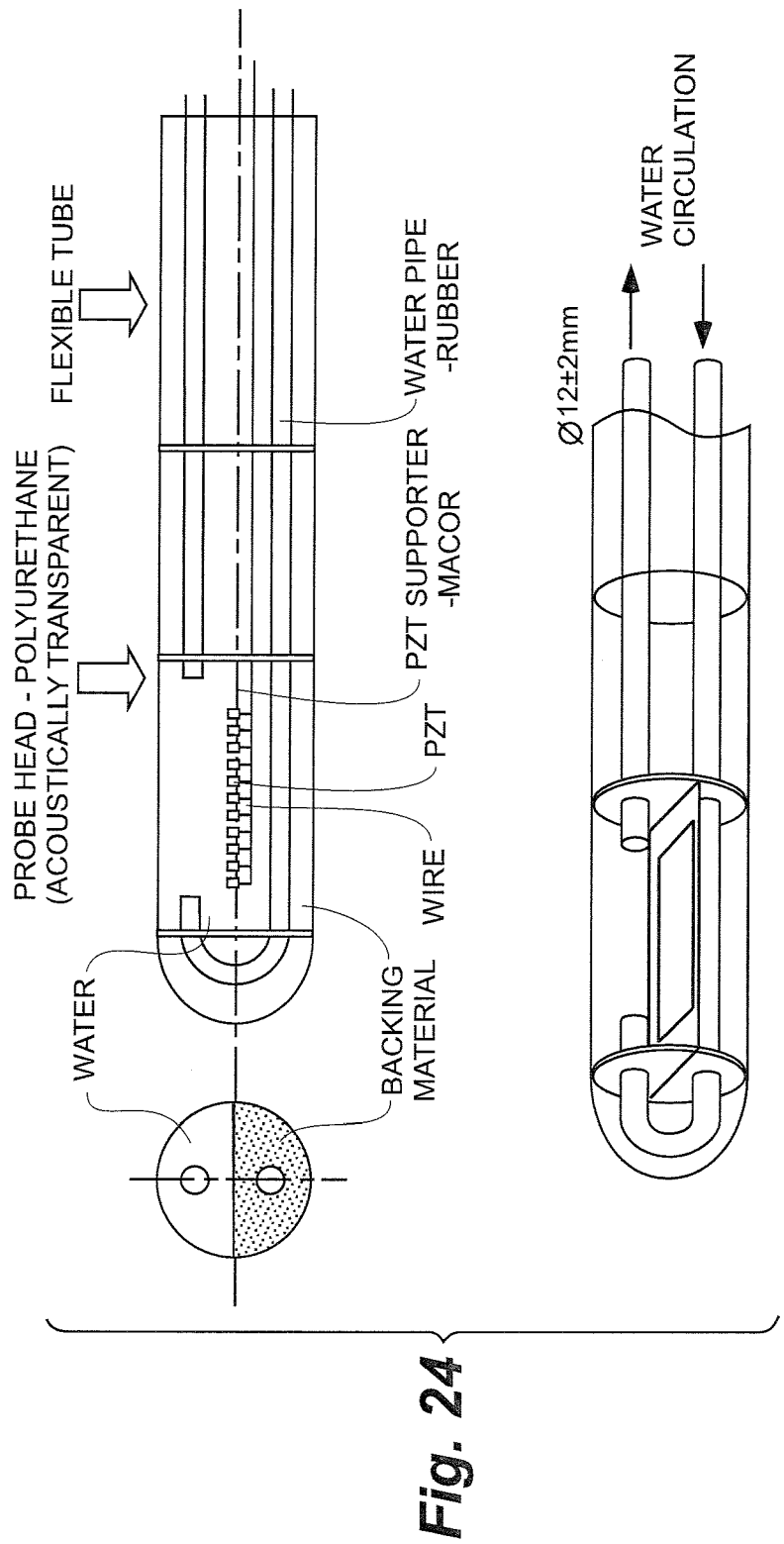
FIG. 24 is a cross-sectional view of a portion of one embodiment of a medical device in accordance with the present invention.
Figure 26B:
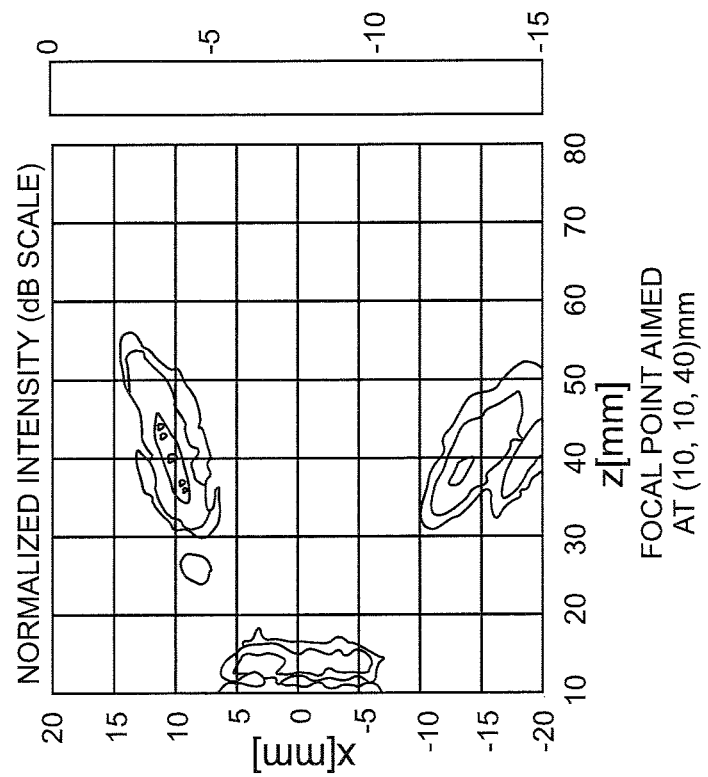
FIGS. 26a and 26b are illustrations of simulation results of an ultrasound field in accordance with one embodiment of the present invention.
Figure 26A:
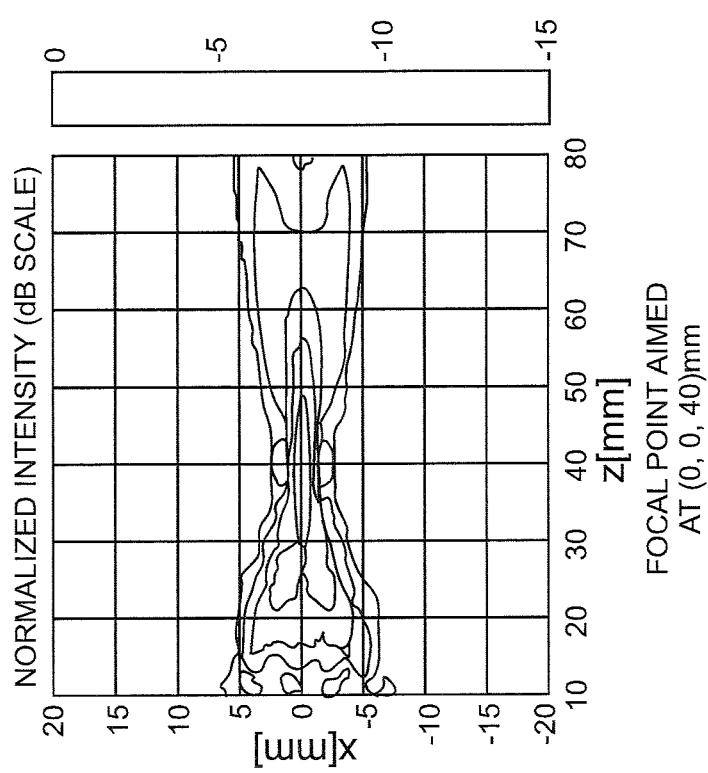

The distal portion comprising an ultrasound emitting member of one embodiment of a medical device according to the present invention is shown in FIG. 24. The ablation device shown in FIG. 24 may be used in trans-esophageal ultrasound ablation of cardiac tissue, for example. In one embodiment of the present invention, the flexible tube or shaft has a length and rigidity sufficient for manipulating the distal portion of the device or probe head attached to the distal end of the flexible tube or shaft down within the esophagus of a patient. The proximal end of the flexible tube may reside outside of the patient's body while the distal end resides within the patient's body, e.g., the patient's esophagus. According to one embodiment of the present invention, an array of transducer elements as shown in FIG. 25 may be used in trans-esophageal ultrasound ablation of cardiac tissue. FIG. 25 shows a 2-D 64-element sparse (spatially sampled from 15-by-13 elements) tapered phased array with total size of approximately about 20.72×10.24 mm² with the proportions of ceramic and matching layers. FIGS. 26a and 26b show the simulation results of the ultrasound field of the normalized intensity for on-axis focusing with the focal point aimed at (a) (0, 0, 40) mm and off-axis focusing at (b) (10, 10, 40) mm plotted as a contour with levels indicated at 0, −1, −2, −3, −6, −9 and −12 dB. According to the simulation results, the transducer array of FIG. 25 may produce well-defined zones for both on-axis and off-axis focusing and reduced grating lobes, which can cause an unwanted ablation in tissue.

Figure 27:
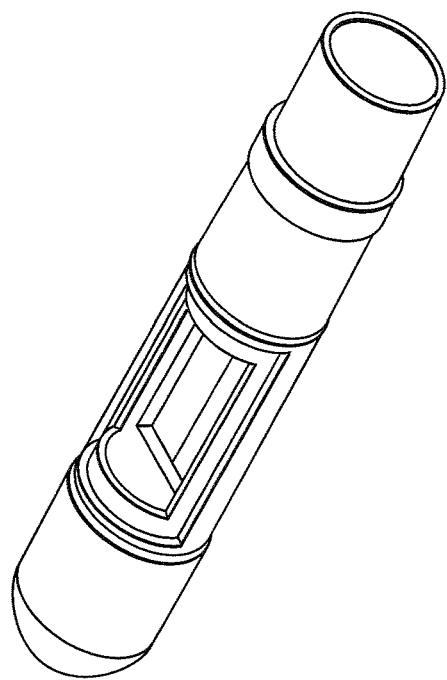
FIG. 27 is a view of a portion of one embodiment of a medical device in accordance with the present invention.
Figure 28:
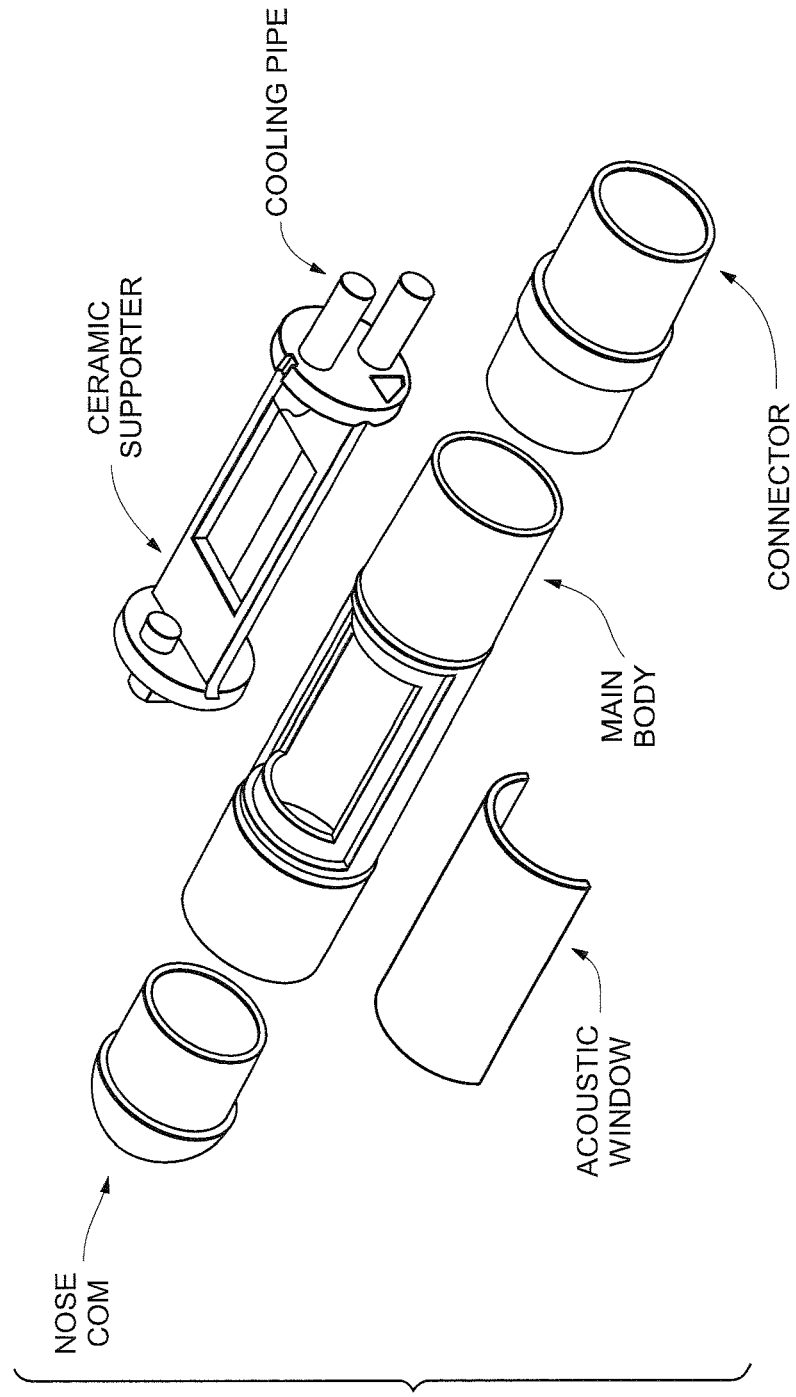
FIG. 28 is an exploded view of a portion of one embodiment of a medical device in accordance with the present invention.

In one embodiment of the present invention, the transducer design is a 2-D phased array with flat tapered transducer elements. The spatially sparse array uses 64 active elements operating at frequency of 1.6 MHz sampled from 195 (15-by-13) rectangular elements. The ablating probe head, which may be MRI-compatible, includes a housing, e.g., 19 mm in diameter, an acoustic window or membrane, e.g., a latex membrane, to protect the transducer elements and to ensure the delivery of maximum acoustical power from the transducer elements to the ablation target(s), cooling pipes/lumens, connectors and a flexible insertion tube, as shown in FIGS. 27 and 28. In one embodiment of the present invention, the main body may have a length of approximately about 67 mm and a diameter of approximately about 18 mm.

Figure 29:
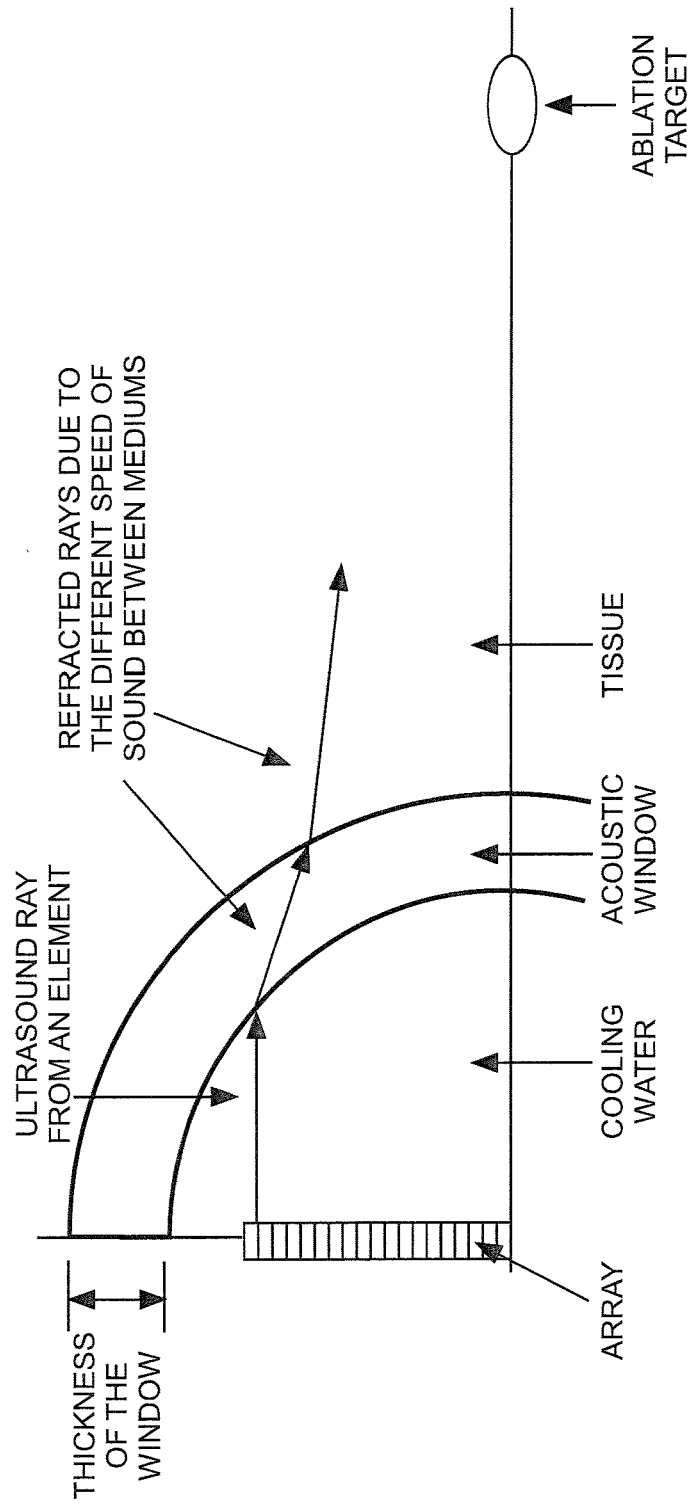
FIG. 29 is a diagram of a portion of one embodiment of a medical device in accordance with the present invention.
Figure 30:
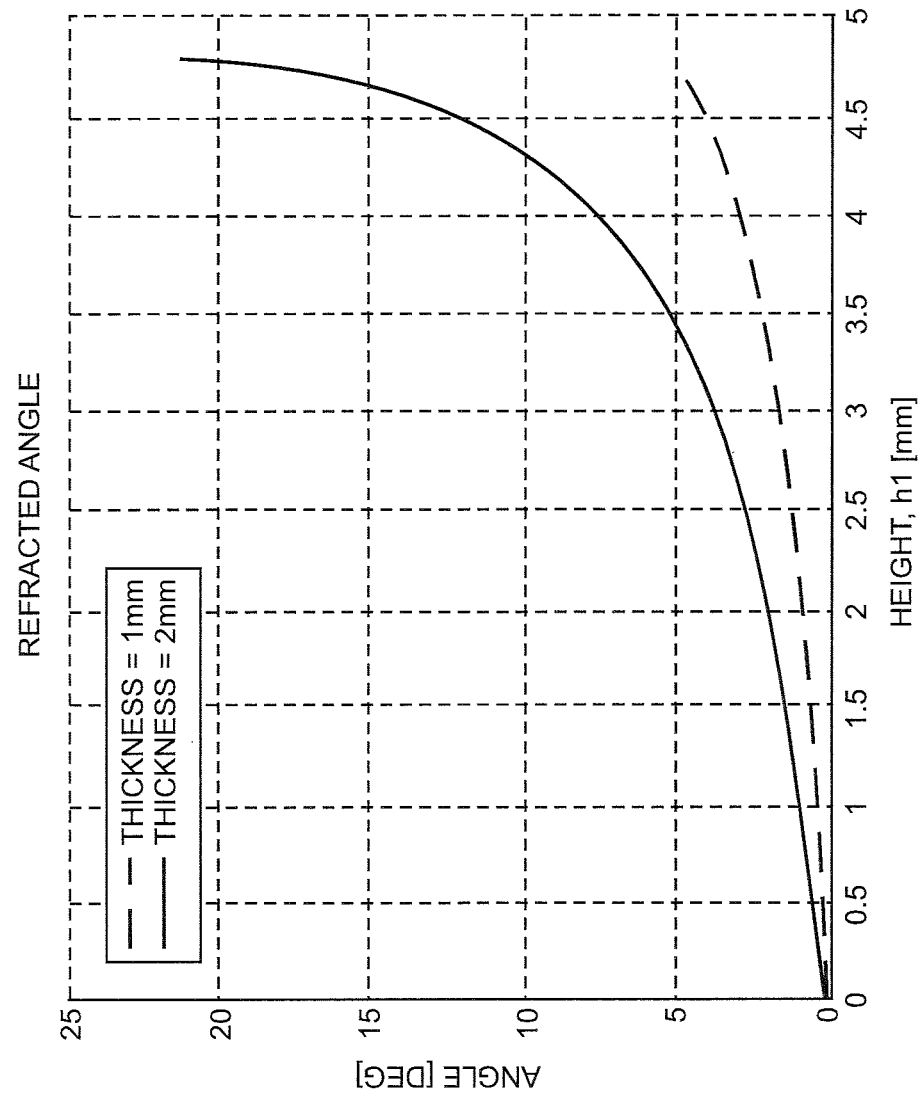
FIG. 30 is a graph in accordance with one embodiment of with the present invention.
Figure 31A:
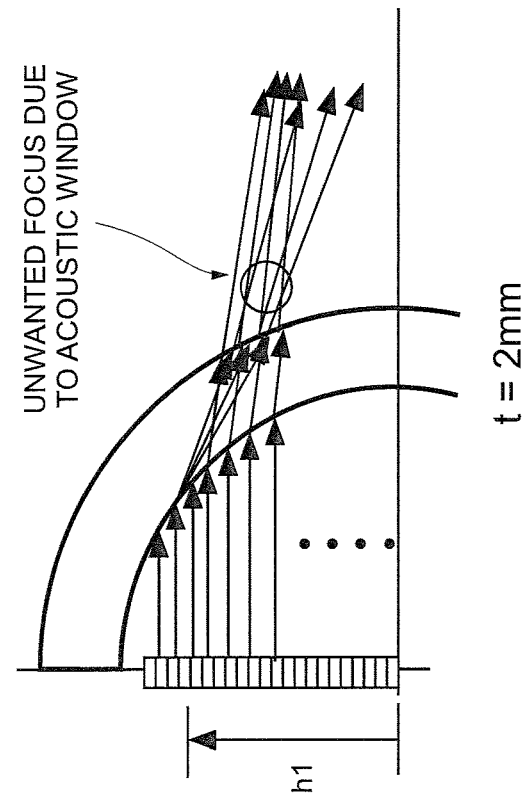
FIGS. 31a and 31b are diagrams of a portion of one embodiment of a medical device in accordance with the present invention.
Figure 31B:
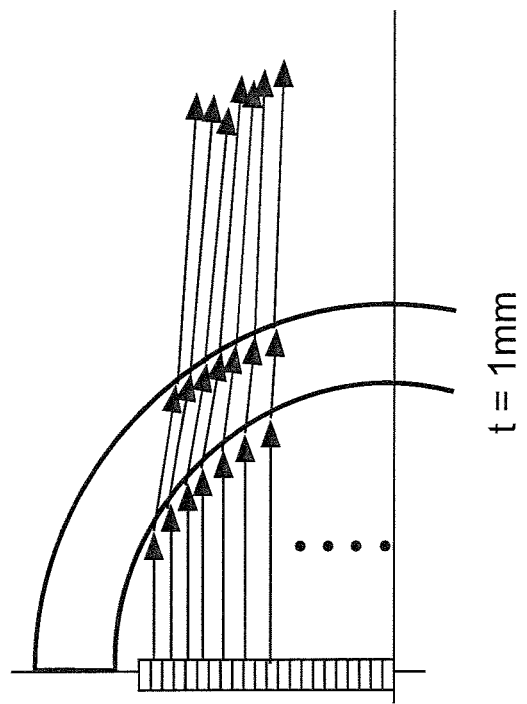

In one embodiment of the present invention, the acoustic window may comprise a latex membrane. The membrane helps to create a bolus of fluid, e.g., water, delivered by the cooling pipes/lumens around the transducer elements. The fluid helps to provide a good coupling between the device and tissue, e.g., the esophageal wall. It is desirable that the material used to create the acoustic window have similar acoustic impedance as does the fluid surrounding the transducers, so as to be acoustically transparent. It should avoid extreme refraction of the ultrasound beam due to the different propagation speed between the cooling fluid surrounding the transducers and the window, and the window and the esophageal wall, for example, which may cause unwanted heating around the esophageal wall. To simulate the refraction of the ultrasound beam due to the acoustic window, a half-cylindrical window with TPX® (Z=1.78 MRayls, c=2170 m/s) was modeled with water (Z=1.5 MRayls, c=1500 m/s) and Tissue (Z=1.5 MRayls, c=1500 m/s) and refracted angles according to the height of each element was calculated, as shown in FIGS. 29 and 30. The resulting ultrasound rays are illustrated in FIGS. 31a and b wherein the thickness of the window wall is 2 mm and 1 mm, respectively. As shown in FIGS. 30 and 31, the thickness of the acoustic window is a factor of the ultrasound beam when two mediums have different speed of sound though they have similar impedance. Because uncontrolled heating in virtue of the extreme refracted angles of ultrasound beam depicted in FIG. 31a can cause damage to the esophageal wall, for example, the thickness of the window must be carefully selected.

In one embodiment of the present invention, the transducer array may comprise ceramic: PZT-8 (Z=MRayls), Insulcast® 501 and silver epoxy (Z=7.14 MRayls), coaxial cable and epoxy. The probe head housing may comprise polyurethane and/or Delrin® for the housing body, acoustically transparent polyurethane and/or TPX® for the acoustic window, a machinable glass ceramic, e.g., Macor® and/or Delrin® for the ceramic supporter, polyurethane and/or Delrin® for the nose-corn and connectors and polyurethane (spray) and/or sealing tape for sealing. The flexible tube may comprise polyurethane, silicone, TPFE and/or Tygon® tubing. The cooling pipes may comprise copper within the probe head and rubber within the flexible tube.

Figure 32:
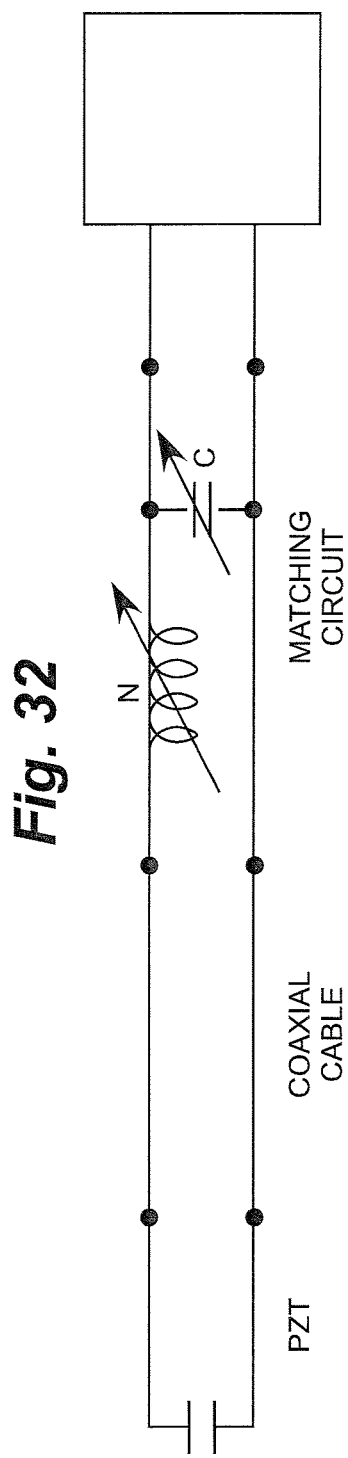
FIG. 32 is a schematic of a circuit in accordance with one embodiment of the present invention.

In one embodiment of the present invention, the device may comprise electrical impedance matching circuits. For example, individual LC circuits may be built for each of the transducer elements to match each one to a common value, e.g., 50 Ω<0°. An impedance matching equivalent circuit is shown in FIG. 32. The impedance of the matching circuit may be adjusted by varying the value of the capacitance and the number of turns of coils.

In one embodiment of the present invention, an amplifier system may be used to power or drive the transducer array. The power source or amplifier system may be a multi-channel high power, ultrasound phased-array transducer driver for 64 elements which may be capable of delivering 50 W per channel with ±1° phase resolution each.

In one embodiment of the present invention, the transducer array may be fabricated from piezoelectric ceramic, PZT-8. The ceramic material may be diced in 20.70 mm×10.24 mm and lapped to a thickness of 1.437 mm corresponding to the resonance frequency of 1.6 MHz. The ceramic has the electrode surfaces coated with chromium and gold sputtering and thin oxidized silver matching layer on the surface that radiate ultrasound into the tissue. The thickness and material of the matching layer may be selected based on the solution to a three-layer (transducer, matching layer and tissue) problem, which ensures the required maximum power transfer. The matching layer in one embodiment is a 2:1, epoxy of Insulcast® 501 to silver powder mixture. FIGS. 33a, b and c show views of a transducer array at different stages of the fabrication process. FIG. 33a shows a lapped, gold-sputtered, and matching layer-attached piezo-ceramic (20.70×10.24 mm²). FIG. 33b shows a diced array imbedded in the frame. The ceramic was completely diced through its thickness to form a 64-element sparse phased array and attached securely to the frame using silicone with a primer. FIG. 33c shows a wired array following the soldering of wires to the ceramic elements. In one embodiment of the present invention, the elements are soldered to MRI compatible, 42 AWG, 30 pF/ft miniature coaxial cables, each 2.5 meters long. The cables are used to connect the transducer elements of the phased array to the amplifier system. In one embodiment, a micro-tip soldering pin at low temperature (less than the Curie temperature of PZT-8) was used to solder the core of each coaxial cable to its designated element. For this process, the soldering temperature was kept below 500° F. to prevent any damage to the piezoelectric ceramic.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference in its entirety, as if each such patent or publication were individually incorporated by reference herein.

What is claimed is:

1. A method for trans-esophageal ablation of cardiac tissue in a patient comprising:
    providing a trans-esophageal ablation device comprising a flexible, elongate portion adapted to be guided within an esophagus of said patient, a source of energy, and a two-dimensional array of transducer elements configured to deliver high intensity focused ultrasound (HIFU) energy to a focus zone within said patient, the focus zone being at a predetermined distance from the trans-esophageal ablation device;
    inserting said trans-esophageal ablation device into an esophagus of said patient;
    positioning said two-dimensional array of transducer elements of said trans-esophageal ablation device proximate esophagus tissue at the predetermined distance from said cardiac tissue of said patient;
    focusing said focus zone of said two-dimensional array of transducer elements on said cardiac tissue of said patient; and
    delivering high intensity focused ultrasound (HIFU) energy to said cardiac tissue of said patient to form a lesion at said cardiac tissue within said focus zone without forming a lesion in patient esophagus tissue proximate said trans-esophageal ablation device; wherein said two-dimensional array of transducer elements have a taper wherein transducer elements positioned more centrally in said two-dimensional array of transducer elements are larger than transducer elements positioned more peripherally in said two-dimensional array of transducer elements, and further wherein the step of delivering high intensity focused ultrasound (HIFU) energy to said cardiac tissue includes operating said two-dimensional array of transducer elements to focus said high intensity focused ultrasound (HIFU) energy from said two-dimensional array of transducer elements to said focus zone within said patient.

2. The method of claim 1 wherein said high intensity focused ultrasound (HIFU) energy delivered from said two-dimensional array of transducer elements is at least approximately three decibels greater intensity at said focus zone in comparison with a grating lobe.

3. The method of claim 1 wherein said trans-esophageal ablation device further comprises an impedance match circuit operatively coupled to the two-dimensional array of transducer elements, and wherein said focusing step comprises providing, at least in part, an approximately equal impedance for each transducer element of said two-dimensional array of transducer elements.

4. The method of claim 3 wherein said impedance is approximately fifty ohms at a temperature of zero degrees centigrade.

5. The method of claim 1, wherein each transducer element of said two-dimensional array of transducer elements are independently actuatable, and wherein said focusing step comprises independently actuating each transducer element.

6. The method of claim 1, wherein the step of delivering high intensity focused ultrasound (HIFU) energy to said cardiac tissue of said patient to form a lesion at said cardiac tissue includes focusing said high intensity focused ultrasound (HIFU) energy through a wall of said esophagus and into said cardiac tissue.

7. The method of claim 1, wherein the step of inserting said trans-esophageal ablation device into an esophagus of said patient includes inserting said trans-esophageal ablation device through an oral cavity of said patient.

8. The method of claim 1, wherein the step of positioning said two-dimensional array of said trans-esophageal ablation device at the predetermined distance from said cardiac tissue includes using transesophageal echocardiography (TEE).

9. The method of claim 1, further comprising:
    manipulating a tissue-engaging device apart from said trans-esophageal ablation device to move a heart of said patient to position cardiac tissue of said heart at the predetermined distance from said trans-esophageal ablation device.

10. The method of claim 1, wherein each transducer element of said two-dimensional array of transducer elements are selectively actuatable to allow for electronic steering of said high intensity focused ultrasound (HIFU) energy.

11. A method for trans-esophageal ablation of cardiac tissue in a patient comprising:
    providing an ablation device configured to ablate cardiac tissue from within an esophagus of the patient, the ablation device configured to deliver high intensity focused ultrasound (HIFU) energy to a focus zone at a predetermined distance from an array of transducer elements; wherein the array of transducer elements have a taper wherein individual transducer elements positioned more centrally in the array are larger than individual transducer elements positioned more peripherally in the array;
    inserting the ablation device into the esophagus;
    positioning the array of transducer elements proximate esophagus tissue at the predetermined distance from cardiac tissue;
    focusing the focus zone on cardiac tissue to be ablated; and
    delivering high intensity focused ultrasound (HIFU) energy through the wall of the esophagus to ablate cardiac tissue within the focus zone without ablating esophagus tissue proximate the array of transducer elements.

12. The method of claim 11, wherein each transducer element of the array of transducer elements are selectively actuatable to allow for electronic steering of said high intensity focused ultrasound (HIFU) energy.

* * * * *